US011857410B2

(12) United States Patent
Bennett et al.

(10) Patent No.: US 11,857,410 B2
(45) Date of Patent: Jan. 2, 2024

(54) SUTURE GUARD FOR A PROSTHETIC VALVE

(71) Applicant: EDWARDS LIFESCIENCES CORPORATION, Irvine, CA (US)

(72) Inventors: Nathan L. Bennett, Flagstaff, AZ (US); Ryan S. Titone, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 267 days.

(21) Appl. No.: 17/181,747

(22) Filed: Feb. 22, 2021

(65) Prior Publication Data

US 2021/0169642 A1 Jun. 10, 2021

Related U.S. Application Data

(63) Continuation of application No. 16/170,795, filed on Oct. 25, 2018, now Pat. No. 10,959,838.

(60) Provisional application No. 62/579,761, filed on Oct. 31, 2017.

(51) Int. Cl.
*A61F 2/24* (2006.01)
*A61B 17/04* (2006.01)

(52) U.S. Cl.
CPC .......... *A61F 2/2409* (2013.01); *A61F 2/2427* (2013.01); *A61B 2017/0496* (2013.01); *A61F 2/2412* (2013.01); *A61F 2/2454* (2013.01); *A61F 2220/0075* (2013.01)

(58) Field of Classification Search
CPC .... A61F 2/2409; A61F 2/2427; A61F 2/2412; A61F 2/2454; A61F 2220/0075; A61B 2017/0496
See application file for complete search history.

(56) References Cited

U.S. PATENT DOCUMENTS

| 1,160,707 A | 11/1915 | Garber |
| 3,409,013 A | 11/1968 | Berry |
| 3,546,710 A | 12/1970 | Shumakov et al. |

(Continued)

FOREIGN PATENT DOCUMENTS

| WO | 02/49545 A2 | 6/2002 |
| WO | 2013/128432 A1 | 9/2013 |

(Continued)

OTHER PUBLICATIONS

International Search Report and Written Opinion received for PCT Patent Application No. PCT/US2018/057796, dated Feb. 28, 2019, 17 pages.

(Continued)

*Primary Examiner* — Julian W Woo
(74) *Attorney, Agent, or Firm* — Chang & Hale

(57) ABSTRACT

A system includes a heart valve and a device that functions to minimize a possibility for suture becoming entangled with a commissure post of the heart valve during an implantation procedure. In some examples, the device is a suture guard that includes one or more features that deflect suture to help minimize entanglement of the same with the commissure posts of the heart valve. In some examples, the features operate to deflect the commissure posts radially inwardly, while in other examples, the features overlay the commissure posts without deflecting that same.

24 Claims, 44 Drawing Sheets

(56) References Cited

U.S. PATENT DOCUMENTS

| | | |
|---|---|---|
| 3,710,744 A | 1/1973 | Goodenough et al. |
| 4,011,947 A | 3/1977 | Sawyer |
| 4,065,816 A | 1/1978 | Sawyer |
| 4,182,446 A | 1/1980 | Penny |
| 4,211,325 A | 7/1980 | Wright |
| 4,585,453 A | 4/1986 | Martin et al. |
| 4,655,218 A | 4/1987 | Kulik et al. |
| 4,683,883 A | 8/1987 | Martin |
| 4,834,097 A | 5/1989 | Phillips et al. |
| 4,865,600 A | 9/1989 | Carpentier et al. |
| 4,878,494 A | 11/1989 | Phillips et al. |
| 4,932,965 A | 6/1990 | Phillips |
| 5,197,979 A | 3/1993 | Quintero et al. |
| 5,290,300 A | 3/1994 | Cosgrove et al. |
| 5,443,502 A | 8/1995 | Caudillo et al. |
| 5,476,510 A | 12/1995 | Eberhardt et al. |
| 5,480,425 A | 1/1996 | Ogilive |
| 5,531,785 A | 7/1996 | Love et al. |
| 5,578,076 A | 11/1996 | Krueger et al. |
| 5,582,607 A | 12/1996 | Lackman |
| 5,628,789 A | 5/1997 | Vanney et al. |
| 5,713,952 A | 2/1998 | Vanney et al. |
| 5,735,842 A | 4/1998 | Krueger et al. |
| 5,807,405 A | 9/1998 | Vanney et al. |
| 6,409,758 B2 | 6/2002 | Stobie et al. |
| 6,966,925 B2 | 11/2005 | Stobie |
| 7,018,407 B1 | 3/2006 | Wright et al. |
| 7,658,763 B2 | 2/2010 | Stobie |
| 7,819,915 B2 * | 10/2010 | Stobie .................. A61F 2/2427 623/2.11 |
| 8,029,564 B2 | 10/2011 | Johnson et al. |
| 8,057,538 B2 | 11/2011 | Bergin et al. |
| 8,454,684 B2 | 6/2013 | Bergin et al. |
| 9,078,750 B2 | 7/2015 | Carpentier et al. |
| 9,289,293 B2 | 3/2016 | Murad et al. |
| 9,333,076 B1 | 5/2016 | Edquist et al. |
| 9,693,862 B2 | 7/2017 | Campbell et al. |
| 9,861,478 B2 * | 1/2018 | Murad .................. A61F 2/2427 |
| 10,786,352 B2 | 9/2020 | Francis et al. |
| 2003/0125805 A1 | 7/2003 | Johnson et al. |
| 2004/0024451 A1 | 2/2004 | Johnson et al. |
| 2004/0148017 A1 | 7/2004 | Stobie |
| 2007/0244551 A1 | 10/2007 | Stobie |
| 2013/0289699 A1 | 10/2013 | Green et al. |
| 2014/0039609 A1 | 2/2014 | Campbell et al. |
| 2014/0257468 A1 | 9/2014 | Li |
| 2016/0324451 A1 | 11/2016 | Young |
| 2019/0125525 A1 | 5/2019 | Bennett et al. |

FOREIGN PATENT DOCUMENTS

| | | |
|---|---|---|
| WO | 2014/022300 A1 | 2/2014 |
| WO | 2019/089387 A1 | 5/2019 |

OTHER PUBLICATIONS

International Preliminary Report on Patentability received for PCT Patent Application No. PCT/US2018/057796, dated May 14, 2020, 12 pages.

\* cited by examiner

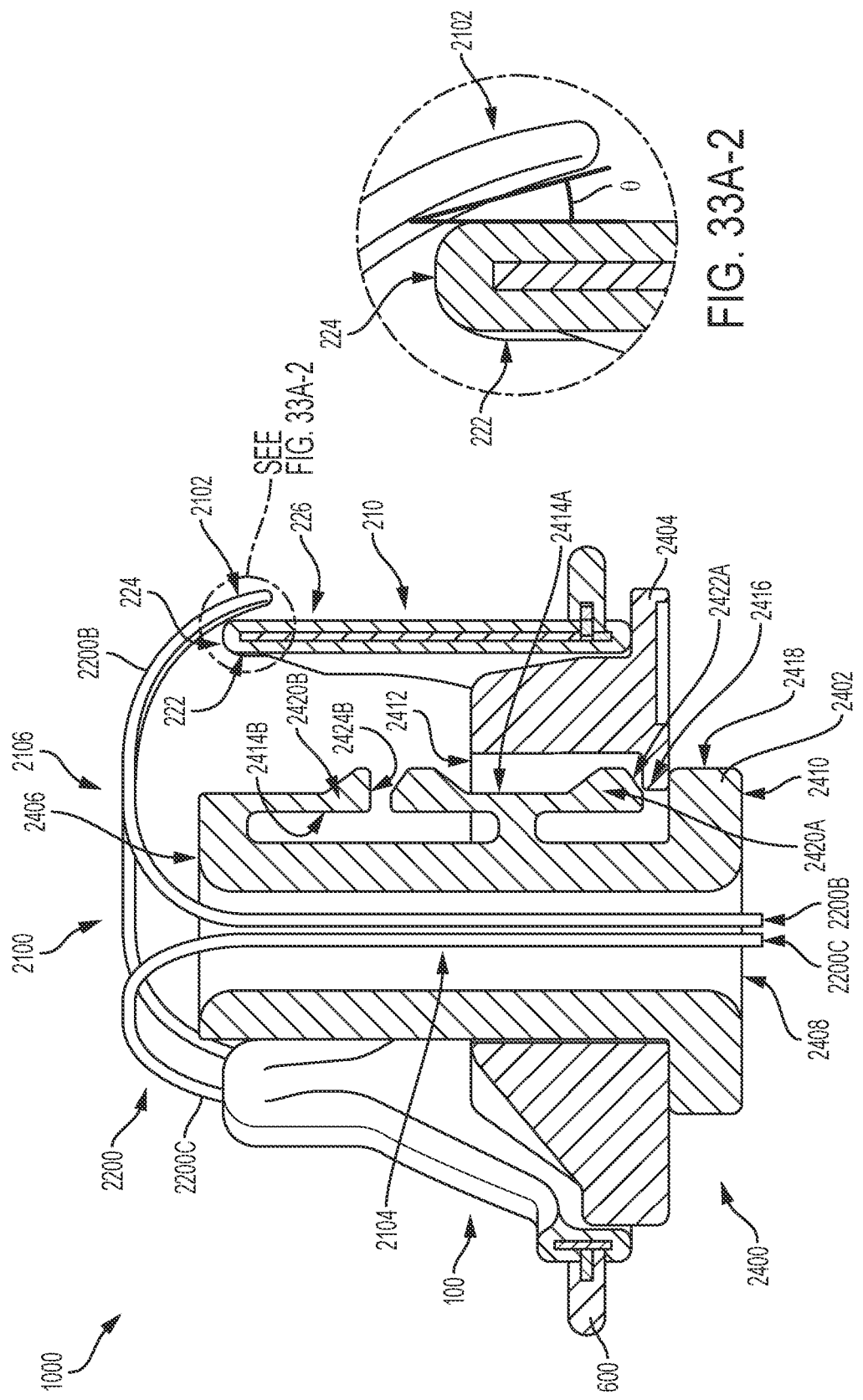

SUTURE GUARD FOR A PROSTHETIC VALVE

CROSS-REFERENCE TO RELATED APPLICATION

This application is a continuation of U.S. application Ser. No. 16/170,795, filed Oct. 25, 2018, which claims the benefit of Provisional Application No. 62/579,761, filed Oct. 31, 2017, which are incorporated herein by reference in their entireties for all purposes.

FIELD

The present disclosure relates generally to prosthetic valves and more specifically suture guards and holders for flexible leaflet-type prosthetic heart valve devices.

BACKGROUND

Prosthetic heart valves have been developed that attempt to mimic the function and performance of a native valve. Prosthetic valves with flexible leaflets typically require some means for securing the leaflets to a support structure, such as a leaflet frame. Leaflet(s) may be secured to the frame, for example, by suturing or adhesive/thermal bonding. In addition, the prosthetic valve is typically attached to a human heart with sutures, through a sewing cuff arranged with the frame, or some other mechanical attachment means (e.g., staples).

Prosthetic heart valve delivery may be difficult due to various aspects of the prosthetic valve and the anatomy to which the prosthetic valve is inserted. Accordingly, it would be desirable to ease implantation and protect the prosthetic valve during delivery of the prosthetic valve and attachment of the prosthetic valve to the heart.

SUMMARY

According to one example ("Example 1"), a system includes a heart valve including a first commissure post, and a delivery apparatus coupled to the heart valve, wherein the delivery apparatus includes a base including an inflow end and an outflow end, the outflow end being distal to the inflow end, and a suture guard that is selectively deployable and that extends through the base, the suture guard configured to transition from initial configuration to a deployed configuration, wherein in the initial configuration the suture guard is in a collapsed configuration such that the suture guard is situated radially inwardly of an interior surface of an outflow end of the first commissure post, and wherein in the deployed configuration the suture guard extends radially outwardly of the interior surface of the outflow end distal to the outflow end of the first commissure post.

According to another example ("Example 2") further to Example 1, the suture guard includes a frame element that is shape set such that when the suture guard is transitioned to the deployed configuration the frame element is configured to cause the suture guard to naturally adopt the deployed configuration.

According to another example ("Example 3") further to Example 2, frame element is defined by a first strut and a second strut, the first and second struts being configured to separate from one another as the suture guard is transitioned to the deployed configuration due to the shape set of the frame element such that the first strut extends radially outwardly of the interior surface of the outflow distal to the outflow end of the first commissure post, and such that the second strut extends radially outwardly of an interior surface of an outflow end of a second commissure post and distally of the outflow end of the second commissure post.

According to another example ("Example 4") further to Example 3, the first strut defines a first looped portion of the frame element and the second strut defines a second looped portion of the frame element, and wherein a bend region defines a transition between the first looped portion and the second looped portion, wherein an angle of the bend region in the deployed configuration is greater than an angle of the bend region in the initial configuration.

According to another example ("Example 5") further to Example 4, the bend region stores potential energy in the initial configuration that is convertible to kinetic energy to cause the frame element to adopt the deployed configuration.

According to another example ("Example 6") further any of Examples 2 to 5, the first and second struts are the same strut.

According to another example ("Example 7") further to any of Examples 4 to 6, the first and second looped portions collectively define a first frame element, the suture guard including a second frame element substantially similar to the first frame element and angularly offset relative to the first frame element such that the first looped portion of the first frame element is adjacent a second looped portion of the second frame element, wherein the first looped portion of the first frame element and the second looped portion of the second frame element collectively define a first petal of the suture guard, and wherein the first petal of the suture guard is configured to extend radially outwardly of the interior surface of the outflow distal to the outflow end of the first commissure post in the deployed state.

According to another example ("Example 8") further to any of Examples 4 to 7, the first looped portion of the first frame element and the second looped portion of the second frame element are coupled together by a biocompatible film.

According to another example ("Example 9") further to Example 8, the biocompatible film includes a polymer.

According to another example ("Example 10") further to Example 8, the polymer includes ePTFE.

According to another example ("Example 11") further to any of Examples 4 to 10, the suture guard includes a same number of petals as the heart valve includes commissure posts.

According to another example ("Example 12") further to any of Examples 7 to 11, the suture guard includes a third frame element substantially similar to the first and second frame elements and angularly offset relative thereto such that the suture guard includes three petals.

According to another example ("Example 13") further to any of the preceding Examples, when in the initial configuration the suture guard is in a non-everted configuration, and when in the deployed configuration the suture guard is everted such that a portion of the suture guard that extends radially outwardly of the interior surface of the outflow end of the first commissure post extends toward the inflow end of the base.

According to another example ("Example 14") further to any of the preceding Examples, the suture guard is advanceable relative to the base to cause the suture guard to transition to the deployed configuration, and wherein the suture guard is retractable relative to the base to cause the suture guard to transition to the initial configuration.

According to another example ("Example 15") further to any of the preceding Examples, when in the initial configuration an outflow end of the first commissure post is exposed, and when in the deployed configuration the suture guard covers the outflow end of the first commissure post.

According to another example ("Example 16") further to any of the preceding Examples, the frame element includes nitinol or a shape memory polymer According to another example ("Example 17") further to any of the preceding Examples, the suture guard is configured to deflect suture line from becoming entangled with the first commissure post.

According to another example ("Example 18") further to any of the preceding Examples, the suture guard is configured to deflect suture line from becoming looped around the first commissure post.

According to another example ("Example 19") further to any of the preceding Examples, the delivery apparatus further includes a shaft extending through the base, the shaft including an inflow end and an outflow end, and the suture guard extending through a lumen of the shaft, wherein an application of linear motion of the shaft in the outflow direction relative to the base causes the suture guard to transition to the deployed configuration.

According to another example ("Example 20") further to Example 19, with the suture guard in the deployed configuration, an application of linear motion of the shaft in the inflow direction relative to the base causes the suture guard to transition to the initial configuration.

According to another example ("Example 21") further to any of the preceding Examples, the system further includes a delivery handle configured to control the transition of the suture guard between the initial and deployed configurations.

According to another example ("Example 22") a delivery apparatus for a prosthetic valve includes a base configured to engage the prosthetic valve, the base including an inflow end and an outflow end, the outflow end being more distal than the inflow end, and a suture guard configured to transition from initial configuration to a deployed configuration, the suture guard including an end and an intermediate portion, wherein in the initial configuration the suture guard is collapsed within the base in a non-everted configuration such that the end is distal to the intermediate portion, and wherein in the deployed configuration the suture guard is deployed from the outflow end of the base such that a portion of the suture guard is everted such that the end extends toward the inflow end of the base proximal to the intermediate region, wherein the suture guard is configured to deflect suture line from becoming entangled with a first commissure post of the prosthetic valve during an implantation procedure.

According to another example ("Example 23") a delivery apparatus for a prosthetic valve includes a base configured to engage the prosthetic valve, the base including an inflow end and an outflow end, and a suture guard, the suture guard extending through the base and including an end that is configured to extend from the outflow end of the base, the suture guard further configured to evert such that the end of the suture guard extends toward the inflow end of the base, wherein the suture guard is configured to deflect suture line from becoming entangled with a first commissure post of the prosthetic valve during an implantation procedure.

According to another example ("Example 24") a method of delivering a prosthetic valve including a first commissure post includes providing a delivery apparatus secured to the prosthetic valve, the delivery apparatus including a base including an inflow end and an outflow end, the outflow end being distal to the inflow end, and a suture guard that is selectively deployable and that extends through the base, the suture guard being situated radially inwardly of an interior surface of an outflow end of the first commissure post, and advancing the suture guard relative to the base such that the suture guard extends radially outwardly of the interior surface of the outflow end distal to the outflow end of the first commissure post to deflect suture line from looping around the first commissure post.

According to another example ("Example 25") further to Example 24, the method further includes retracting the suture guard relative to the base such that the suture guard is withdrawn into an interior of the base such that the suture guard is in a collapsed and non-everted configuration.

According to another example ("Example 26") a delivery apparatus for a prosthetic valve includes a suture guard configured to move one or more valve posts of the prosthetic valve inwardly toward a longitudinal axis of the prosthetic valve upon application of a linear motion to shorten a length of the suture guard.

According to another example ("Example 27") further to Example 26, the suture guard is configured to protect at least one of the valve posts and one or more leaflets of the prosthetic valve from becoming entangled with sutures during implantation of the prosthetic valve to a target location.

According to another example ("Example 28") further to any of Examples 26-27, the suture guard includes one or more fiber lines arranged between the one or more valve posts.

According to another example ("Example 29") further to Example 28, upon application of linear motion the one or more fiber lines are configured to apply tension to move one or more valve posts of the prosthetic valve inwardly toward a longitudinal axis of the prosthetic valve.

According to another example ("Example 30") further to Example 29, the suture guard includes a linear motion mechanism configured to apply the tension to the one or more fiber lines and withdraws the one or more fiber lines inwardly toward the suture guard.

According to another example ("Example 31") further to any of Examples 28-30, the suture guard includes an upper portion and a lower portion, and the lower portion is configured to interface with the prosthetic valve, and the lower portion is configured to apply the tension to the one or more fiber lines.

According to another example ("Example 32") further to any of Examples 26-31, the apparatus further includes an atraumatic dome arranged with an outflow portion of the prosthetic valve and configured to protect against injury to a portion of a heart and to create a ramp for sutures to slide over and past the commissure posts.

According to another example ("Example 33") further to Example 26, the suture guard includes an everted tube configured to cover the valve posts and move the one or more valve posts of the prosthetic valve inwardly toward a longitudinal axis of the prosthetic valve.

According to another example ("Example 34") further to Example 26, the suture guard includes one or more arms configured to bend the one or more valve posts of the prosthetic valve inwardly toward a longitudinal axis of the prosthetic valve According to another example ("Example 35") further to any of Examples 26-34, the suture guard is configured to protect valve during surgery, protect tissue during insertion, and prevent strut wrap.

According to another example ("Example 36") further to any of Example 36-35, the apparatus further includes a delivery handle configured to control the suture guard.

According to another example ("Example 37") further to Example 36, the handle is pre-attached to the suture guard for implantation of the prosthetic valve.

According to another example ("Example 38") further to any of Examples 36-37, upon application of linear motion, the one or more fiber lines are configured to apply tension to move the one or more valve posts of the prosthetic valve inwardly toward a longitudinal axis of the prosthetic valve, and further including a release fiber coupled to the handle and configured to releasably lock the one or more fiber lines with the suture guard, and wherein a portion of the handle is configured to actuate and release the release fiber to unlock the one or more fiber lines.

The foregoing Examples are just that, and should not be read to limit or otherwise narrow the scope of any of the inventive concepts otherwise provided by the instant disclosure.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 33A-1 is a cross-sectional view of the example suture guard shown in the deployed configuration in FIG. 29B, taken along line 33-33, in accordance with an embodiment;

FIG. 33A-2 is a detail view of a portion of FIG. 33A-1, showing a portion of the suture guard overlapping a portion of a valve frame, as indicated.

DETAILED DESCRIPTION

Figure 1B:
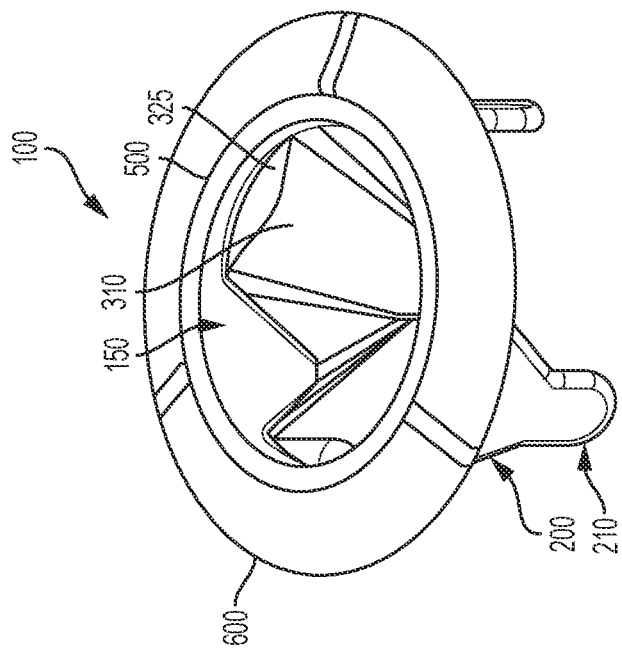
FIG. 1B is an inflow side perspective view of the embodiment of the valve of FIG. 1A.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

Aspects of the present disclosure are directed toward heart suture guards. The heart suture guards are configured to facilitate implantation of the heart valve. The heart suture guards discussed herein facilitate placement and suturing of the heart valve into the native annulus, and, in certain embodiments, help prevent damage to the heart valve from mishandling of the heart valve during an implantation procedure. For example, the heart suture guards (also referred to herein as suture guards) discussed herein are configured to help prevent sutures from looping over or otherwise becoming entangled with the valve posts (also referred to herein as suture looping, shunt wrapping, and/or strut wrapping) during implantation. When suture is inadvertently looped around one or more valve posts and subsequently tightened, the looped suture can damage one or more portions of the valve structure, damage one or more valve leaflets, negatively impact the functionality of the valve and/or the leaflets inside the posts. The heart suture guard designs, consistent with various aspects of the present disclosure, are configured to lessen the opportunity for suture looping.

In some embodiments, the suture guards are configured to engage the valve posts to deflect the valve posts radially inward toward a longitudinal axis of the prosthetic valve 100. In some examples, this mechanism of deflecting the valve posts radially inward helps prepare the valve for insertion into the annulus. Moreover, in some examples, a deflection of the valve posts radially inward helps reduce a radial profile of the valve posts, which help reduce the likelihood of a suture becoming entangled with the valve post. In various embodiments, the suture guard may also operate to cover or at least extend over an outflow end of the valve post, as illustrated and described below. A suture guard that extends over an outflow end of the valve post can operate to deflect suture line running along an exterior of the valve from migrating to a position interior to a valve post.

In some embodiments, the heart suture guards include ramping features that are configured to deflect suture away from the valve posts. In some examples, the suture guards help the suture land safely on a suture ring or sewing cuff on the prosthetic valve without getting entangled with the valve posts.

Figure 1A:
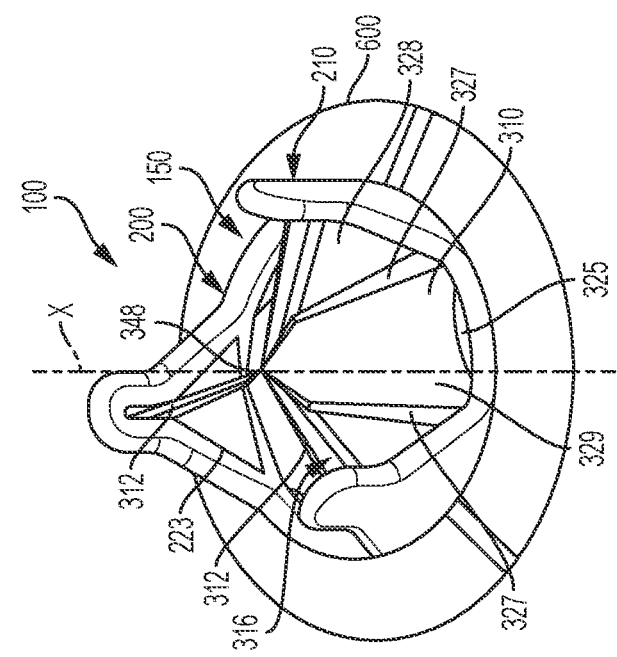
FIG. 1A is an outflow side perspective view of an example prosthetic heart valve in accordance with an embodiment.

FIGS. 1A and 1B are outflow and inflow, respectfully, perspective views of a valve 100 in the form of a prosthetic heart valve, in accordance with an embodiment. The components of the valve 100 that are visible in FIGS. 1A and 1B include three flexible leaflets 310, a leaflet frame 200 including three valve (commissure) posts 210 that has been covered with material, a base frame 500 that has been covered with material, and a sewing cuff 600. The leaflet free edges 312 of the leaflets 310 come together at a coaptation region 316 in a Y-shaped pattern (when viewed from above) to close the valve 100. The valve 100 closes in this fashion when the pressure of the blood on the outflow side (as viewed in FIG. 1A) is greater than the pressure of the blood on the inflow side of the valve (as viewed in FIG. 1B). The leaflet free edges 312 of the leaflets 310 move apart to open the valve 100 and to let blood flow through the valve 100 from the inflow side as viewed in FIG. 1B when the pressure of the blood on the inflow side of the valve 100 is greater than the pressure on the outflow side of the valve 100. For purposes of this disclosure, it is to be understood that the inflow side or end of the heart valve 100 is considered "proximal" to the outflow side or end of the heart valve 100, while the outflow side or end of the heart valve 100 is considered "distal" to the inflow side or end of the heart valve 100.

The leaflets 310 generally flex about the leaflet base 325 of the U-shaped portion as the leaflets 310 open and close. In an embodiment, when the valve 100 is closed, generally about half of each leaflet free edge 312 abuts an adjacent half of a leaflet free edge 312 of an adjacent leaflet 310, as shown in FIG. 1A. The three leaflets 310 of the embodiment of FIG. 1A meet at a triple point 348. The valve orifice 150 is occluded when the leaflets 310 are in the closed position stopping fluid flow during reverse flow.

In accordance with other embodiments of the valve 100, each leaflet 310 includes a central region 329 and two side regions 328 on opposite sides of the central region 329. The central region 329 is defined by a shape substantially that of an isosceles trapezoid defined by two central region sides 327, the leaflet base 325 and the leaflet free edge 312. Each of the side regions 328 has a shape substantially that of a triangle and each are defined by one of the central region sides 327, one of the leaflet sides 323, and the leaflet free edge 312.

Figure 2A:
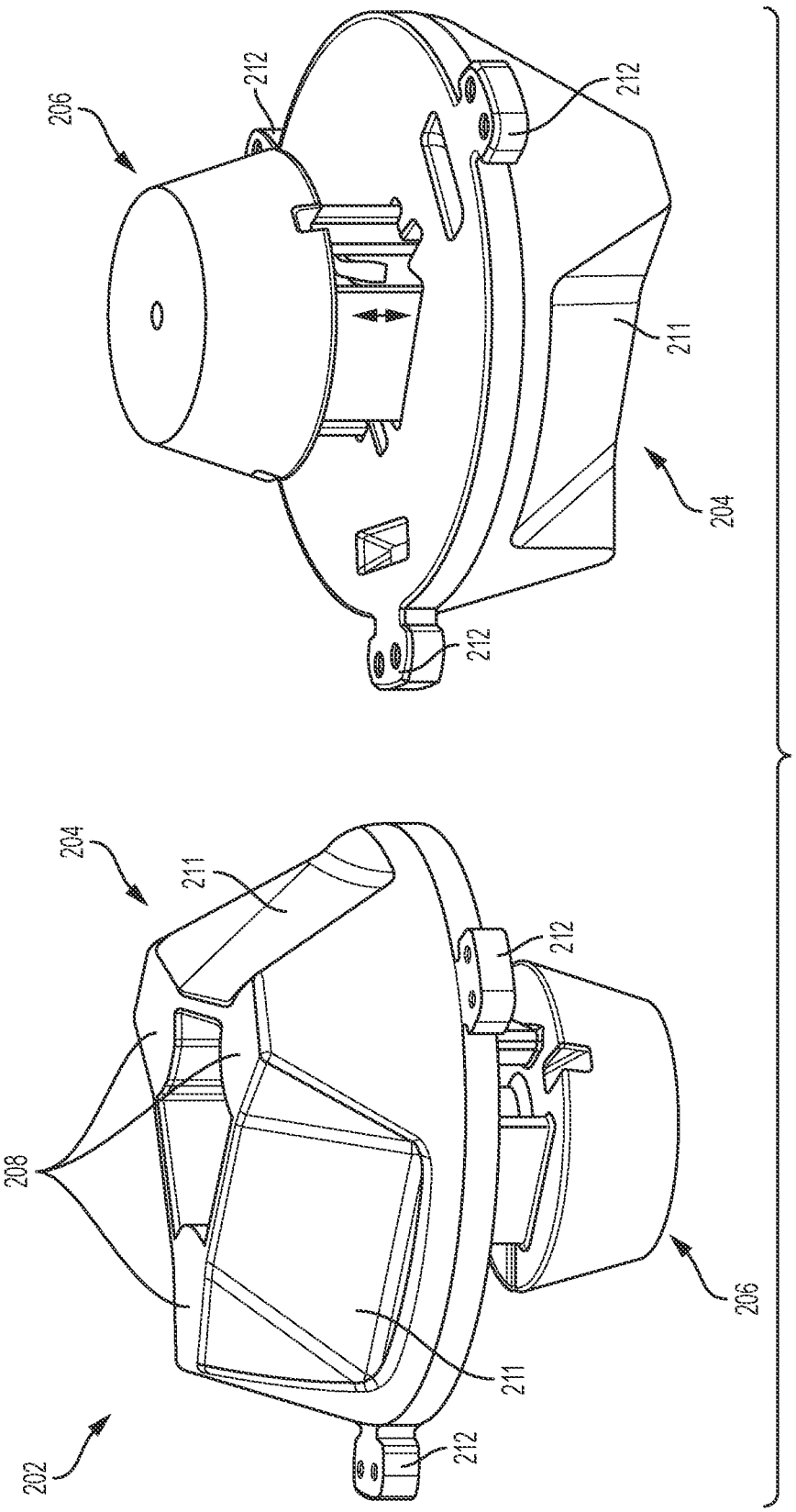
FIG. 2A is a perspective top and bottom views of an example suture guard in accordance with an embodiment.

FIG. 2A is a side-by-side illustration of a suture guard 202 in accordance with an embodiment. The suture guard 202 includes a first (upper) portion 204 and a second (lower) portion 206. The first portion 204 is configured to interface with a prosthetic heart valve 100 (as shown in further detail in FIGS. 2B-G). The first portion 204 includes supports 208 that may be equal to a number of valve (commissure) posts 210, shown in FIGS. 1A-B. The supports 208 may interface with an internal portion of the valve (commissure) posts 210. As described in further detail below, the supports 208 act as a surface to structurally support the valve (commissure) posts 210 when moved inwardly for delivery. More specifically, the suture guard 202 is configured to move, which may be by bending, one or more valve (commissure) posts 210 of the prosthetic valve 100 inwardly toward a longitudinal axis of the prosthetic valve 100.

In addition, the first portion 204 may also include tapered surfaces 211 that are carved out of the first portion 204 to avoid interference with the leaflets 310. The first portion 204 may be arranged within an inflow side of the valve 100. The first portion 204 of the suture guard 202 also includes fiber holding portions 212 that are arranged at a perimeter of the first portion 204 of the suture guard 202. The fiber holding portions 212 include openings that a suture or fiber may be thread through in order to move the one or more valve (commissure) posts 210 of the prosthetic valve 100 inwardly toward a longitudinal axis of the prosthetic valve 100.

The second portion 206 of the suture guard 202 is arranged below or under the first portion 204. The second portion 206 may be configured to apply the force used to move the one or more valve (commissure) posts 210 of the prosthetic valve 100 inwardly toward a longitudinal axis of the prosthetic valve 100. The second portion 206, for example, can apply tension via a linear motion to the fiber or suture. The second portion 206 withdraws the one or more fiber lines inwardly toward the second portion 206 of the suture guard 202 to move the one or more valve (commissure) posts 210. In addition, this mechanism shortens the length of the suture guard 202 and the one or more valve (commissure) posts 210 as opposed to lengthening the assembly. As shown in detail with reference to FIGS. 2C-G, the second portion 206 may interface with a suture or fiber such that the suture or fiber slides inside the second portion 206, which pulls the suture or fiber. This action by the second portion 206 applies the force used to move the one or more valve (commissure) posts 210 of the prosthetic valve 100 inwardly toward a longitudinal axis of the prosthetic valve 100.

Figure 2B:
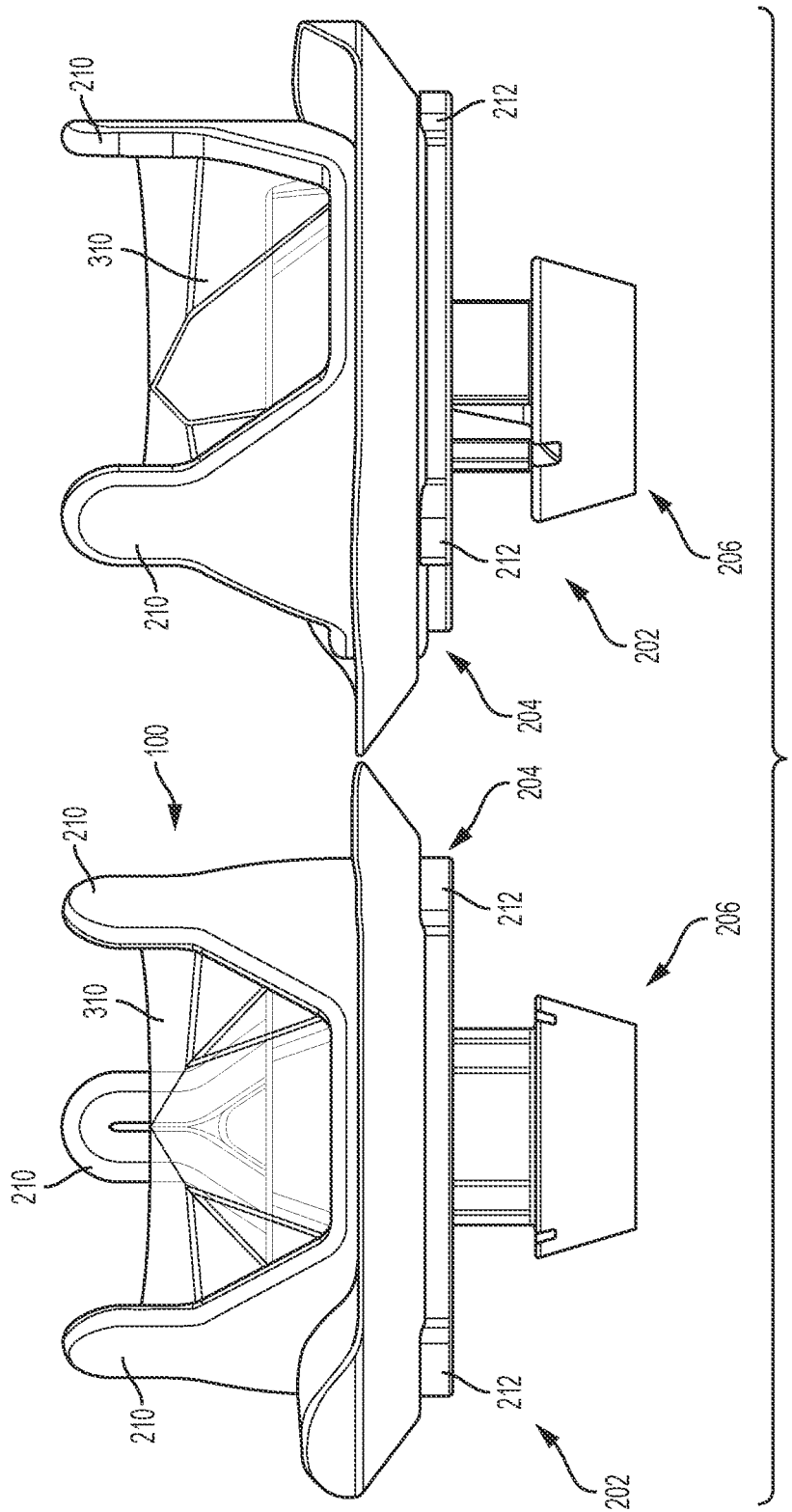
FIG. 2B is a first and second side view of the suture guard, shown in FIG. 2A, with a prosthetic heart valve.

FIG. 2B is a first and second side view of the suture guard 202, shown in FIG. 2A, with a prosthetic heart valve 100. The suture guard 202 is shown with the prosthetic heart valve 100. The suture guard 202 does not alter the shape or otherwise move the prosthetic heart valve 100 at this point. The suture guard 202 is arranged within the inflow portion of the prosthetic heart valve 100 and may support the leaflets 310 during implantation.

The suture guard 202 is shown in an initial (e.g., not tensioned) position. The suture guard 202 has not applied to tension to or otherwise altered the shape of the prosthetic heart valve 100 in the position shown in FIG. 2B. To connect the first portion 204 and the second portion 206, the second portion 206 is pressed into the first portion 204. In certain embodiments, the second portion 206 connects by using a click-tight mechanism or pawl mechanism. The second portion 206 connects with the first portion 204 with one click, in certain embodiments.

To align the suture guard 202 with the prosthetic valve 100, the fiber holding portions 212 (or tabs) are aligned with the valve (commissure) posts 210. The fiber holding portions 212 may be seated against the base of the prosthetic valve 100, which may be facilitated by the tapered surfaces 211 of the first portion 204 of the suture guard 202.

Figure 2C:
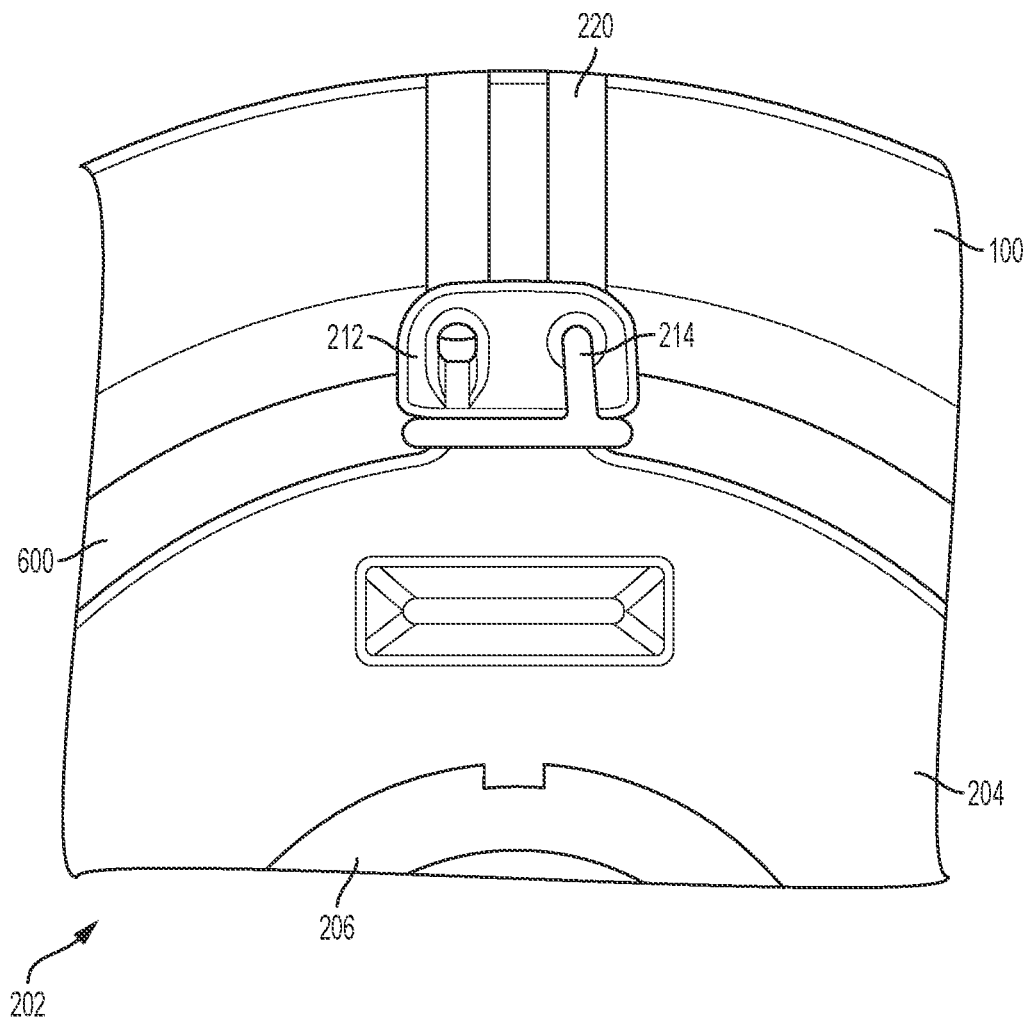
FIG. 2C is a bottom view of the suture guard and the prosthetic heart valve, shown in FIGS. 2A-B, with a fiber.

FIG. 2C is a bottom view of the suture guard 202 and the prosthetic heart valve 100, shown in FIGS. 2A-B, with a fiber 214. One end of the fiber 214 is wrapped through openings in the fiber holding portion 212. The fiber 214 may be knotted at the through openings in the fiber holding portion 212 to tie the fiber 214 to the suture guard 202. In certain embodiments, another fiber 214 is similarly routed through each of the fiber holding portions 212. In other embodiments, a single fiber 214 is used. In certain embodiments, the fiber holding portions 212 are equal to the number of supports 208 in the first portion 204 of the suture guard 202, which may be equal to a number of valve (commissure) posts 210. The other end of the first fiber 214 is fed through the right hole in the fiber holding portions 212, and through a sewing cuff 600 of the prosthetic heart valve 100, in certain embodiments. The fibers 214 may be arranged from through a sewing cuff 600 to weave the fibers 214 between the inflow side and the outflow side of the prosthetic heart valve 100.

Figure 2D:
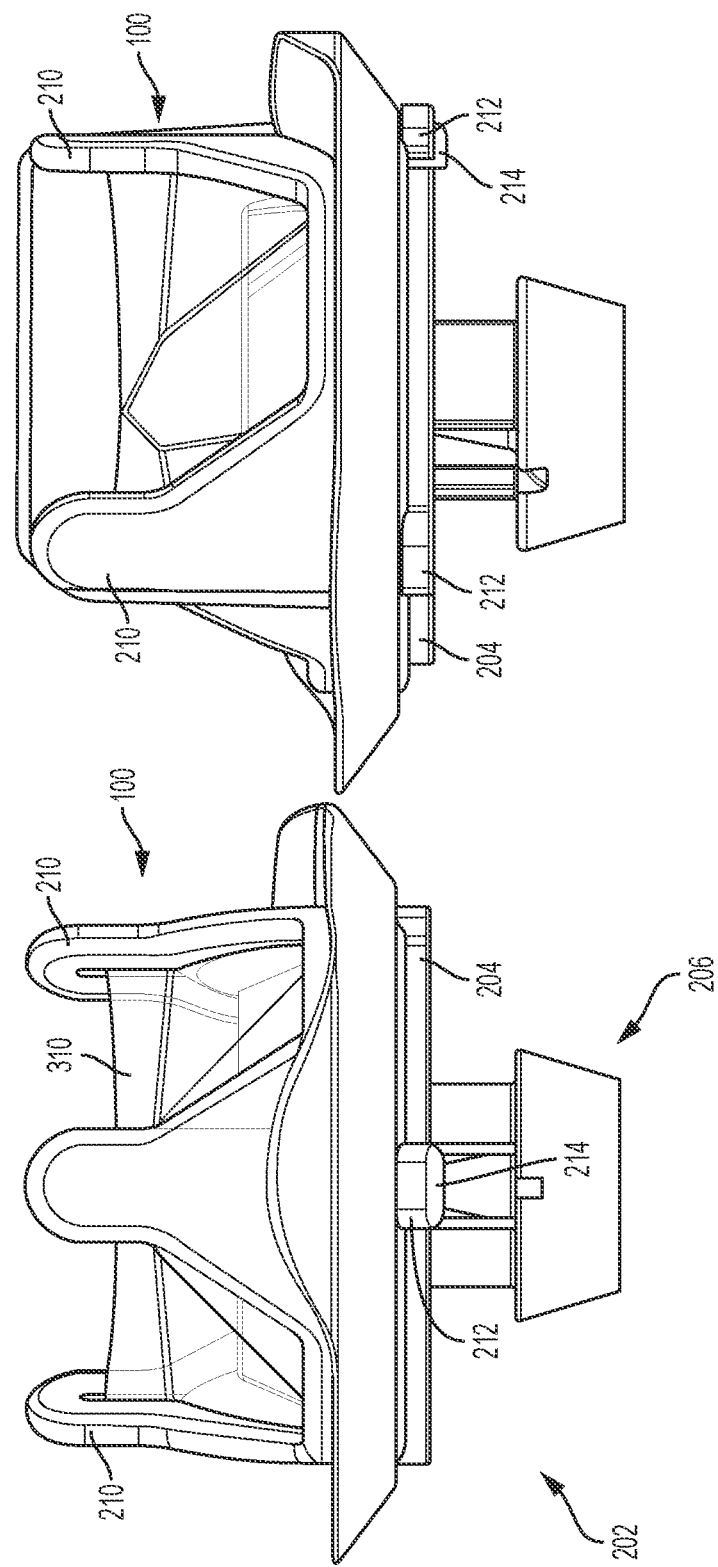
FIG. 2D is a first and second side view of the suture guard, the prosthetic heart valve, and the fiber, as shown in FIGS. 2A-C.

FIG. 2D is a first and second side view of the suture guard 202, the prosthetic heart valve 100, and the fiber 214, as shown in FIGS. 2A-C. After passing the fiber 214 through the sewing cuff (not shown), the fiber 214 is then passed through the valve (commissure) post 210. The fiber 214 is routed along a side of the valve (commissure) posts 210 (e.g., a right side of the valve (commissure) posts 210 as shown on the left portion of FIG. 2D). The fiber 214 remains on an outer diameter of the prosthetic heart valve 100 and does not pass through the inner diameter of the prosthetic heart valve 100 at any point. The fiber 214 is passed through the valve (commissure) posts 210 to the left (as shown right portion of FIG. 2D) and engages with the prosthetic heart valve 100 in the same manner as the other valve (commissure) posts 210 but mirrored.

Figure 2E:
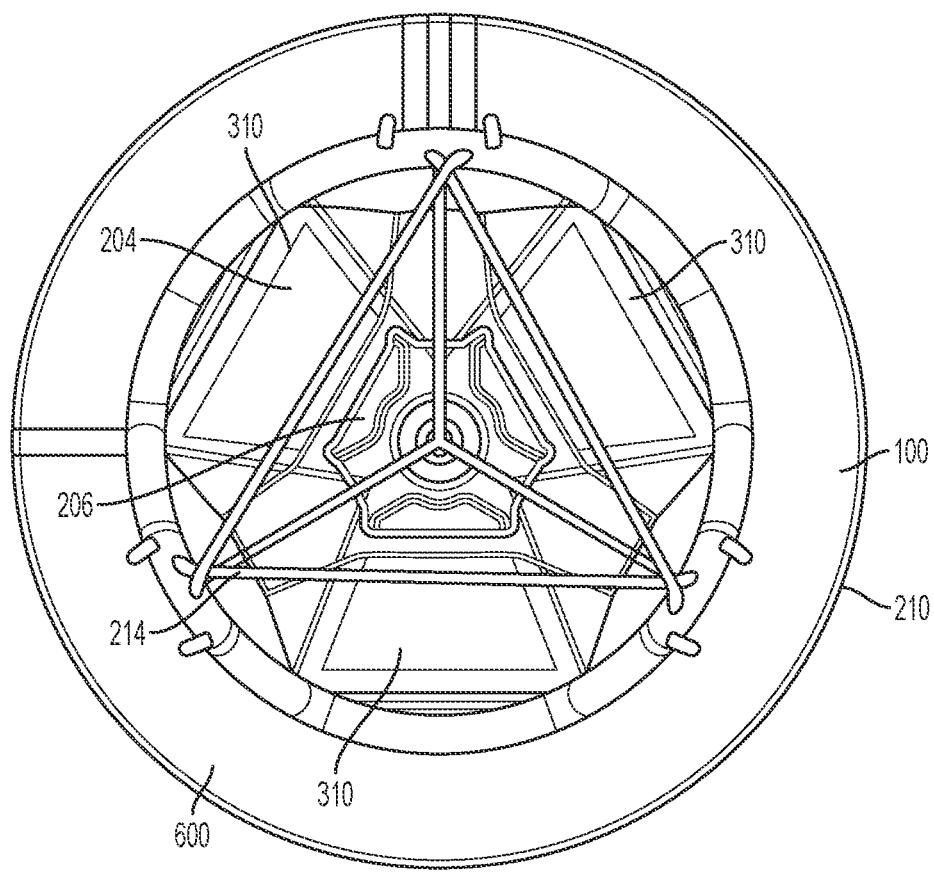
FIG. 2E is top view of the suture guard, the prosthetic heart valve, and the fiber, as shown in FIGS. 2A-D.

FIG. 2E is top view (from the outflow side) of the suture guard 202, the prosthetic heart valve 100, and the fiber 214, as shown in FIGS. 2A-D. After arranging the fiber 214 as described with reference to FIG. 2D, the fiber 214 may then be passed through the prosthetic heart valve 100 (e.g., through the sewing cuff) and through the left opening in the fiber holding portion 212. The other two fibers 214 are then fed through their respective openings in the fiber holding portions (obstructed in FIG. 2E) through the prosthetic heart valve 100 (e.g., through the sewing cuff), and through their respective valve (commissure) posts 210, as described with reference to the first fiber 214. In this embodiment, the three fibers 214 are fed through the prosthetic heart valve 100 and suture guard 202. The fibers 214 each span two valve (commissure) posts 210 with one end of the fibers 214 attached to the fiber holding portions 212 of the suture guard 202.

Although the prosthetic heart valve 100 is shown as a tricuspid valve (e.g., three leaflets 310), the prosthetic heart valve 100 may include any number of leaflets (e.g., one, two, four, five, six, and so on). In embodiments where the prosthetic heart valve 100 includes a different number of leaflets 310, the number of leaflets 310 may correspond to an equal number of aspects on the suture guard 202 such as an equal number of fibers 214, fiber holding portions 212, supports 208, and valve (commissure) posts 210.

Figure 2F:
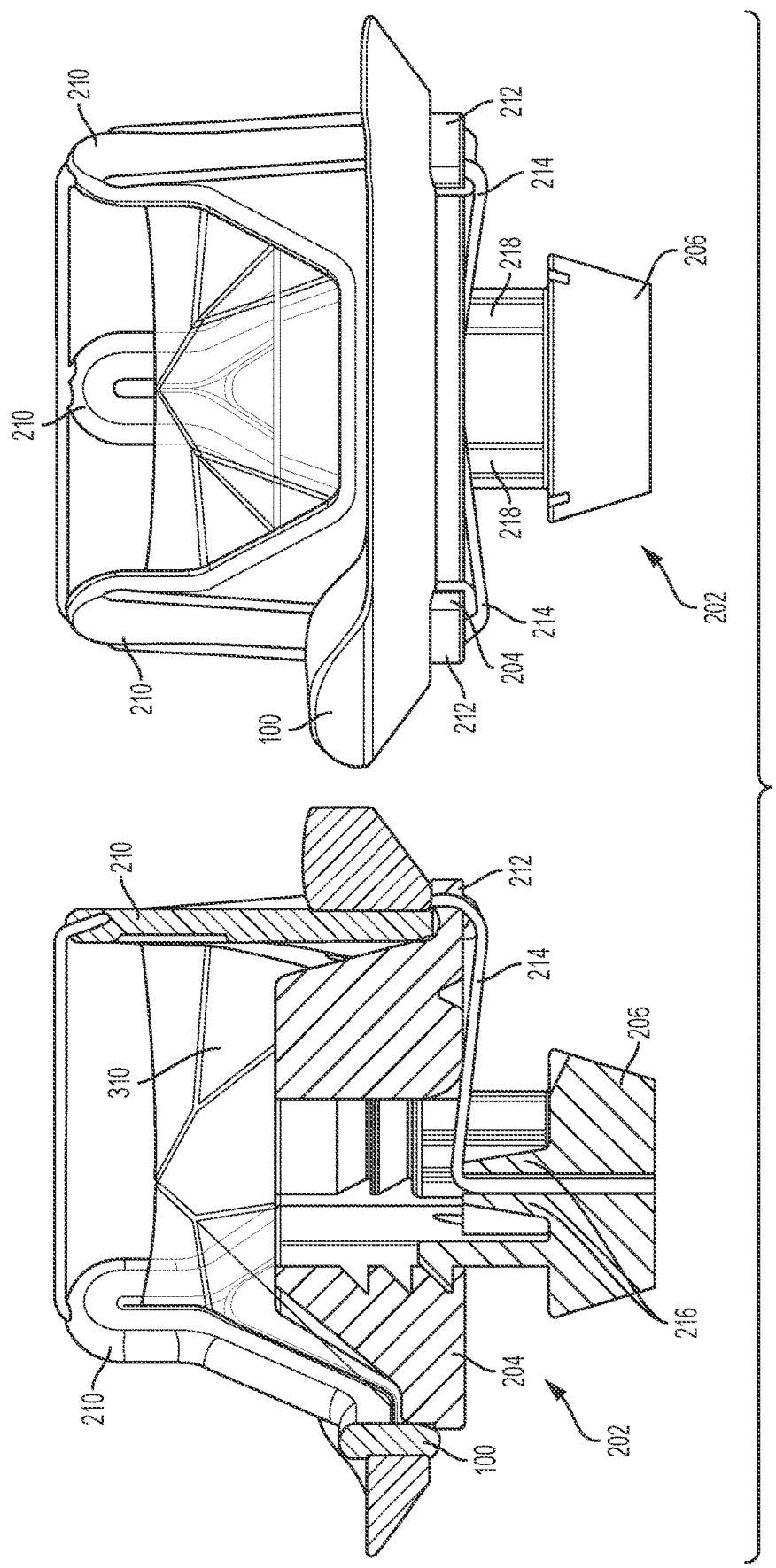
FIG. 2F is a partial cross-sectional first view and second side view of the suture guard, the prosthetic heart valve, and the fiber as shown in FIGS. 2A-E.

FIG. 2F is a partial cross-sectional first view and second side view of the suture guard 202, the prosthetic heart valve 100, and the fiber(s) 214 as shown in FIGS. 2A-E. The free end of each fiber 214 is then fed inside the suture guard 202. More specifically, the fiber 214 may be fed into the second portion 206 of the suture guard 202 between cone shaped members 216 of the second portion 206. The fibers 214 may enter the second portion through openings 218.

Figure 2G:
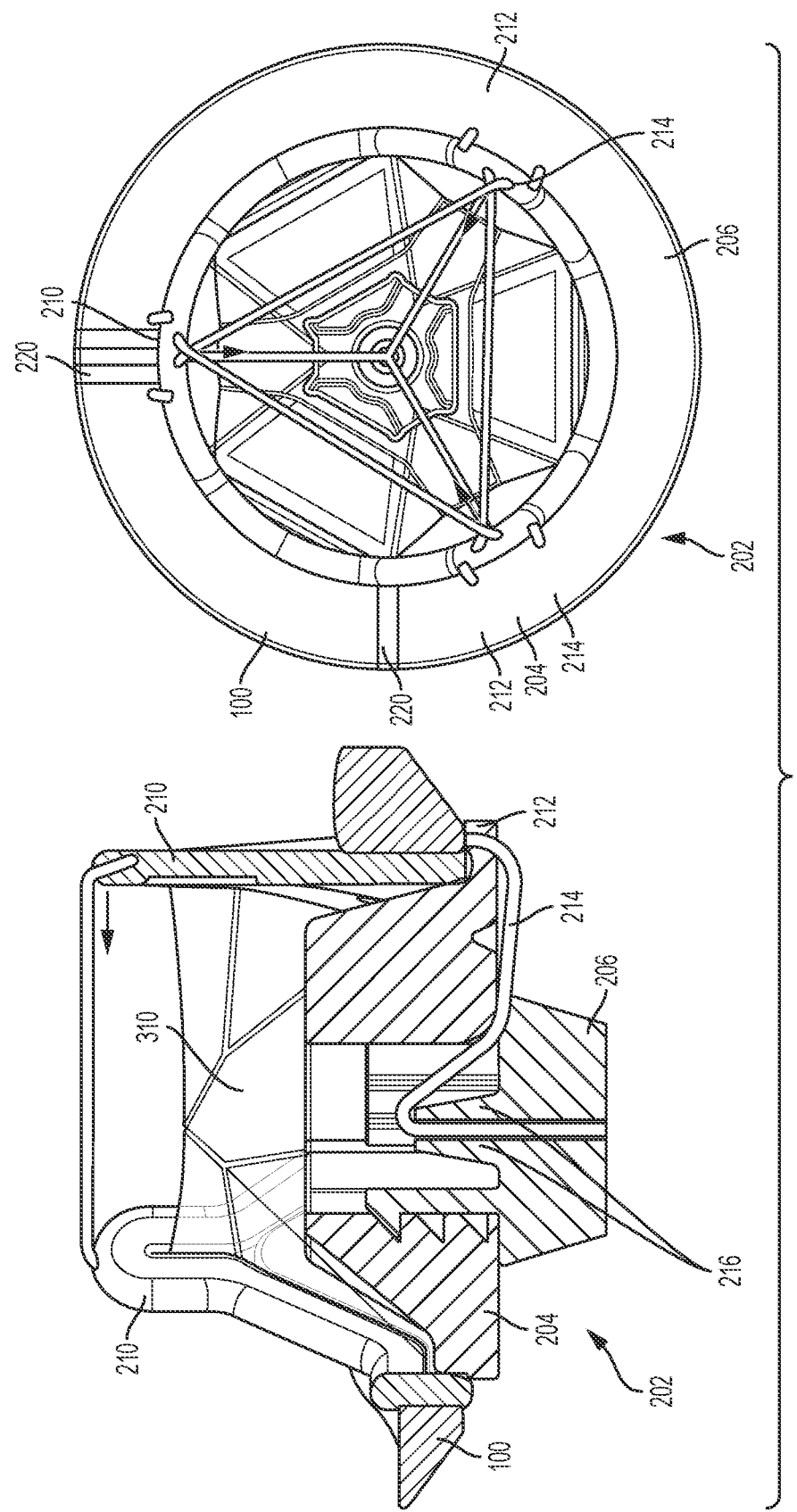
FIG. 2G is a partial cross-sectional first view and top view of the suture guard, the prosthetic heart valve, and the fiber as shown in FIGS. 2A-F.

As shown in FIG. 2F, the second portion 206 is shown engaged with the first portion 204 of the suture guard 202. As compared to FIG. 2G, the second portion 206 is outwardly extended from the first portion 204. The second portion 206 may be threadedly engaged or engaged via a snap-fit (click-fit or pawl mechanism) connection to the first portion 204. The second portion 206 is moved inwardly within the first portion 204 to adjust tension on the fibers 214 as shown in FIG. 2G. The prosthetic valve 100 and suture guard 202 are packaged together and delivered to a physician for implantation in the configuration shown in FIG. 2F. The physician engages the suture guard 202 by pressing (e.g., linearly actuating) the first portion 204 into the second portion 206, which in turn, tensions the fiber(s) 214 causing the valve (commissure) posts 210 to deflect inward preparing the prosthetic valve 100 for insertion into the annulus.

FIG. 2G is a partial cross-sectional first view and top view of the suture guard 202, the prosthetic heart valve 100, and the fiber(s) 214 as shown in FIGS. 2A-F. The prosthetic valve 100 and the suture guard 202 are shown in an engaged state for implantation. With all the fibers 214 secured to the second portion 206 (e.g., inside cone shaped members 216), the prosthetic heart valve 100 is ready for implantation (e.g., after packaging and sterilization). When a surgeon is ready to implant the prosthetic heart valve 100, a handle (e.g., as shown in FIGS. 4-5) is attached to the second portion 206, then the second portion 206 is pressed into the first portion 204 pulling the three fibers 214 with it as shown by the arrows in FIG. 2G. The length of the fibers 214 are fixed from end-to-end, thus, the tension resulting from pressing the second portion 206 into the first portion 204 (e.g., linear motion mechanism) deflects or moves, which may be by bending, the valve (commissure) posts 210 inwards. The fibers 214 may be arranged from through the sewing cuff 600 to weave the fibers 214 between the inflow side and the outflow side of the prosthetic heart valve 100.

To remove the suture guard 202, the surgeon cuts each of the three fibers 214 in a designated area 220 (e.g., a cut slot as also shown in FIG. 2C) which releases the tension in the fibers 214 allowing the valve (commissure) posts 210 held inward by the fibers 214 to return to the initial position when the suture guard 202 is released from the prosthetic valve 100. The suture guard 202 is removed from the prosthetic heart valve 100 by pulling the suture guard 202 out and away from the prosthetic heart valve 100. The handle may be removed prior to removing the suture guard 202 or the handle may be reattached to facilitate removal of the suture guard 202. As the ends of each of the fibers 214 remain attached to the suture guard 202 after being cut, the cut ends of each fiber 214 unwind back through the prosthetic heart valve 100 as the suture guard 202 is retracted away from the heart valve 100. Thus, removing the suture guard 202 also removes the fibers 214 from the prosthetic heart valve 100.

The suture guard 202 acts as a delivery tool to aide in the surgical process. As noted above, the suture guard 202 lessens the chance that sutures are entangled with for the valve (commissure) posts 210 and/or lessens the chance of suture wrapping around one or more of the leaflets 310 (shunt wrapping) during implantation of the prosthetic valve 100 at the target location. As discussed in detail above, the suture guard 202 is configured to ease of implantation, protect the anatomy, and prevent strut wrap.

Figure 3A:
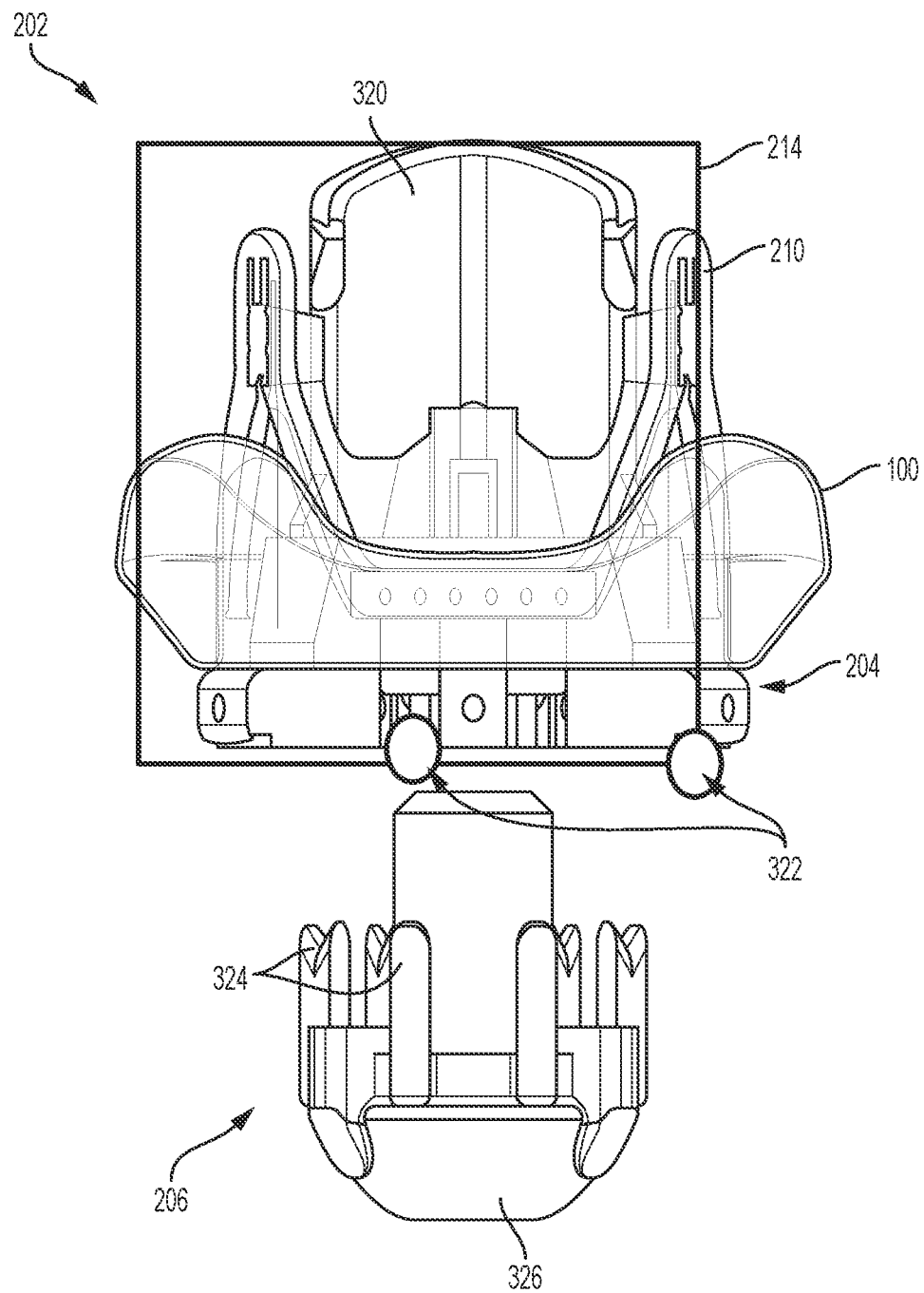
FIG. 3A is an exploded view of an example suture guard and a prosthetic heart valve, in accordance with an embodiment.

FIG. 3A is an exploded view of an example suture guard 202 and a prosthetic heart valve 100, in accordance with an embodiment. The suture guard 202 includes a first (upper) portion 204 and a second (lower) portion 206. The first portion 204 is configured to interface with a prosthetic heart valve 100, as shown in further detail in FIG. 3B. The suture guard 202 may also include an atraumatic dome 320. The atraumatic dome 320 interfaces with the first portion 204 of the suture guard 202. The first portion 204 may be arranged within the inflow section of the prosthetic heart valve 100 and the atraumatic dome 320 may be arranged within the outflow portion of the prosthetic heart valve 100. The atraumatic dome 320 is configured to protect against injury to a portion of a heart. In addition, the atraumatic dome 320 is configured to create a ramp for sutures (used to attach the prosthetic valve 100 at an implant location) to slide over and past the valve (commissure) posts 210 of the prosthetic valve 100 to avoid suture entanglement with one or more leaflets of the valve (commissure) posts 210.

As shown in FIG. 3A, the second portion 206 may be separable from the first portion 204. In addition, the suture guard 202 includes a fiber 214 routed through the suture guard 202. One end of the fiber 214 is routed through an opening in the first portion 204 (e.g., as shown above in FIGS. 2A-G). The fiber 214 may be defined by one or more knotted portions 322. In certain embodiments, the fiber 214 is routed through the valve (commissure) posts 210 of the prosthetic valve 100 as shown in FIG. 3A. The valve (commissure) posts 210 may include an opening.

The second portion 206 of the suture guard 202 is arranged below or under the first portion 204 of the suture guard 202. The second portion 206 may be configured to apply the force used to move the one or more valve (commissure) posts 210 of the prosthetic valve 100 inwardly toward a longitudinal axis of the prosthetic valve 100. The second portion 206, for example, can apply a linear motion to the fiber 214 or fibers 214. The second portion 206 withdraws the one or more fiber lines inwardly toward the second portion 206 of the suture guard 202 to move the one or more valve (commissure) posts 210. In addition, this mechanism shortens the length of the suture guard 202 and the one or more valve (commissure) posts 210 as opposed to lengthening the assembly.

As shown in FIG. 3A, the second portion 206 includes one or more prong structures 324 that interface with the first portion 204. The one or more prong structures 324 force the fiber 214 into the first portion 204. This action by the second portion 206 applies the tension to the fiber 214 as shown in further detail with reference to FIG. 3B.

The second portion 206 can include a screw mechanism 326 configured to secure the second portion 206 to the first portion 204. The screw mechanism 326 rotates relative to the second portion 206. The screw mechanism 326 may facilitate applying tension to the fiber 214 and maintaining tension on the fiber 214 during delivery and implantation of the prosthetic valve 100.

Figure 3B:
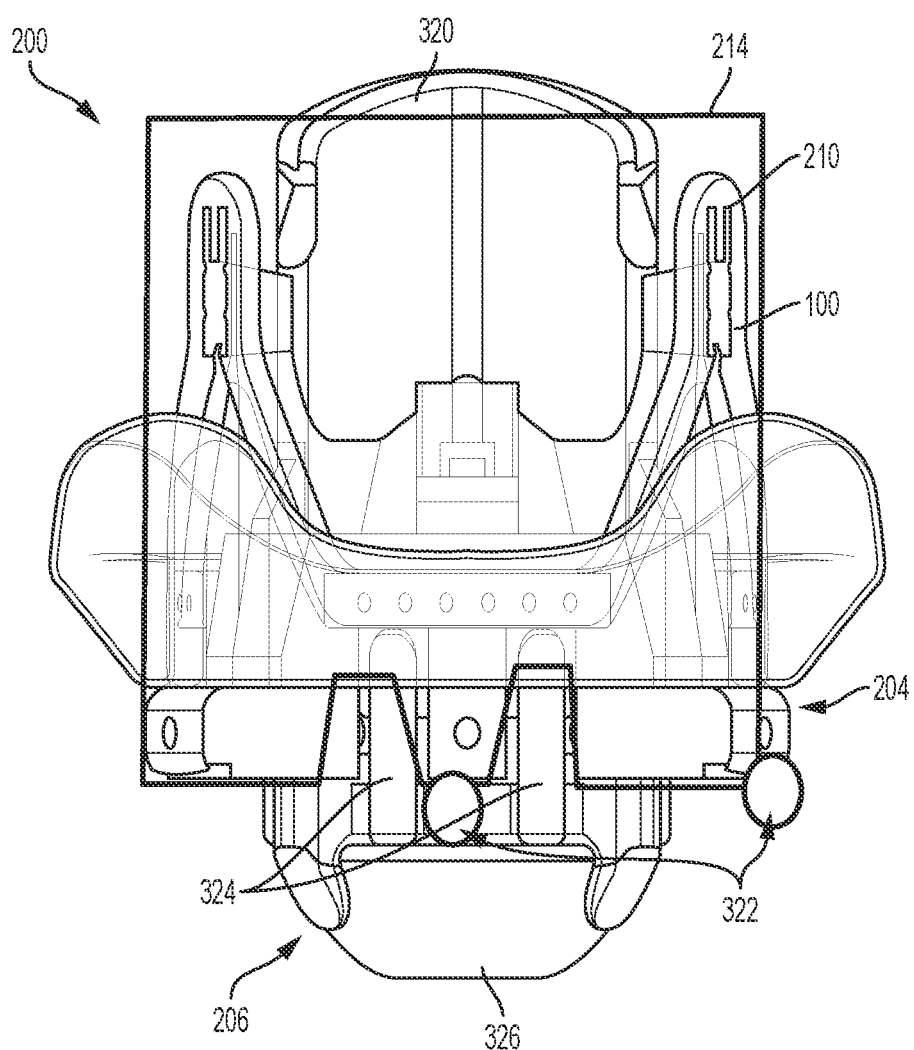
FIG. 3B is another view of the suture guard and the prosthetic heart valve, as shown in FIG. 3A.
Figure 3C:
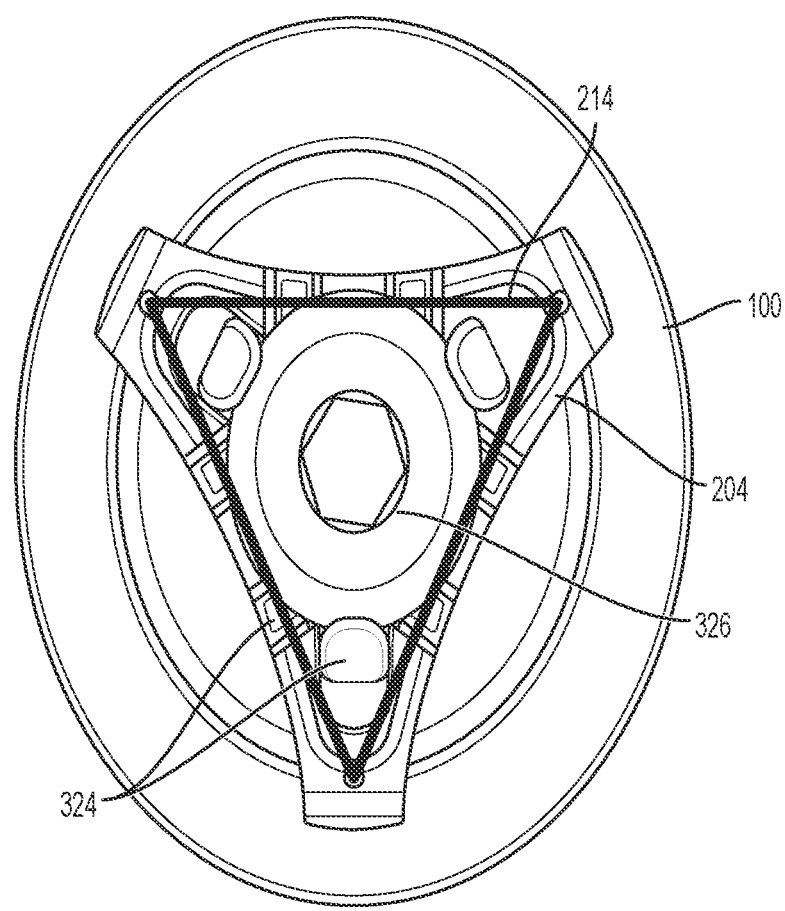
FIG. 3C is a bottom view of the suture guard and the prosthetic heart valve, as shown in FIGS. 3A-B.

FIG. 3B is another view of the suture guard 202 and the prosthetic heart valve 100, as shown in FIG. 3A with the second portion 206 coupled with the first portion, and with portions removed for ease of understanding. As shown in FIG. 3B, the prong structures 324 force the fiber 214 into the first portion 204 thereby applying tension to the fiber 214. The fiber 214 is crimped up into the first portion 204 by the prong structures 324. Because the fiber 214 is coupled to at least one of the one or more valve (commissure) posts 210 of the prosthetic valve 100, the tension moves the valve (commissure) posts 210 inwardly toward a longitudinal axis of the prosthetic valve 100.

In certain embodiments, the fiber 214 is secured to each of the valve (commissure) posts 210. In other embodiments, the suture guard 202 may include multiple fibers 214 (e.g., as described with reference to FIGS. 2A-G). When a surgeon is ready to implant the prosthetic heart valve 100, a handle (e.g., portions of which are shown in FIGS. 4-5) is attached to the second portion 206 at the screw mechanism 326. The handle may be used to actuate the screw mechanism 326 to apply tension to the fiber 214. The atraumatic dome 320 and the screw mechanism 326 can include oppositely threaded portion such that the screw mechanism 326 can fix the first portion 204 and the second portion 206 of the suture guard 202 together. In addition, the handle can include oppositely threaded portions relative to the screw mechanism 326 in order to tighten the screw mechanism 326 and tension the fiber 214.

To remove the suture guard 202, the surgeon cuts the fiber 214 in a designated area which releases the tension in the fiber 214 lines allowing the valve (commissure) posts 210 inwards to return to intended position. The suture guard 202 is removed from the prosthetic heart valve 100 by pulling the suture guard 202 out and away from the prosthetic heart valve 100. The handle may be removed prior to removing the suture guard 202, in other instances, the handle may be reattached to facilitate removal of the suture guard 202. FIG.

3C is a bottom view of the suture guard 202 and the prosthetic heart valve 100, as shown in FIGS. 3A-B, without the atraumatic dome 320

Figure 4A:
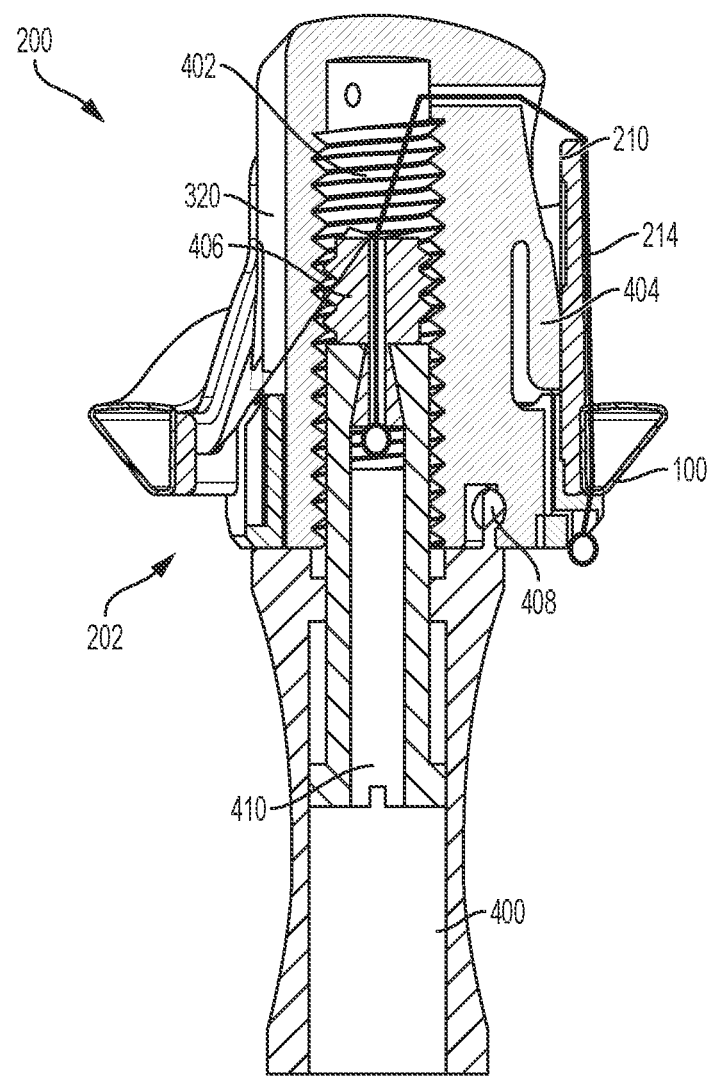
FIG. 4A is a partial cross-sectional view of an example suture guard, a prosthetic heart valve, and a delivery handle, in accordance with an embodiment.
Figure 5:
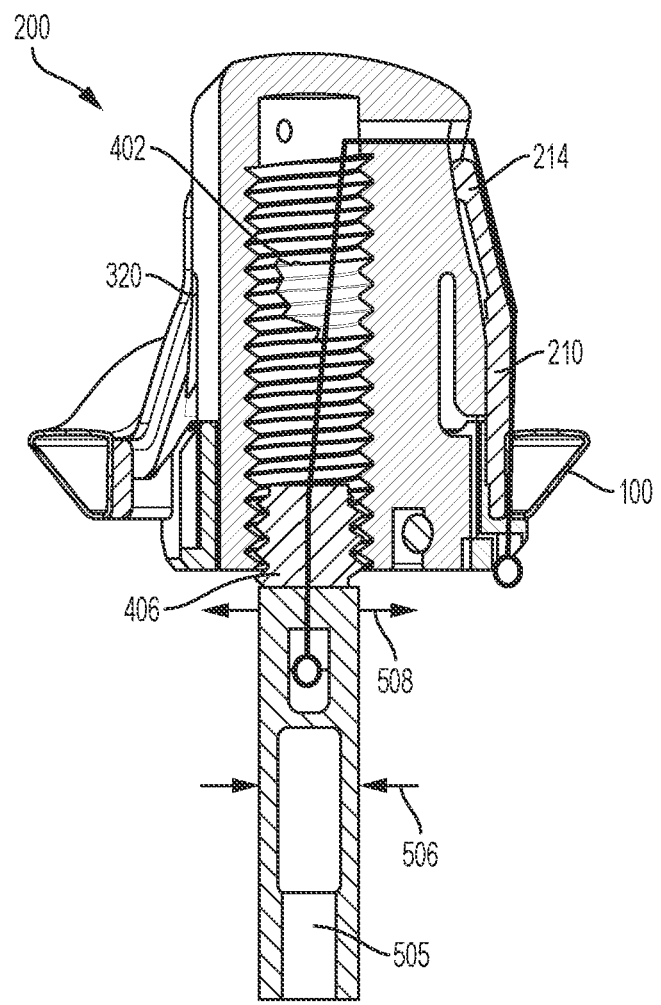
FIG. 5 is a partial cross-sectional view of an example suture guard, a prosthetic heart valve, and another delivery handle, in accordance with an embodiment.

FIG. 4A is a partial cross-sectional view of an example suture guard 202, a prosthetic heart valve 100, and a delivery handle 410, in accordance with an embodiment. The suture guard 202 shown in FIG. 4A includes an atraumatic dome 320 having an internally threaded portion 402. The atraumatic dome 320 includes deflection lobes 404 that are configured to interface and couple the atraumatic dome 320 to another portion of the suture guard 202. FIG. 4A also shows a sleeve 400 that is used to facilitate use of the delivery handle 410.

The sleeve 400 shown in FIG. 4A includes an externally threaded portion 406 that is configured to thread into the internally threaded portion 402 of the atraumatic dome 320. The externally threaded portion 406 is configured to interface with one or more fibers 214 that are arranged with one or more of the valve (commissure) posts 210 of the prosthetic valve 100. The delivery handle 410 is configured to apply tension to the one or more fibers 214. The externally threaded portion 406 rotates relative to the internally threaded portion 402 and applies tension to the fiber 214 due the externally threaded portion 406 and the internally threaded portion 402 moving apart. This maintains tension on the fiber 214 during implantation of the prosthetic valve 100. Because the fiber 214 is coupled to at least one of the one or more valve (commissure) posts 210 of the prosthetic valve 100, the handle 410 applies tension and moves the valve (commissure) posts 210 inwardly toward a longitudinal axis of the prosthetic valve 100.

The sleeve 400 includes tabs 408 that interface with the suture guard 202. In addition, the delivery handle 410 that is configured to move relative to the sleeve 400 to apply tension to the fiber 214. The delivery handle 410 is coupled to the externally threaded portion 406. FIG. 4-B show a portion of the delivery handle 410. The delivery handle 410 is accessible to an operating physician and extends outside the body. In certain instances, the delivery handle 410 portion shown attaches to another handle. The delivery handle 410 shown may be disposable.

Figure 4B:
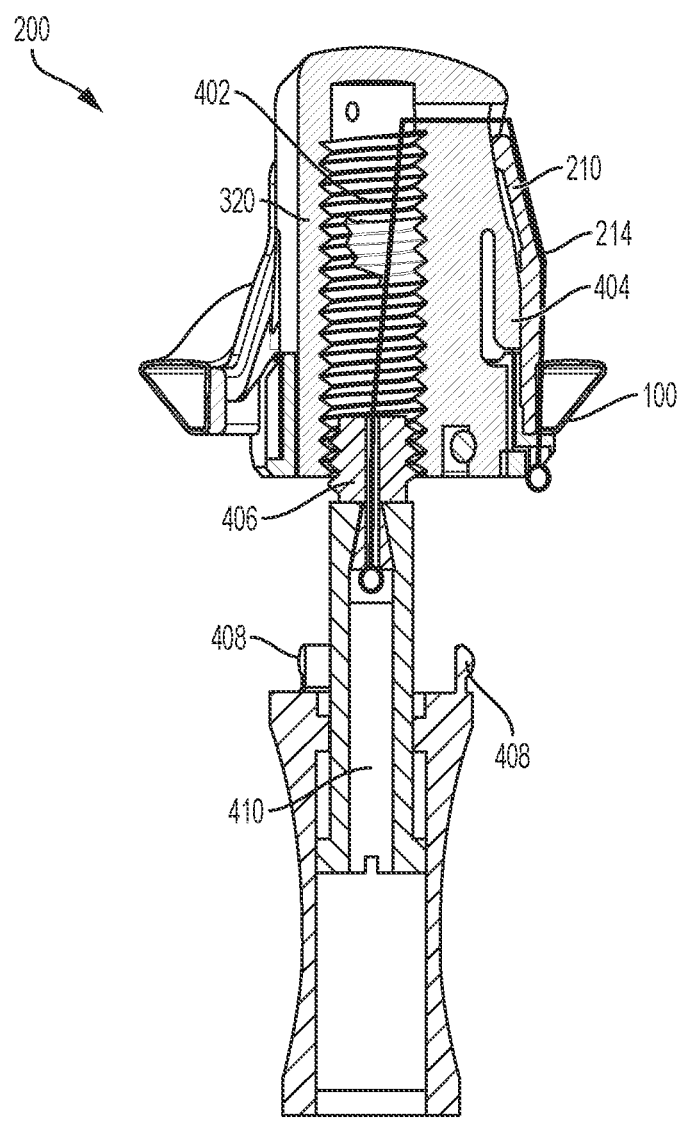
FIG. 4B is a partial cross-sectional view of the suture guard, the prosthetic heart valve, and the delivery handle, as shown in FIG. 4A, in another configuration.

FIG. 4B is a partial cross-sectional view of the suture guard 202, the prosthetic heart valve 100, and the sleeve 400, as shown in FIG. 4A, in another configuration. The sleeve 400 is separated from the suture guard 202 in the configuration shown in FIG. 4B. As shown in FIG. 4B, the illustrative valve (commissure) post 210 is moved inwardly compared to the configuration shown in FIG. 4A. To facilitate release of the sleeve 400 from the suture guard 202, the delivery handle 410 is dovetailed at the point of interface with the externally threaded portion 406. As a result, the externally threaded portion 410 may be slid perpendicular to the externally threaded portion 406 to release from the externally threaded portion 406. Thus, the delivery handle 410 and the sleeve 400 are uncoupled and released from the suture guard 202.

FIG. 5 is a partial cross-sectional view of an example valve holding 200 device, a prosthetic heart valve 100, and another delivery handle 505, in accordance with an embodiment. The suture guard 202 shown in FIG. 5 includes an atraumatic dome 320 having an internally threaded portion 402. The delivery handle 505 is accessible to an operating physician and extends outside the body. In certain instances, the delivery handle 505 portion shown attaches to another handle. The delivery handle 505 shown may be disposable.

The delivery handle 505 shown in FIG. 5 includes an externally threaded portion 406 that is configured to thread into the internally threaded portion 402 of the atraumatic dome 320. The externally threaded portion 406 is configured to interface with one or more fibers 214 that are arranged with one or more of the valve (commissure) posts 210 of the prosthetic valve 100. The delivery handle 505 is configured to control the suture guard 202 and apply tension to the one or more fibers 214. The externally threaded portion 406 rotates relative to the internally threaded portion 402 and applies tension to the fiber 214 and maintains tension on the fiber 214 during delivery and implantation of the prosthetic valve 100. Because the fiber 214 is coupled to at least one of the one or more valve (commissure) posts 210 of the prosthetic valve 100, the handle 505 applies tension and moves the valve (commissure) posts 210 inwardly toward a longitudinal axis of the prosthetic valve 100 as shown in FIG. 5.

The delivery handle 505 configured to separate from the suture guard 202 by applying pressure at area 506 as indicated by the arrows. Applying pressure at the area 506 opens the delivery handle 505 at area 508 as indicated by the arrows. As a result, the delivery handle 505 releases the externally threaded portion 406. Thus, the delivery handle 505 is uncoupled from the suture guard 202.

Figure 6:
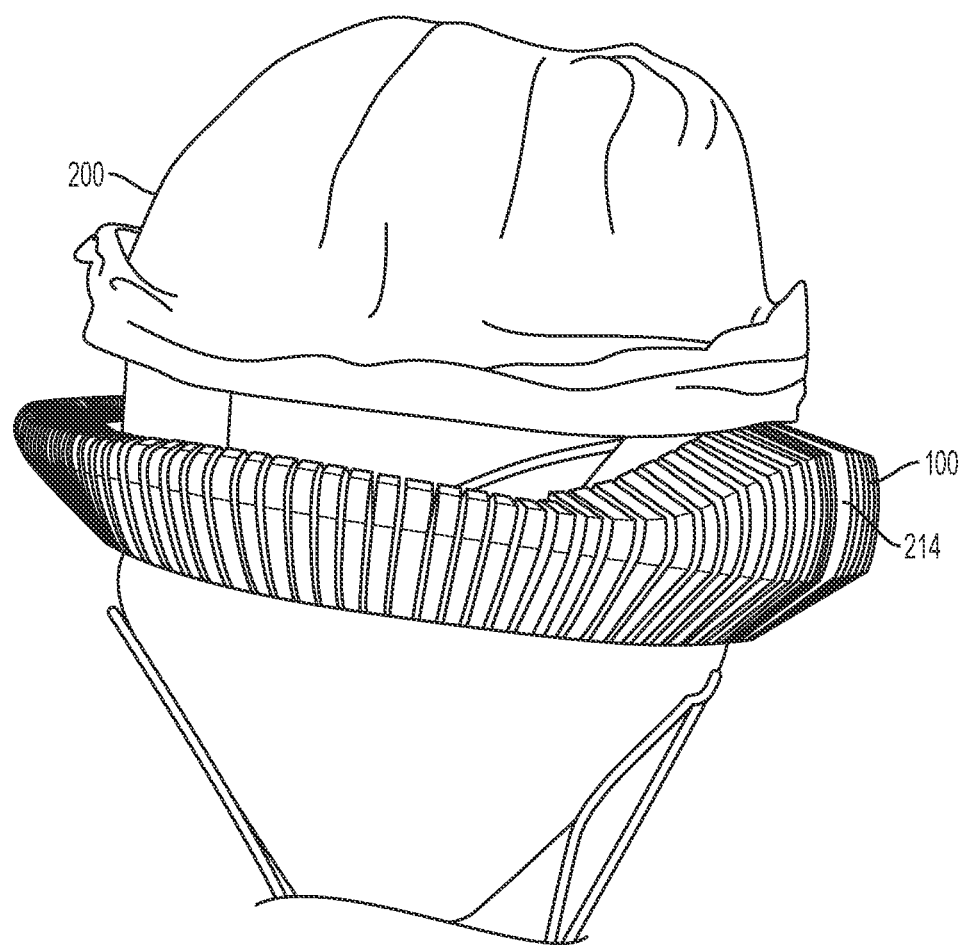
FIG. 6 is an illustration of an example suture guard and a prosthetic heart valve, in accordance with an embodiment.
Figure 18:
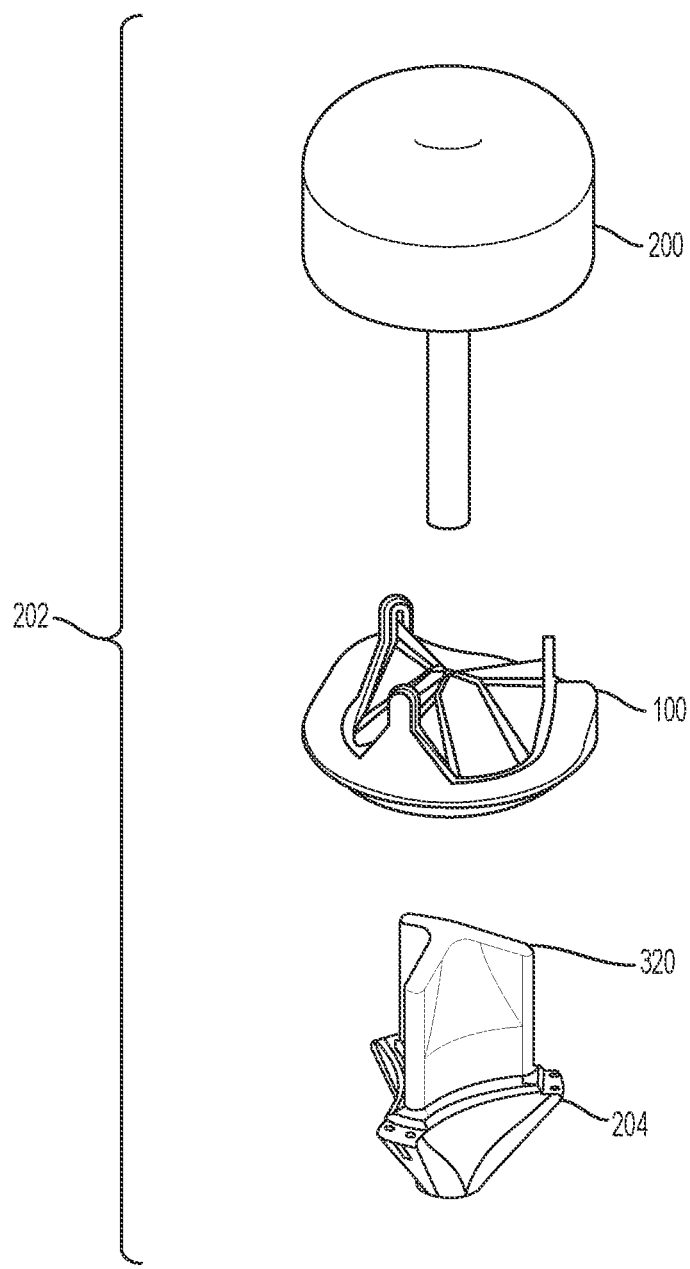
FIG. 18 is an exploded view of the everted suture guard shown in FIG. 6.
Figure 19:
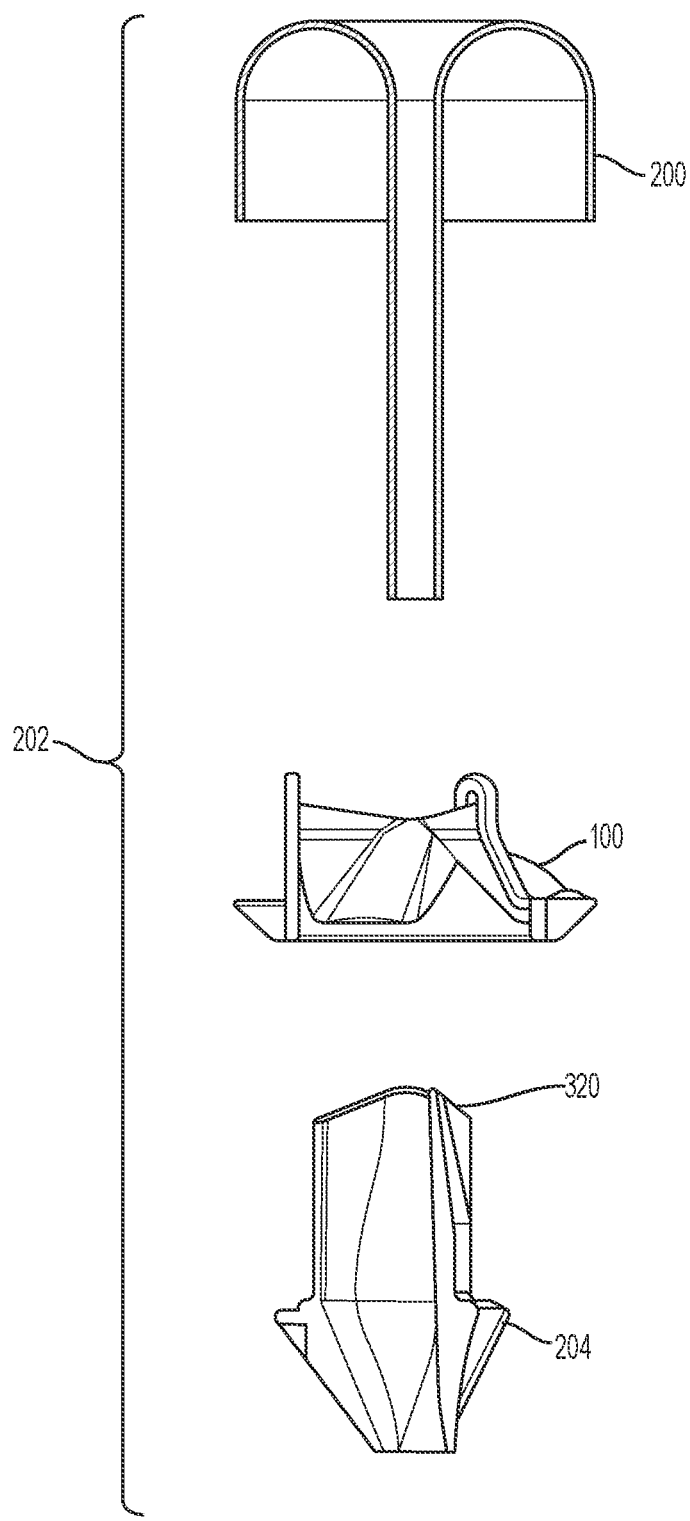
FIG. 19 is another exploded view of the everted suture guard shown in FIG. 6, showing a cross section of a portion of the suture guard.
Figure 20:
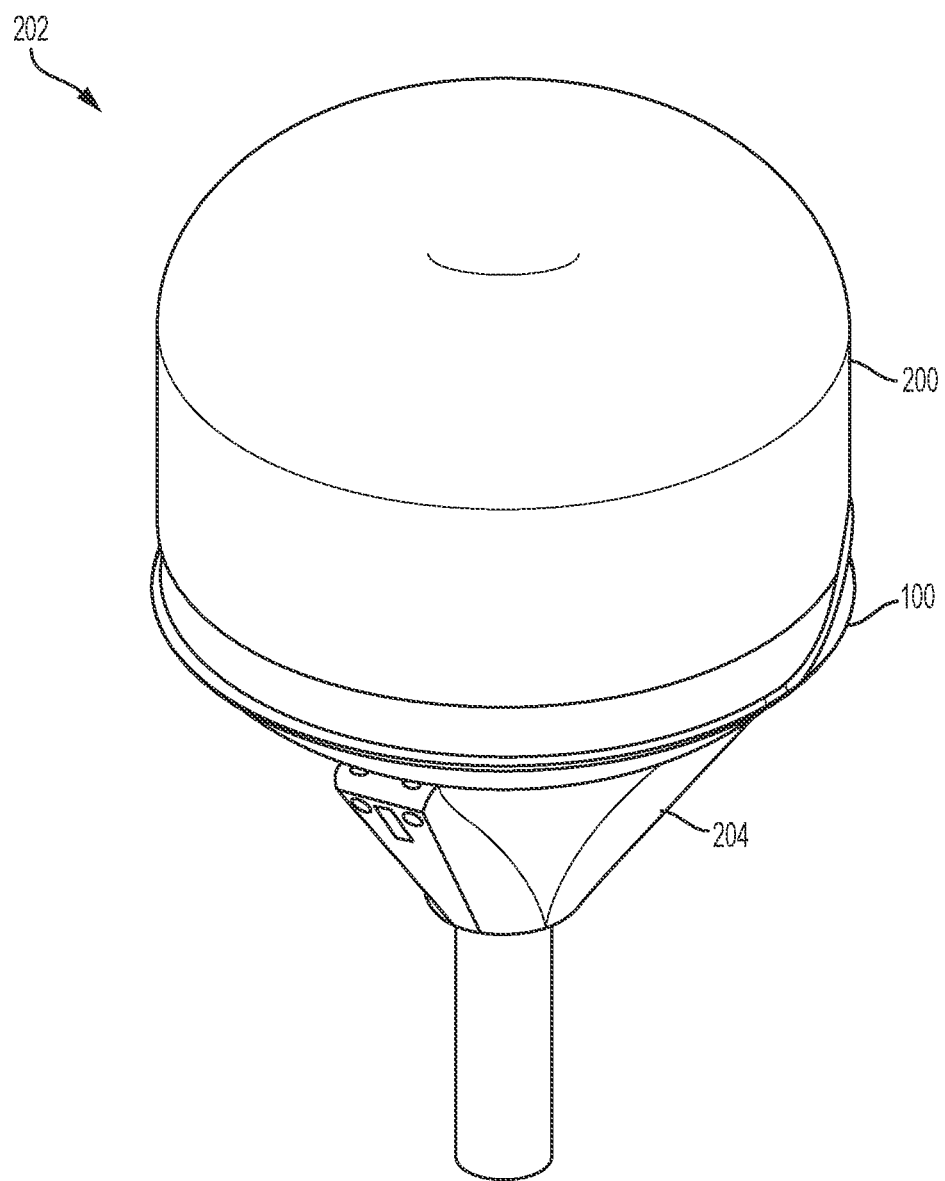
FIG. 20 is another view of the everted suture guard shown in FIG. 6 and FIGS. 18-19.
Figure 21:
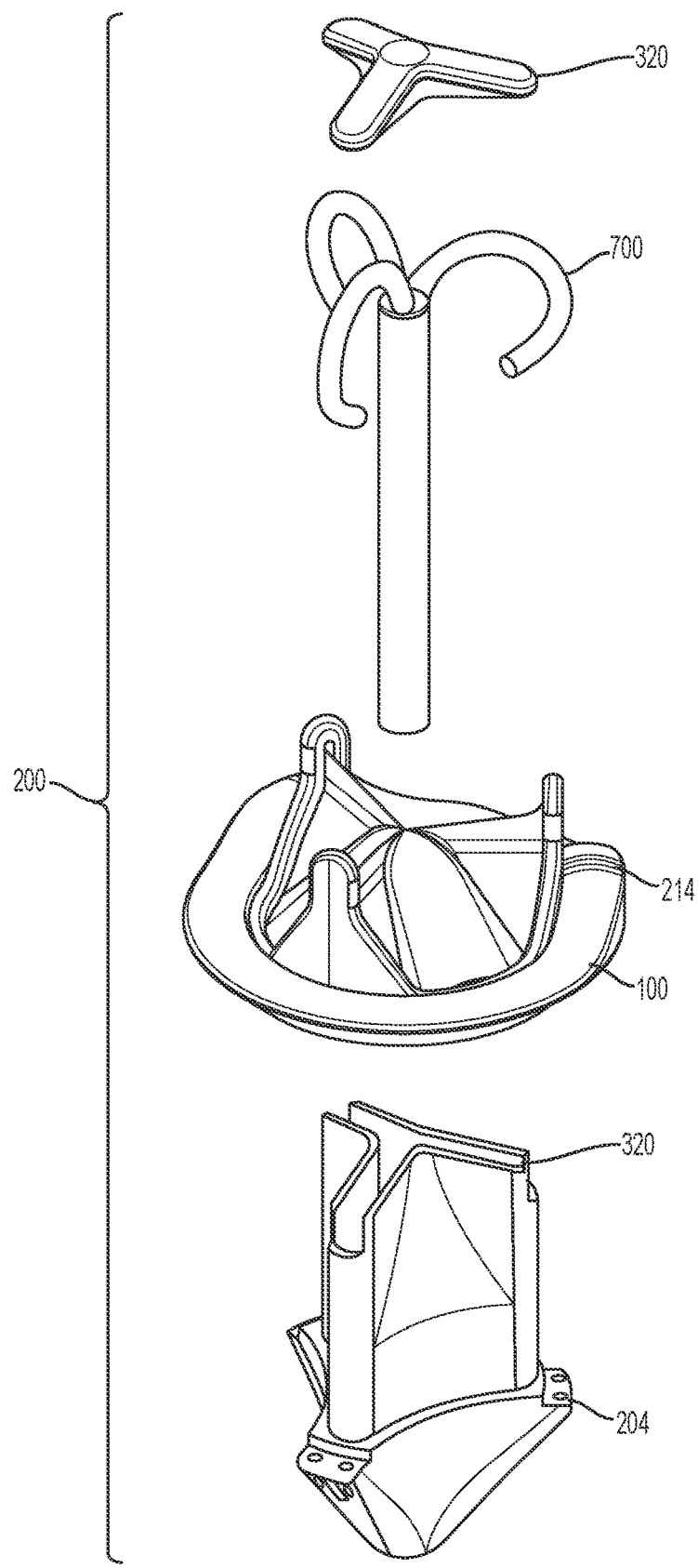
FIG. 21 is an exploded view of suture guard shown in FIG. 7.
Figure 22:
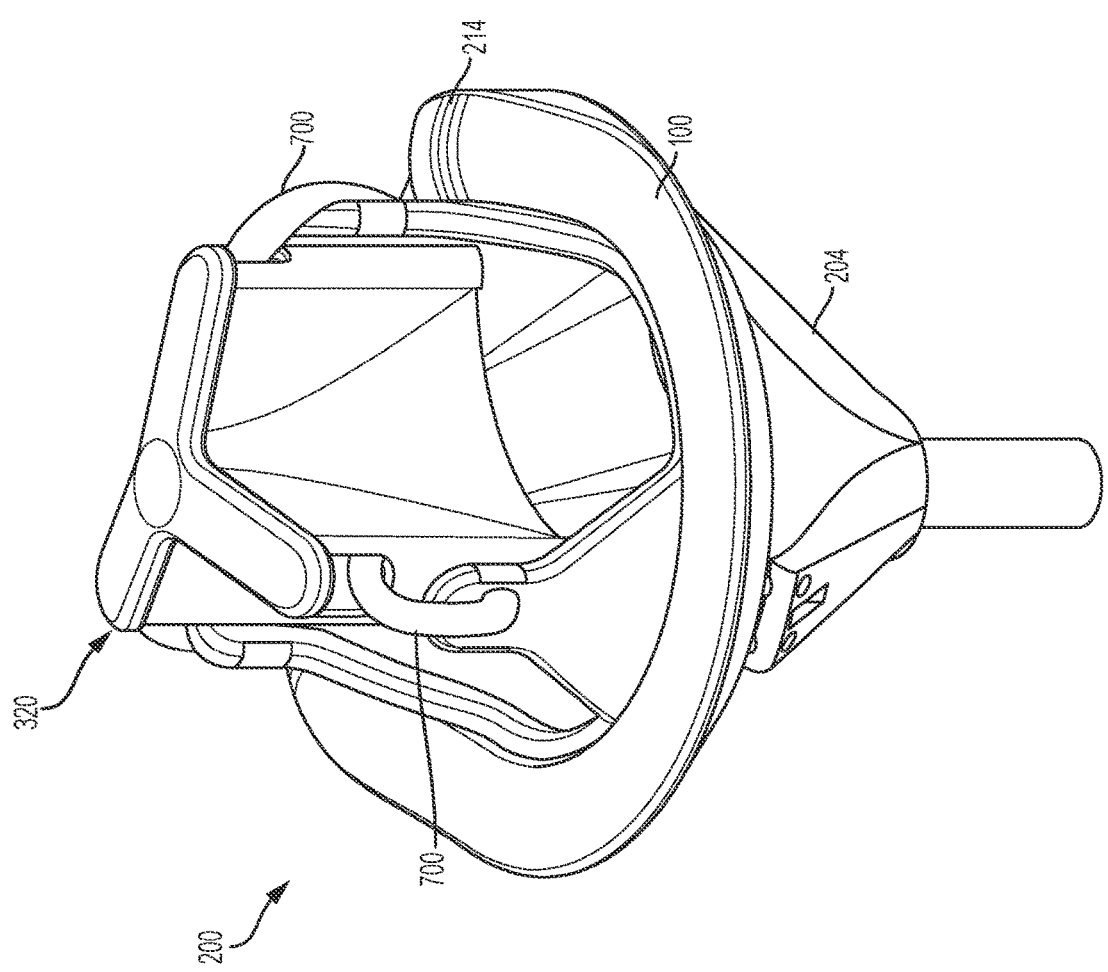
FIG. 22 is another view of the everted suture guard shown in FIG. 7 and FIG. 21.

FIG. 6 is an illustration of an example suture guard 202 and a prosthetic heart valve 100, in accordance with an embodiment. The holding device 200 shown in FIG. 6 is an everted tube. The everted tube holding device 200 is arranged through the inflow portion of the prosthetic valve 100 and folded over the valve (commissure) posts (for further detail regarding the everted tube holding device 200, reference may be made to FIGS. 18-20). The everted tube holding device 200 is secured in place by a fiber that is arranged through the prosthetic valve 100 in accordance with the examples discussed above. As shown, the everted tube holding device 200 is configured to cover the valve (commissure) posts to help minimize the potential for suture looping. For example, the everted tube holding device 200 operates to deflect suture line extending along and exterior of the valve from becoming entangled with one or more of the covered valve (commissure) posts during the implantation procedure.

In some examples, the everted tube holding device 200 may be configured to engage the valve (commissure) posts to move the one or more valve (commissure) posts of the prosthetic valve 100 inwardly toward a longitudinal axis of the prosthetic valve 100. For instance, to move the valve (commissure) posts inwardly, the everted tube holding device 200 may be configured to create a surface on which the fiber 214 or fibers 214 (as noted above, the number of fibers may be equal to the number of valve (commissure) posts) slide, as they are tensioned in relation to the valve (commissure) posts, which causes the valve (commissure) posts to be moved inward. Additionally or alternatively, the everted tube holding device 200 may provide cushioning to the valve (commissure) posts to further reduce likelihood of trauma during implantation.

The everted tube holding device 200 may be removed from the prosthetic heart valve 100 by releasing the fiber 214 or fibers 214, which releasing tension on the everted tube holding device 200 and the valve (commissure) posts. The everted tube holding device 200 may then be slid through the prosthetic valve 100. Additional examples of suture guards that operate to cover one or more of the valve (commissure) posts are illustrated and described further below with regard to FIGS. 29A-33B.

Figure 7:
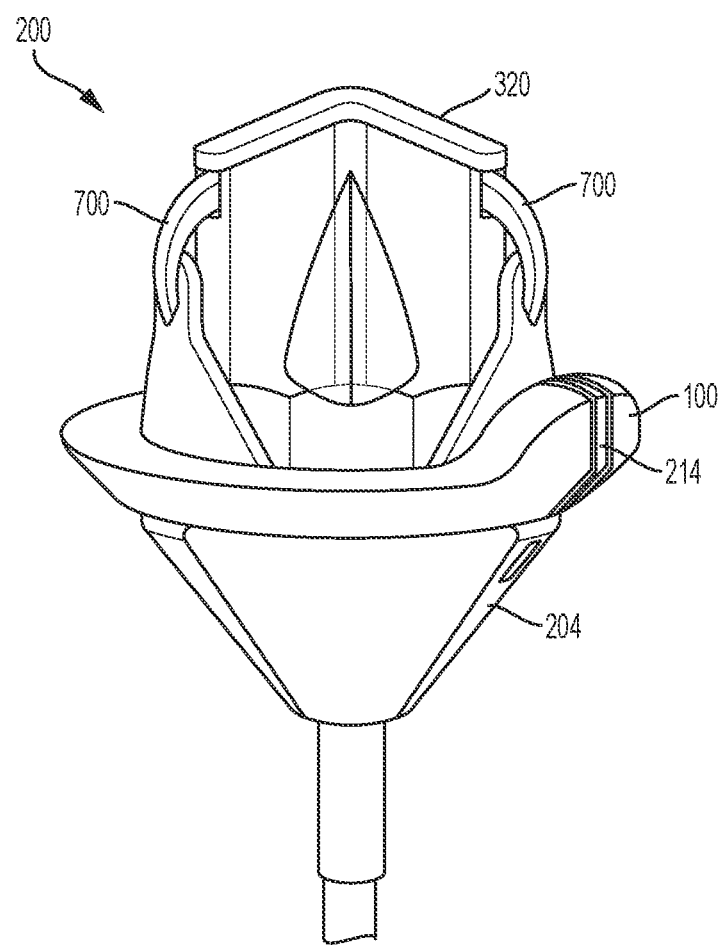
FIG. 7 is an illustration of another example suture guard and a prosthetic heart valve, in accordance with an embodiment.

FIG. 7 is an illustration of another example suture guard 202 and a prosthetic heart valve 100, in accordance with an embodiment. The suture guard 202 includes one or more retractable arms 700 that cover valve (commissure) posts of the prosthetic heart valve 100. The retractable arms 700 provide a soft barrier between the valve (commissure) posts of the prosthetic heart valve 100 and anatomical features, such as the interior walls of the heart, thereby reducing the likelihood of trauma. These arms also provide a ramping surface for fiber loops 214 to slide past the valve (commissure) posts of the prosthetic heart valve 100. The retractable arms 700 can be retractable allowing for the prosthetic heart valve 100 to be removed from the upstream side of the prosthetic heart valve 100.

The suture guards discussed herein are configured to protect prosthetic heart valves during surgery, protect tissue during insertion, and provide room for suture placement and tying as discussed in detail above. The suture guards 200 are also configured to connect and disconnect to a delivery handle, and attach/detach from prosthetic heart valves 100 from the inflow direction.

Figure 8:
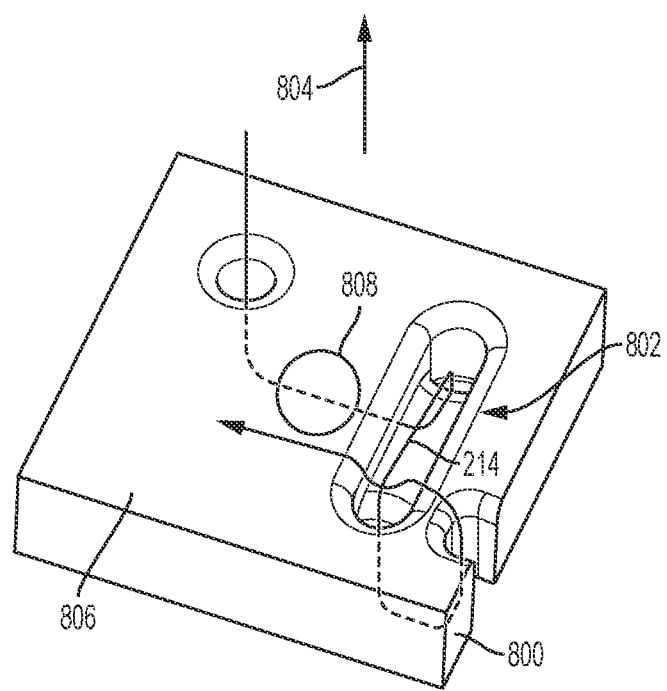
FIG. 8 is an illustration of example fiber wrapping pathway, in accordance with an embodiment.

FIG. 8 is an illustration of example fiber pathway, in accordance with an embodiment. The fiber 214 may be routed across a surface 800 and through a trough 802. The fiber 214 includes a non-adjustable direction 804 and an adjustable direction 806. As shown in FIG. 8, the fiber 214 is routed underneath itself resulting in the fiber 214 arranged in the trough 802 when the non-adjustable direction 804 is placed under tension.

The surface 800 includes an area 808 on the back of the surface 800, which can be a device as discussed herein, to facilitate removal of the fiber 214 by cutting the fiber 214. The routing of the fiber 214 allows for one of the fiber to slip when pulled (in the adjustable direction 806) while not allowing the other end of the fiber 214 to slip (in the non-adjustable direction 804).

The surface 800 may be a portion of the suture guard 202 shown and discussed herein. The surface 800 and corresponding features shown in FIG. 8, for example, may be arranged at the perimeter of the suture guard 202 for the fiber 214. Anywhere the fibers 214 are anchored (e.g., fiber holding portions shown in FIGS. 2A-G or knotted portions 322 shown in FIGS. 3A-B) may utilize the aspects of FIG. 8.

Figure 9:
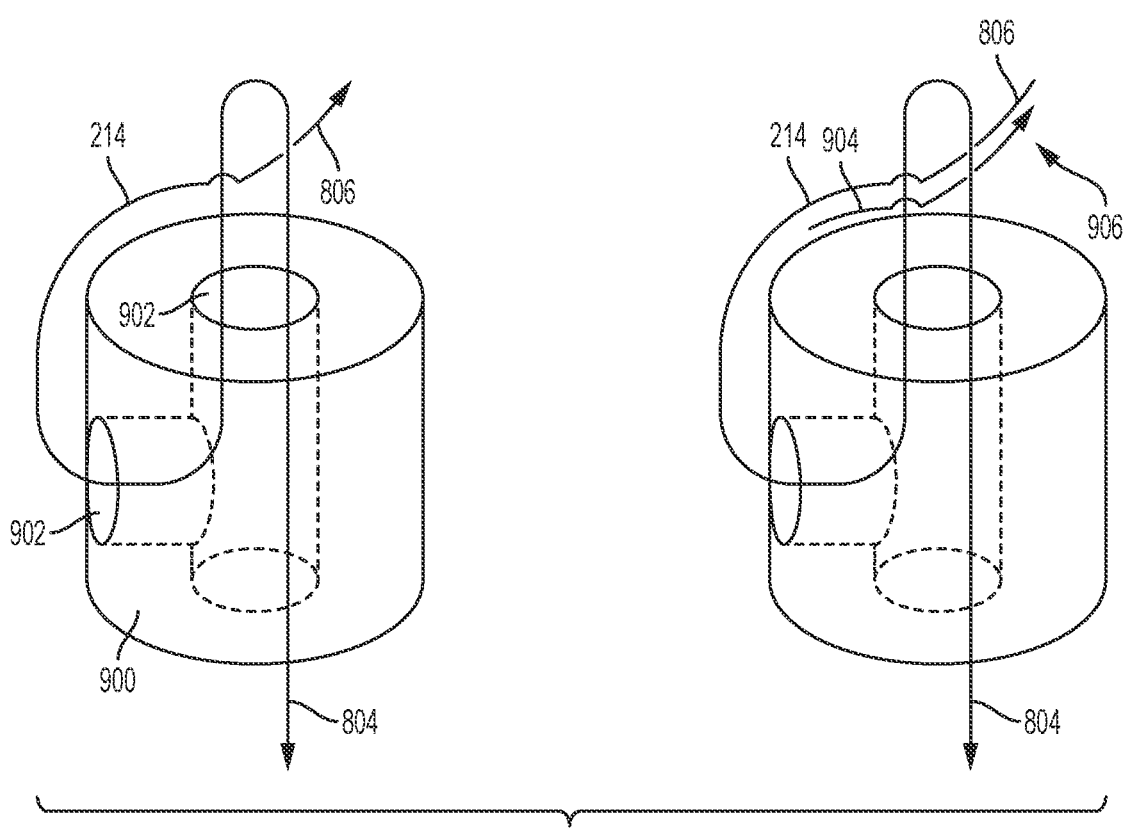
FIG. 9 is an illustration of example fiber wrapping pathway, in accordance with an embodiment.
Figure 10:
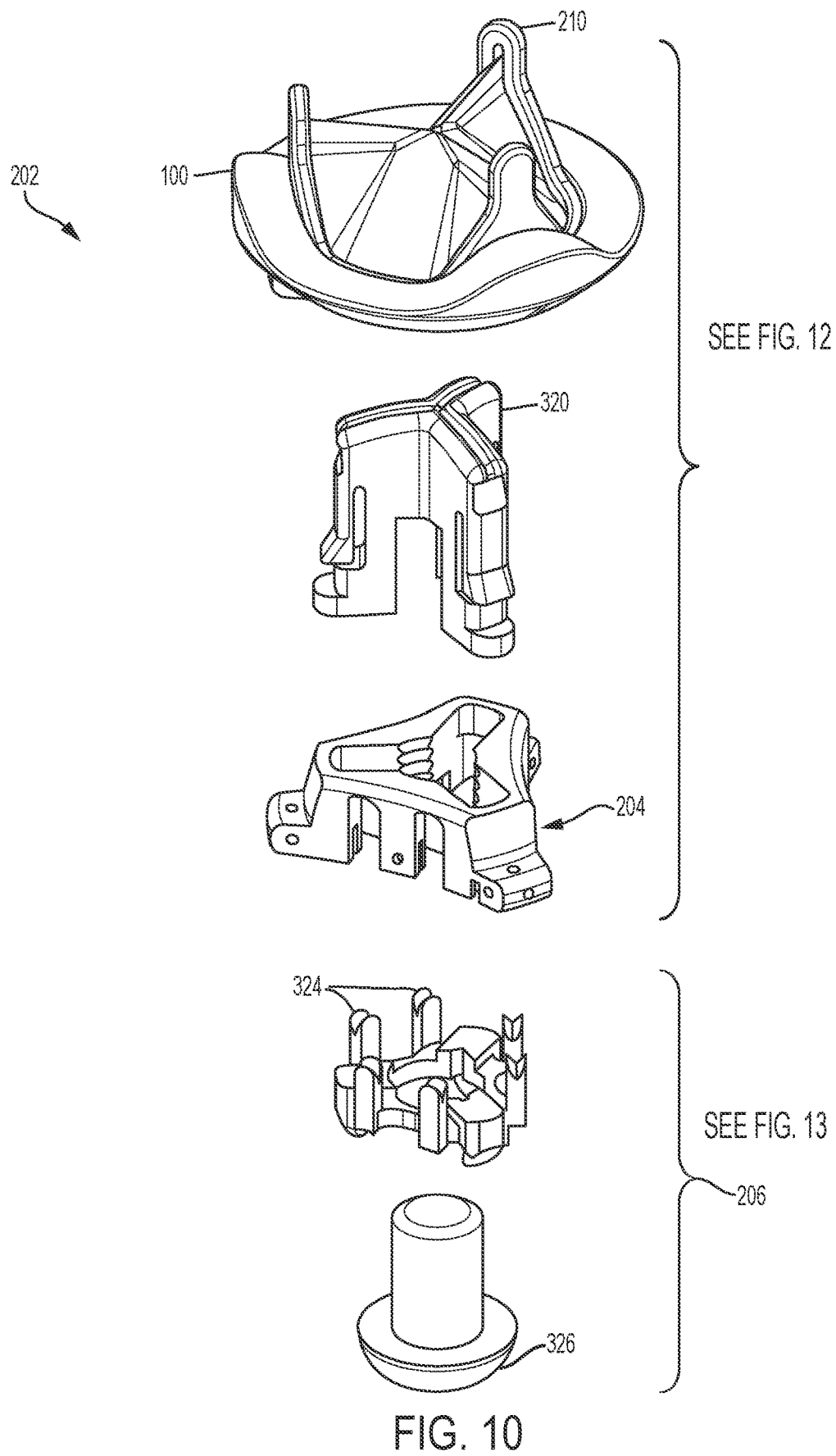
FIG. 10 is an exploded view of the example suture guard shown in FIGS. 3A-C.
Figure 11:
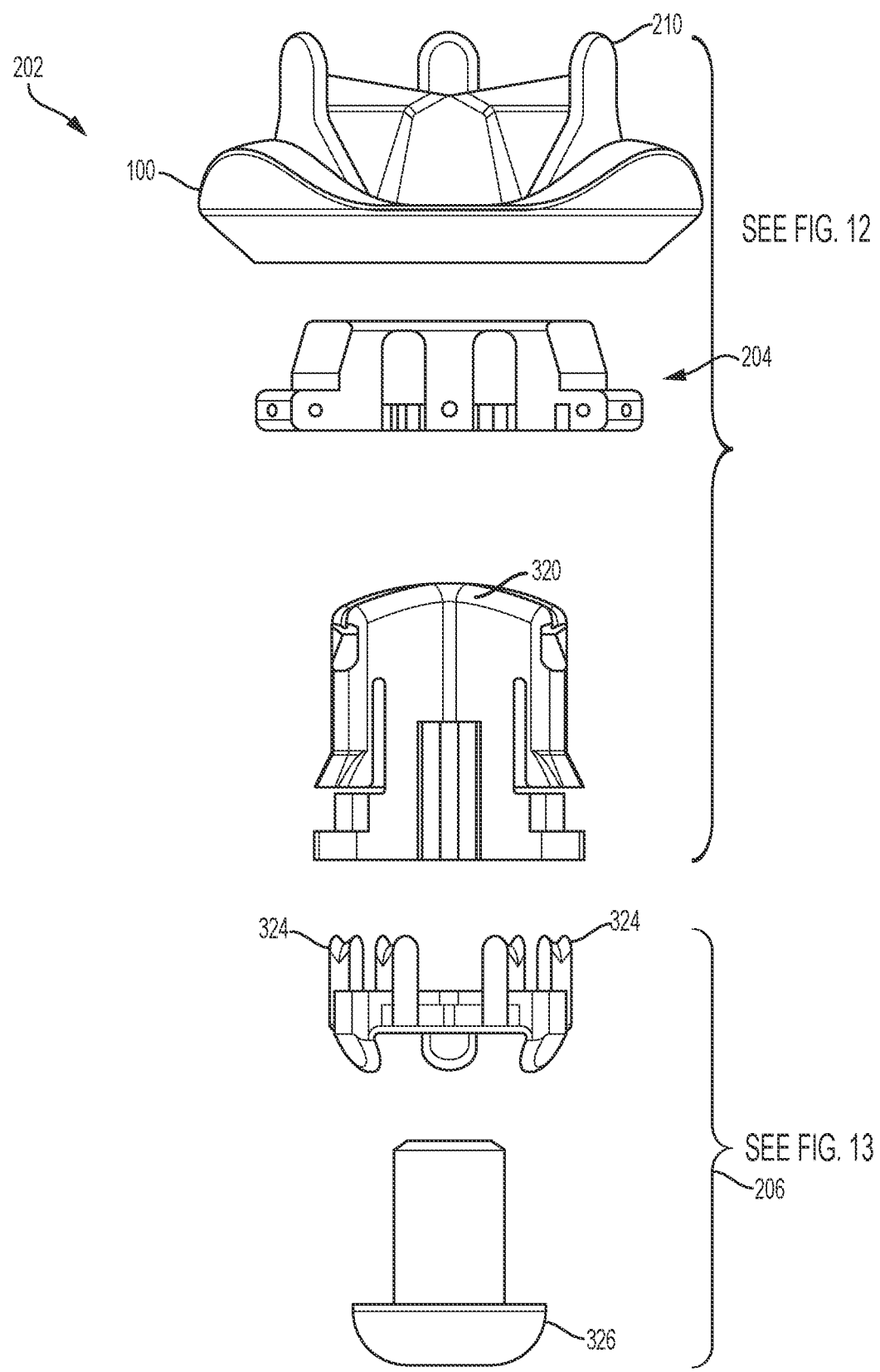
FIG. 11 is another exploded view of the example suture guard shown in FIGS. 3A-C.
Figure 12:
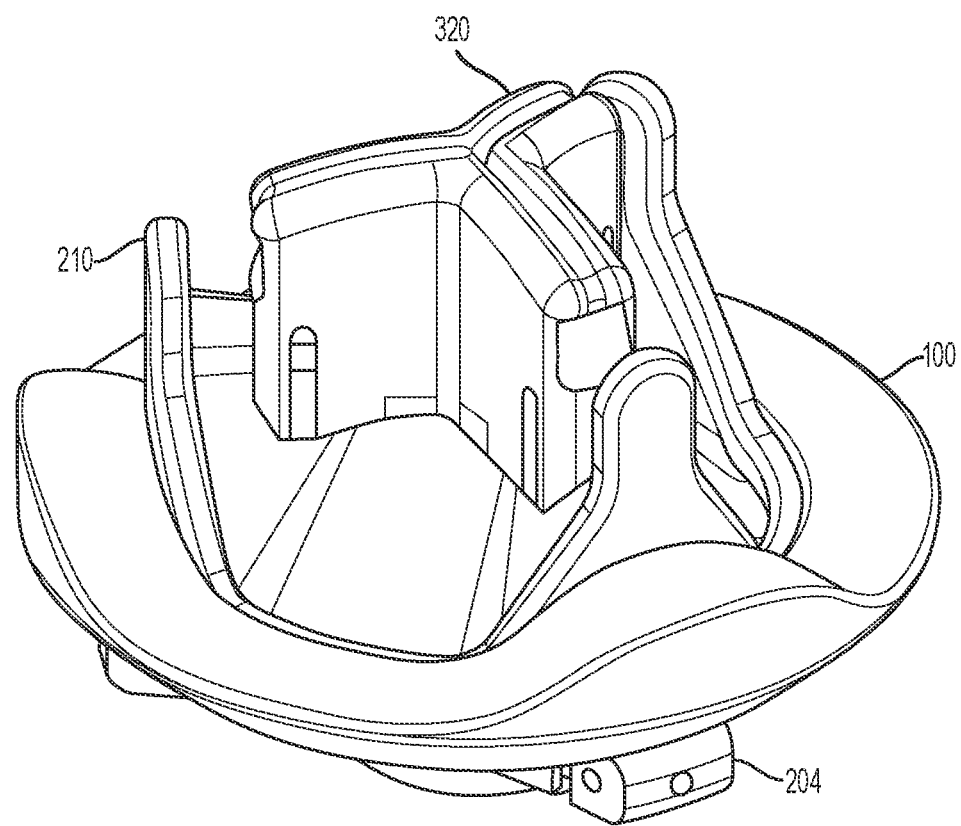
FIG. 12 is an illustration of portions of the example suture guard shown FIGS. 10-11.
Figure 13:
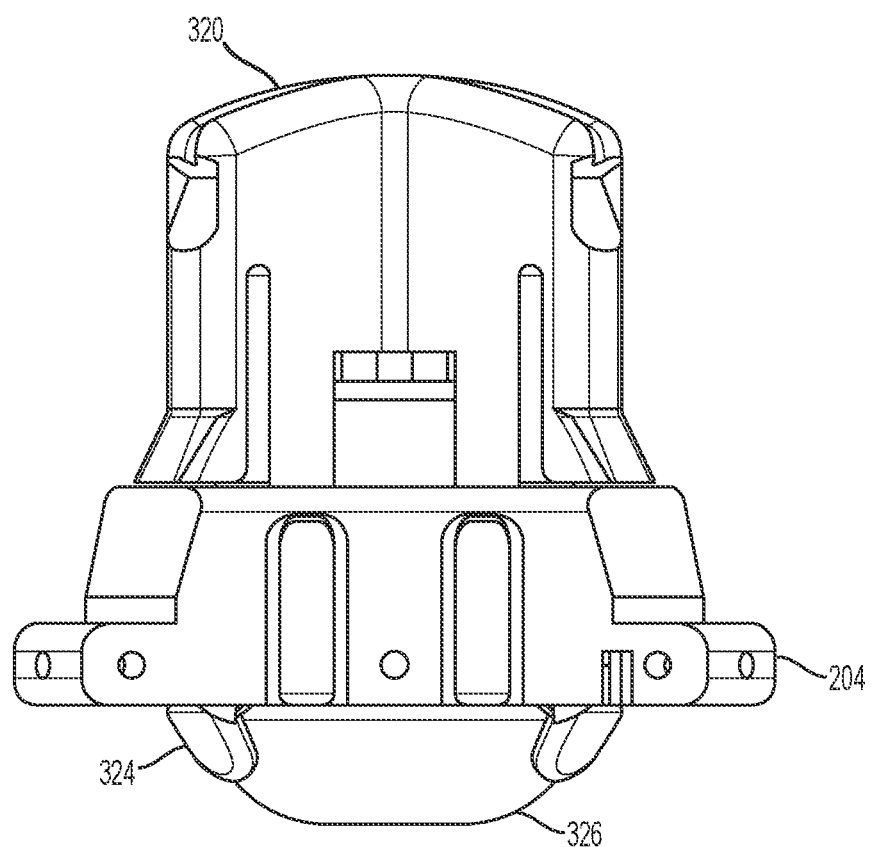
FIG. 13 is an illustration of portions of the example suture guard shown FIGS. 10-11.
Figure 14:
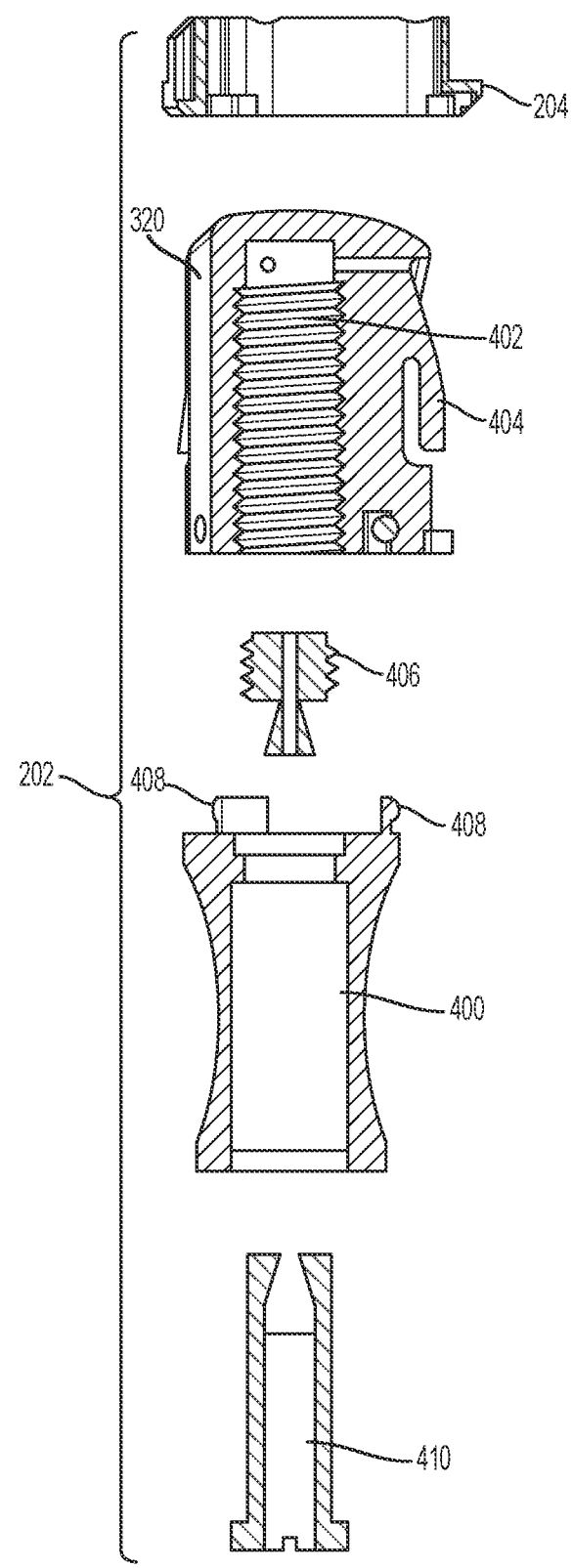
FIGS. 14-17 are exploded views of delivery handles and suture guards shown in FIGS. 4-5.
Figure 15:
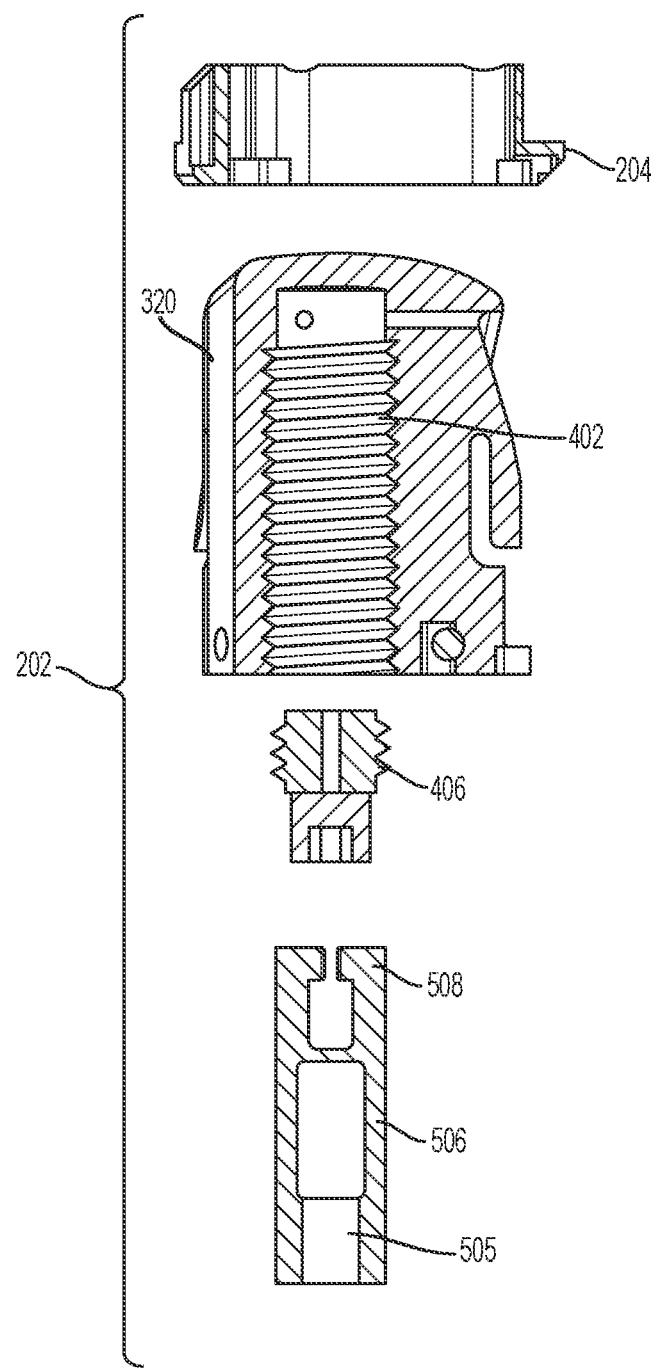
Figure 16:
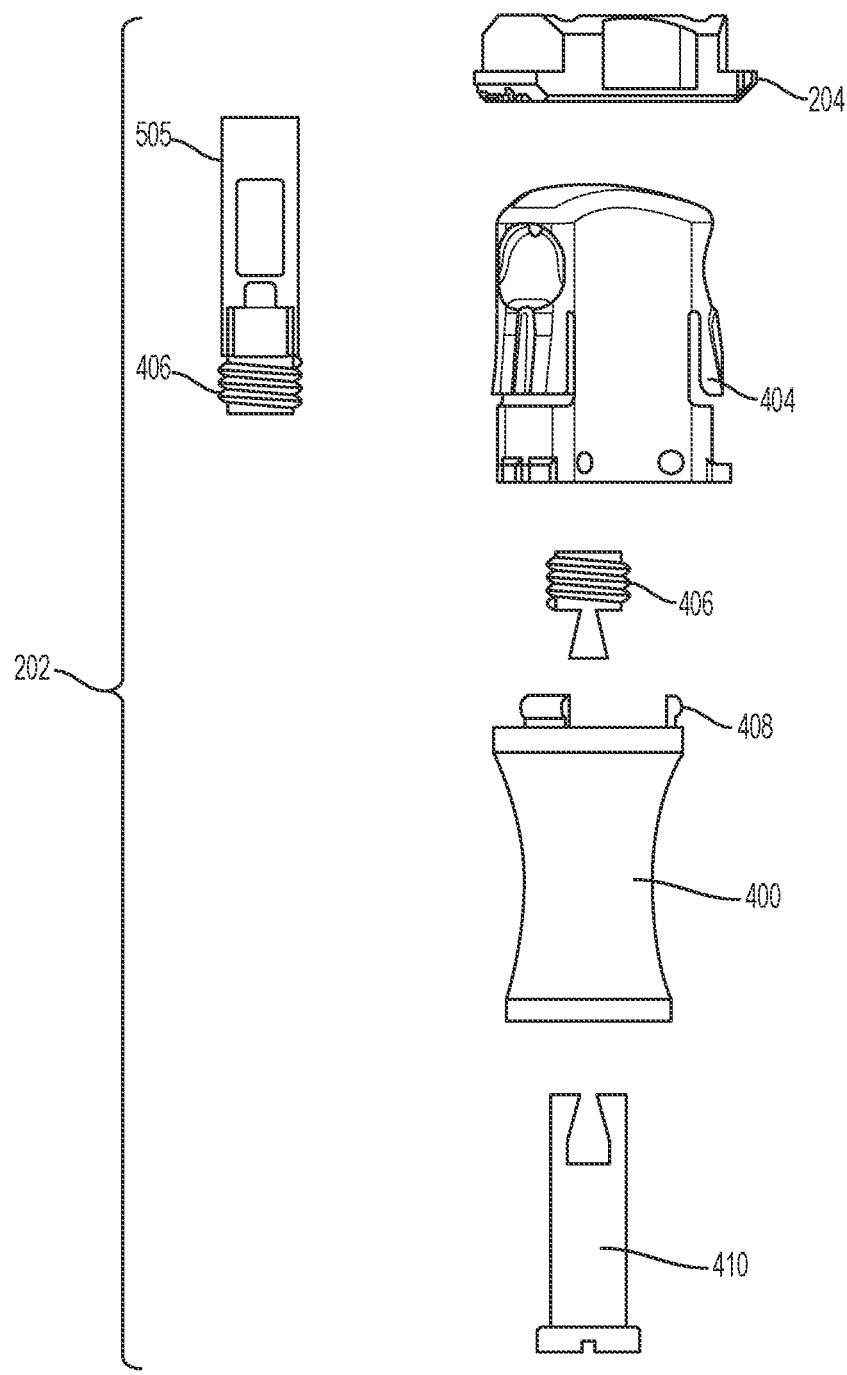
Figure 17:
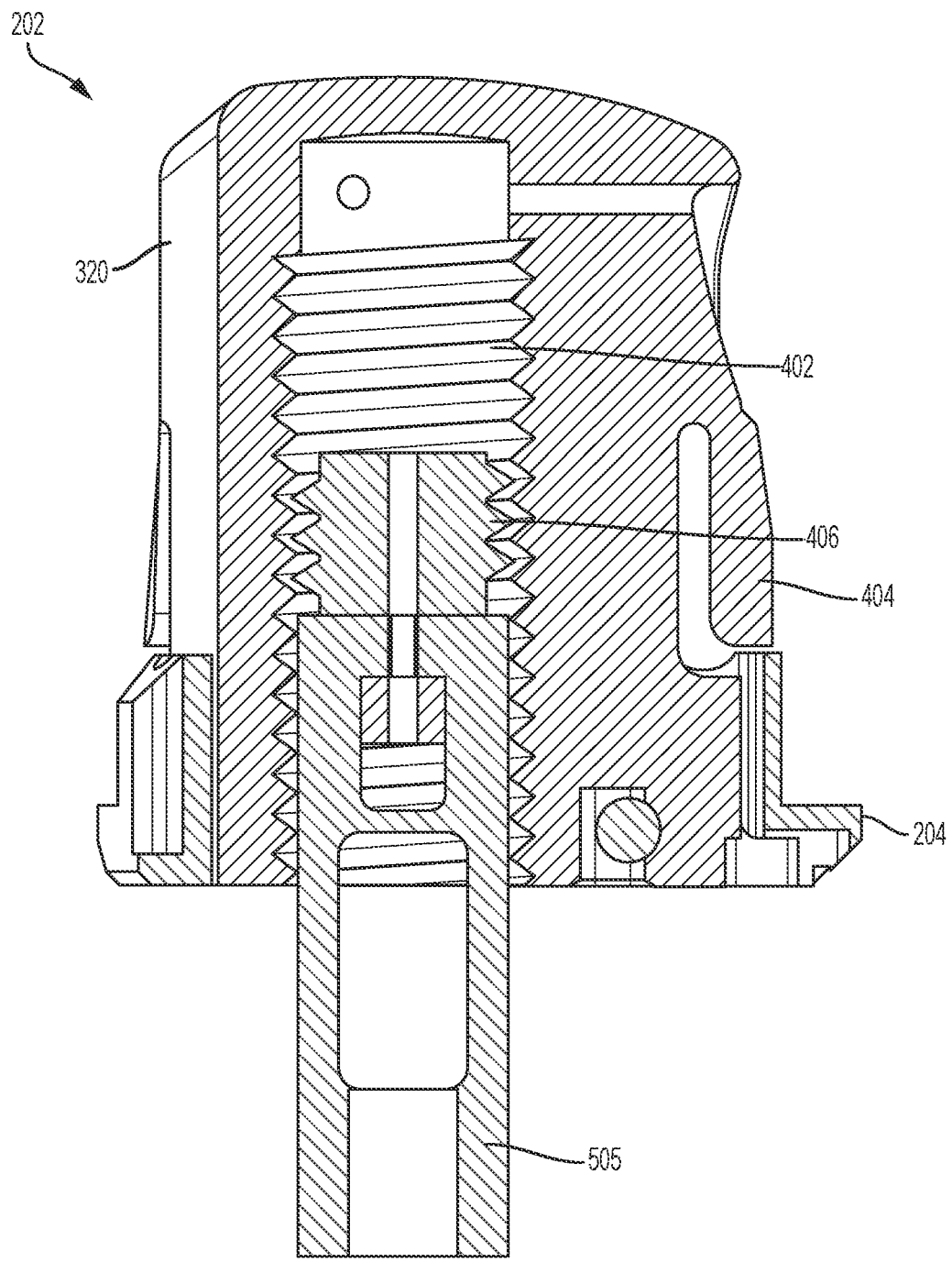

FIG. 9 is an illustration of example fiber wrapping pathway, in accordance with an embodiment. The fiber 214 may be routed through a device 900. The device includes pathways 902 through which the fiber 214 may be routed. The fiber 214 includes a non-adjustable direction 804 and an adjustable direction 806. As shown in FIG. 9, the fiber 214 is routed onto itself. The pathways 902 are large enough to fit two fibers 214 as shown in the left portion of FIG. 9, but not for three fibers 214. In certain embodiments, a release fiber 904 may be used to release the fiber 214. The release fiber 904 acts as lock loop that can release the fiber 214 when pulled in a release direction 906. As shown in the right portion of FIG. 9, the pathways 902 are large enough for 3 fibers but not for 4 fibers.

The routing of the fiber 214 allows for one of the fiber to slip when pulled (in the adjustable direction 806) while not allowing the other end of the fiber 214 to slip (in the non-adjustable direction 804).

The device 900 may be a portion of the suture guard 202 shown and discussed herein. The device 900 and corresponding features shown in FIG. 9, for example, may be arranged at the perimeter of the suture guard 202 for the fiber 214. Anywhere the fibers 214 are anchored (e.g., fiber holding portions shown in FIGS. 2A-G or knotted portions 322 shown in FIGS. 3A-B) may utilize the aspects of FIG. 9.

Figure 23:
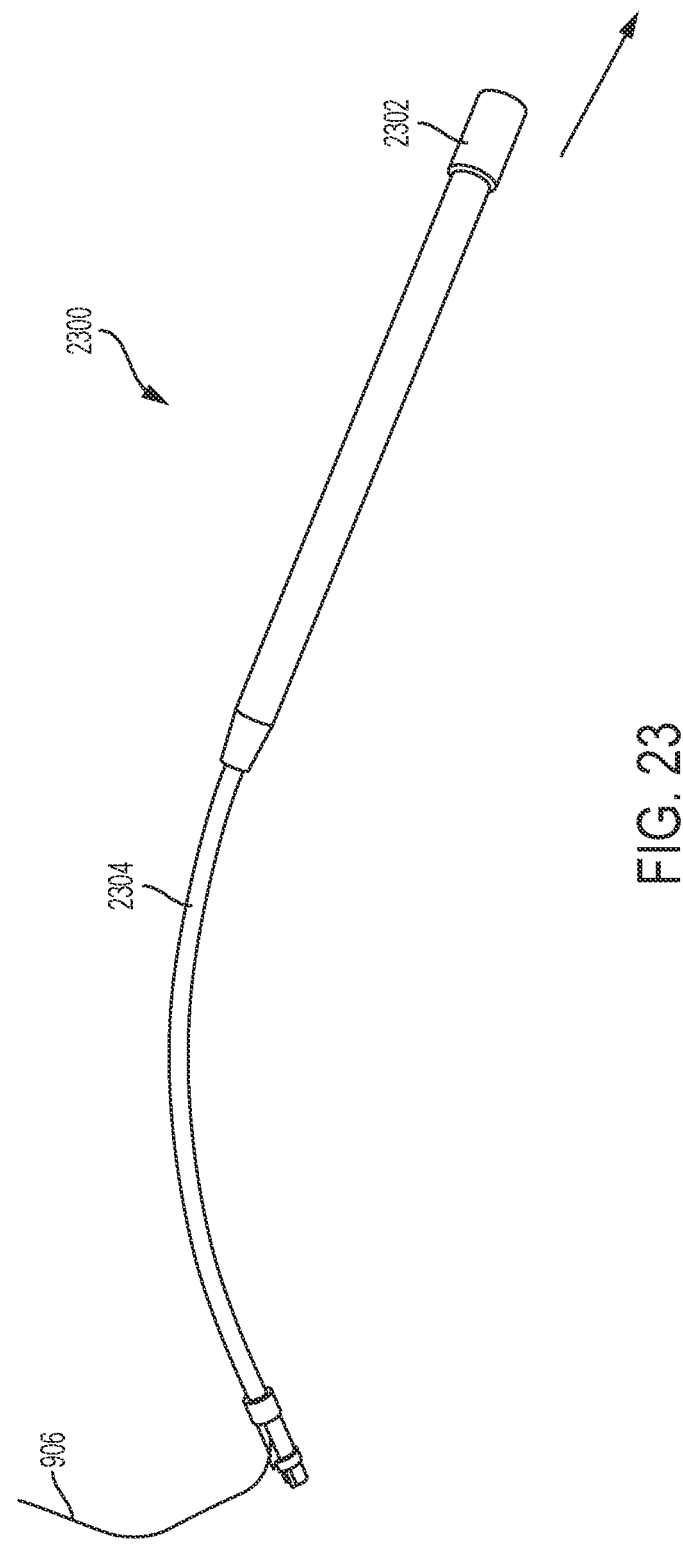
FIG. 23 is an illustration of an example handle, in accordance with an embodiment.
Figure 24:
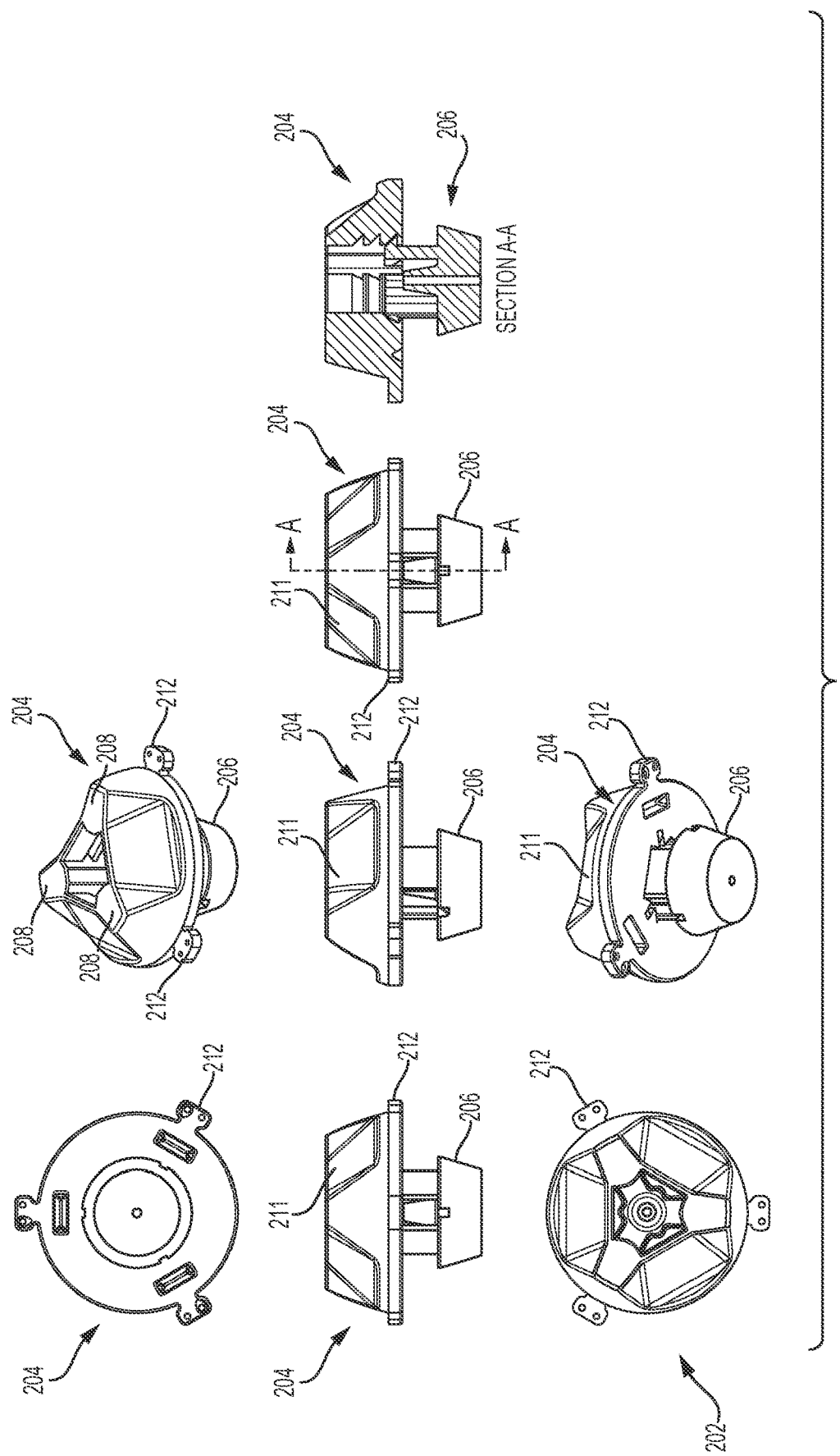
FIG. 24 is a schematic illustration of the various components of the suture guard shown in FIGS. 2A-G, in the configuration shown in FIG. 2F.
Figure 25:
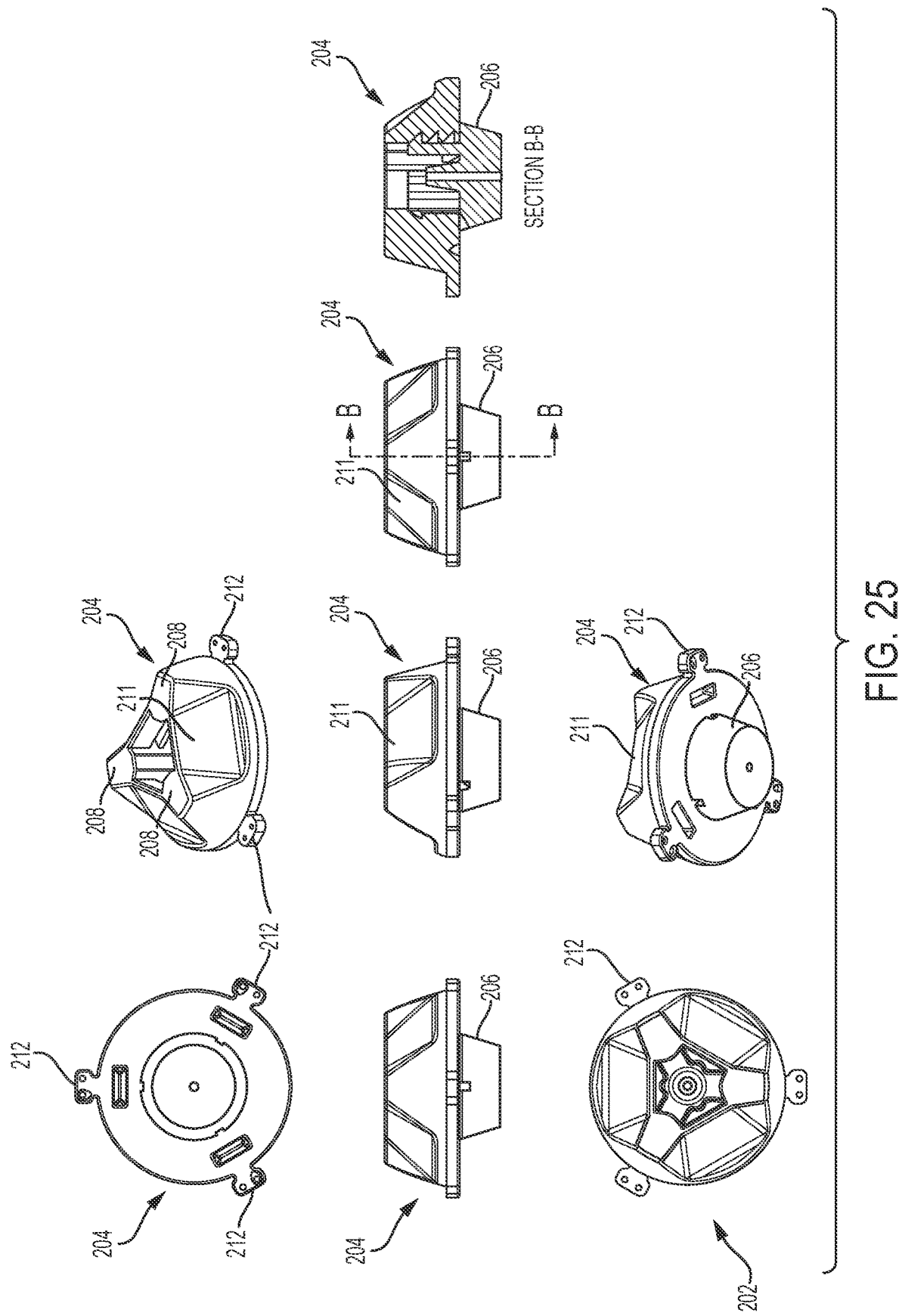
FIG. 25 is a schematic illustration of the various components of the suture guard shown in FIGS. 2A-G, in the configuration shown in FIG. 2G.
Figure 26:
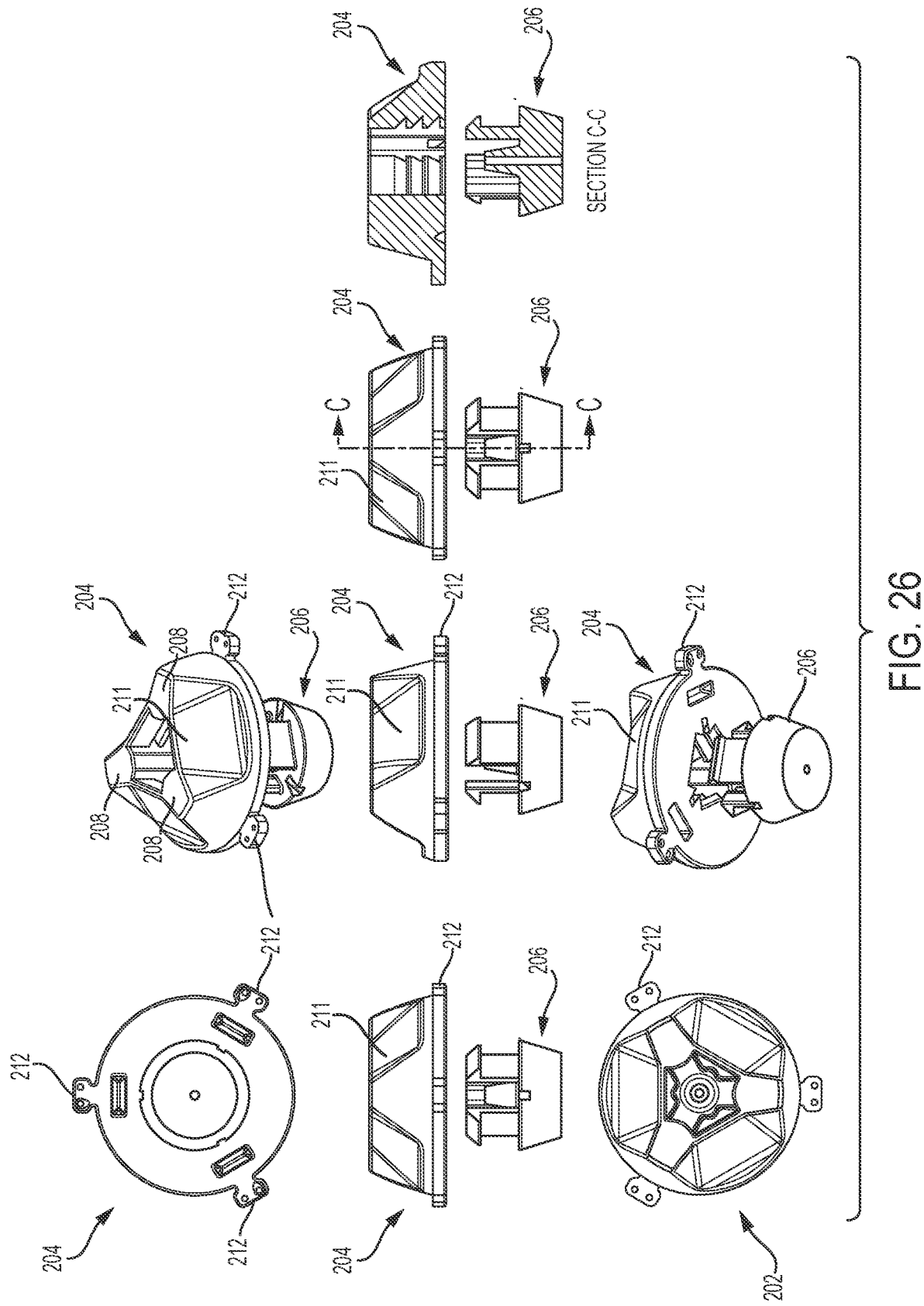
FIG. 26 is a schematic exploded illustration of the various components of the suture guard shown in FIGS. 2A-G.
Figure 27:
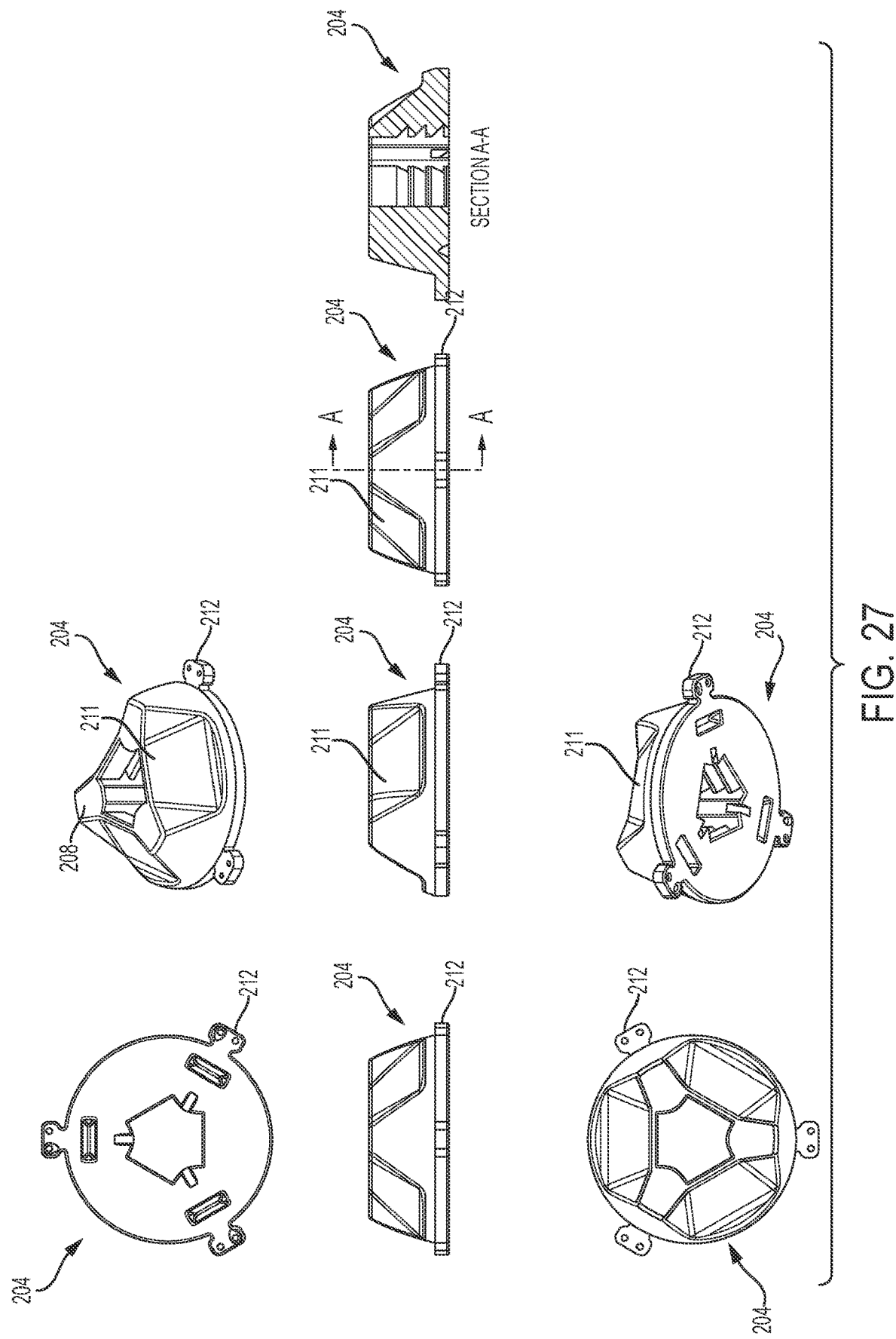
FIG. 27 is a schematic illustration of the first portion of the suture guard shown in FIGS. 2A-G.
Figure 28:
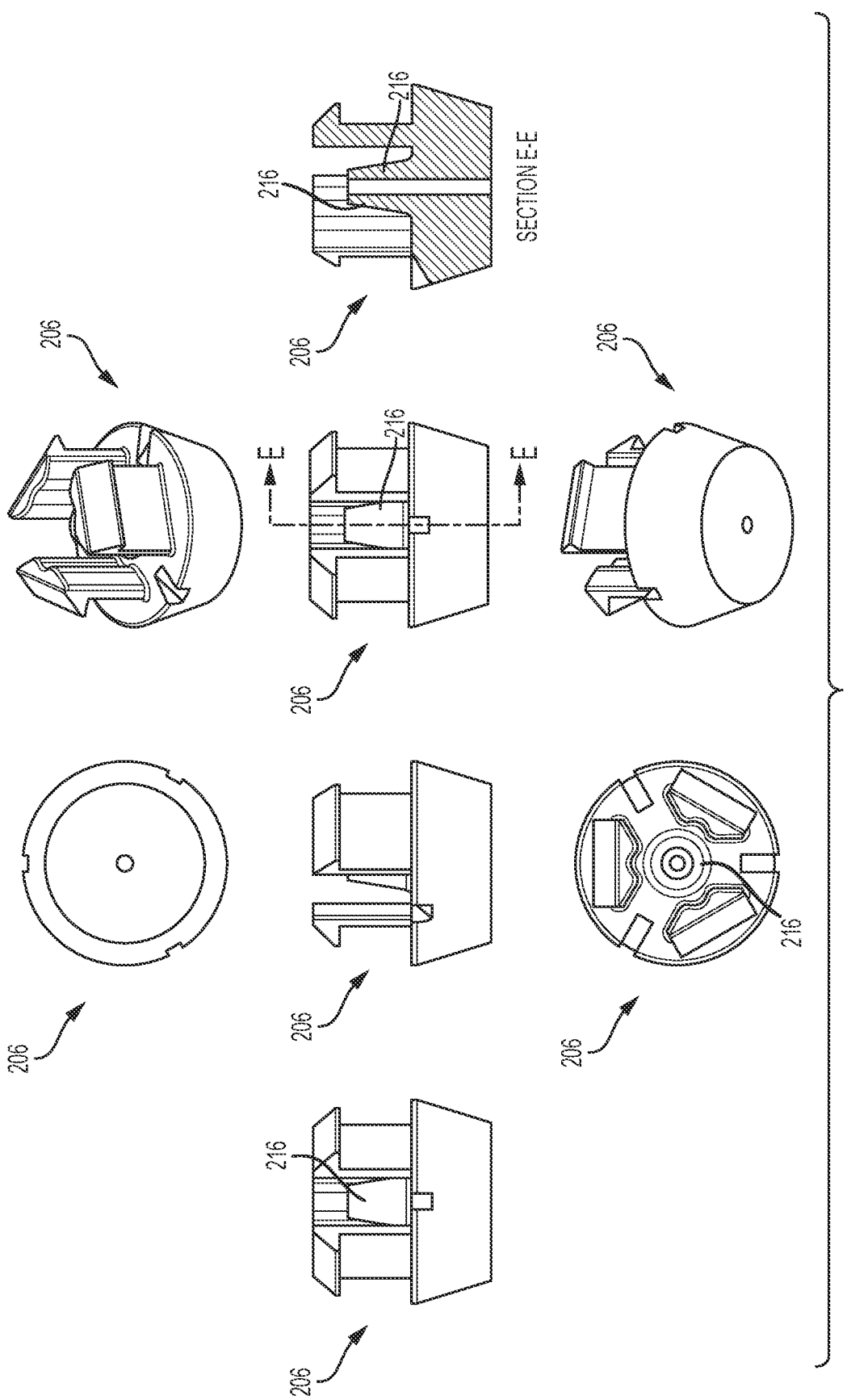
FIG. 28 is a schematic illustration of the second portion of the suture guard shown in FIGS. 2A-G.

FIG. 23 is an illustration of an example handle 2300, in accordance with an embodiment. The handle 2300 may be disposable and remotely actuatable to release fibers 214 from the suture guards 202 discussed herein. As shown in FIG. 23, the handle 2300 includes a release fiber 904. The release fiber 904 can be engaged with fibers 214 as shown in FIG. 9.

An end of the release fiber 904 may also be coupled to cap 2302. The cap 2302 is removeable from the handle 2300 by pulling on the cap 2302 in the direction shown. In this manner, the release fiber 904 is removed through a catheter 2304 portion of the handle 2300. As a result, the release fiber 904 unlocks the fiber 214 or fibers 214, as shown in FIG. 9.

As noted above, upon application of linear motion by the suture guard 202, the one or more fiber lines 214 are configured to apply tension to move one or more valve posts 210 of the prosthetic valve 100 inwardly toward a longitudinal axis of the prosthetic valve 100. The release fiber 906 is coupled to the cap 2302 and configured to releasably lock the one or more fiber lines 214 with the suture guard 202, as discussed with reference to FIG. 9. Upon actuation and removal of the cap 2302 from the handle 2300, the release fiber 906 releases the release fiber 906 from the pattern shown in FIG. 9 to unlock the one or more fiber lines 214.

FIGS. 29A to 33B provide illustration on an example system 1000 according to some embodiments. The system 1000 generally includes a suture guard 2000 that operates to protect one or more components of a heart valve 100 during an implantation procedure of the heart valve 100. In various embodiments, the suture guard 2000 is configured to minimize a possibility for entanglement of suture line (or other deployment components) with one or more portions of the heart valve 100. For instance, as mentioned above, in various implantation procedures, one or more suture lines are utilized to install or implant the prosthetic heart valve 100 into a native valve annulus. In certain implantation procedures, the heart valve 100 is translated along one or more suture lines toward the native valve annulus (see, e.g., FIG. 32). The suture guard 2000 operates to help minimize a possibility that the suture line will become entangled with one or more of the commissure posts 210 as the heart valve 100 is translated along the suture line by covering, for example, one or more commissure posts of the prosthetic heart valve 100. It should be appreciated that the prosthetic heart valve 100 illustrated and described with reference to FIGS. 29A-29E, 32, and 33A-1 and 33A-2 is consistent in form and function with the heart valve 100 illustrated and described above.

Figure 32:
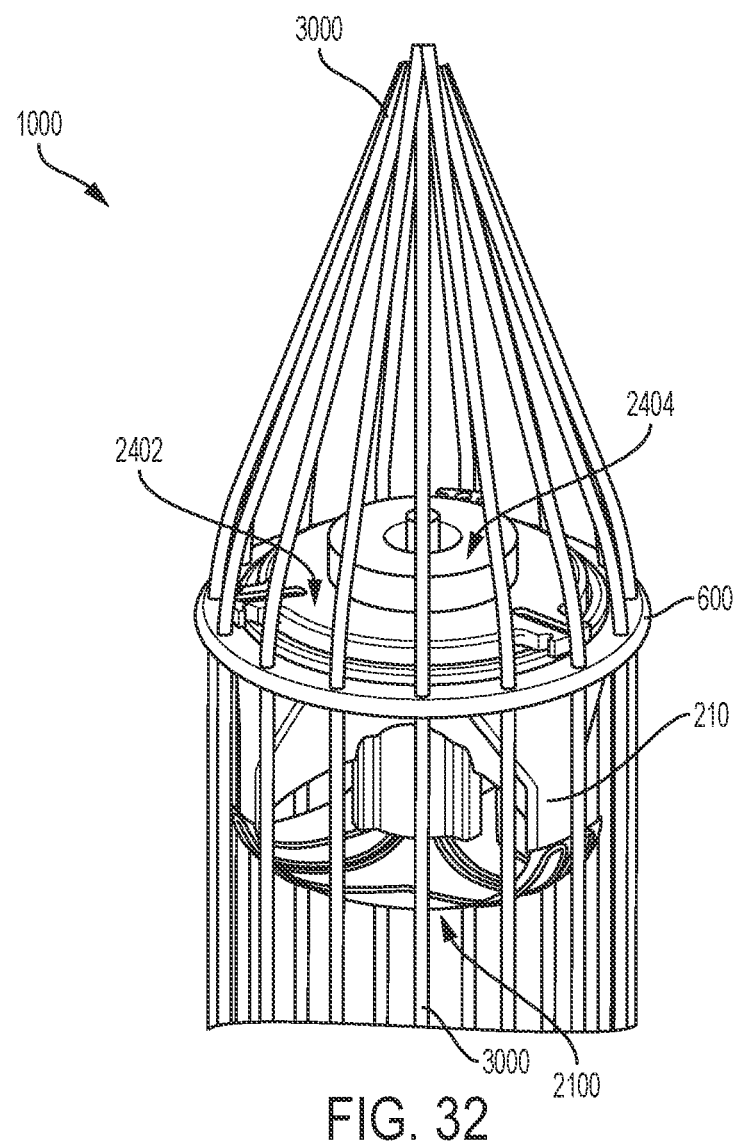
FIG. 32 is a schematic illustration of the example suture guard shown in FIG. 29A during an implantation procedure, in accordance with an embodiment.

In some examples, the suture guard 2000 is configured such that it operates to deflect suture line such that the suture line does not cross from one side of a commissure post 210 to an opposing side of the commissure post radially inwardly of the commissure post 210. For instance, in some examples, the suture guard 2000 is configured to extend over the commissure posts 210 of the heart valve 100 as shown in FIGS. 29A-29E. FIG. 32 also provides an illustration of the suture guard 2000 deployed over a heart valve 100 with suture line 3000 extending along the exterior of the commissure posts 210 of the heart valve 100. While not essential, in some embodiments, the suture guard 2000 may optionally be configured such that upon deployment of the suture guard 2000, the suture guard 2000 engages the commissure posts 210 to cause a radially inward deflection thereof.

It is also to be appreciated that the suture guard 2000 illustrated and described with regard to FIGS. 29A-33B may be optionally used in combination with the various other suture guards illustrated and described herein. For instance, after utilizing suture guard 202 (e.g., FIGS. 2A-2G) to deflect the valve posts radially inward in preparing a heart valve 100 for insertion into the annulus, for example, the suture guard 2000 illustrated and described with regard to FIGS. 29A-33B may be utilized to cover the commissure posts 210 the heart valve 100 to help deflect suture line extending along and exterior of the heart valve 100 from becoming entangled with the commissure posts 210. Alternatively, the suture guard 2000 illustrated and described with regard to FIGS. 29A-33B may be utilized in lieu of the various other suture guards illustrated and described herein, and does not require the commissure posts 210 of the heart valve 100 to be deflected radially inward.

Figure 30B:
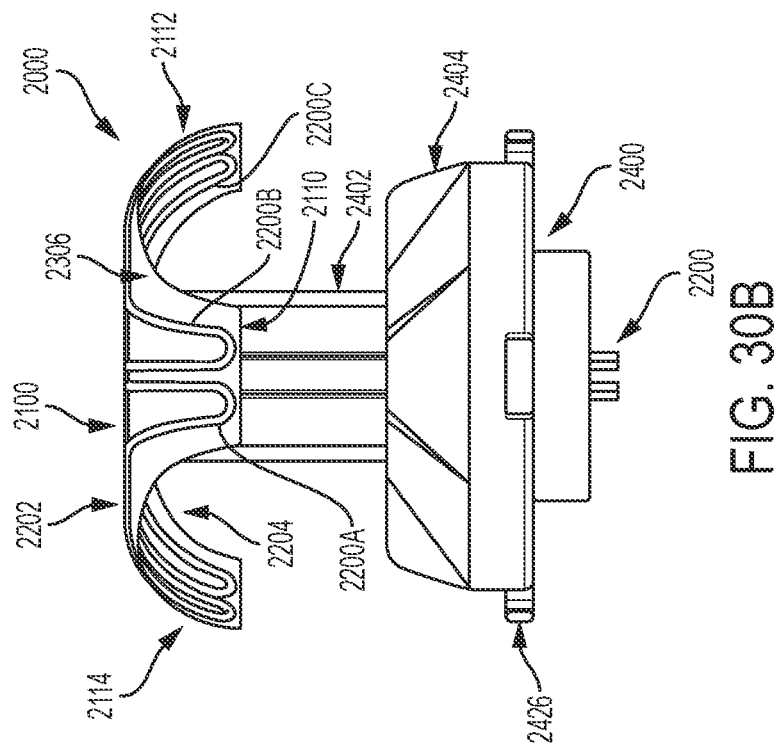
FIGS. 30A-30B are schematic illustrations of the example suture guard shown in FIG. 29A with the heart valve removed for clarity, in accordance with an embodiment.
Figure 30A:
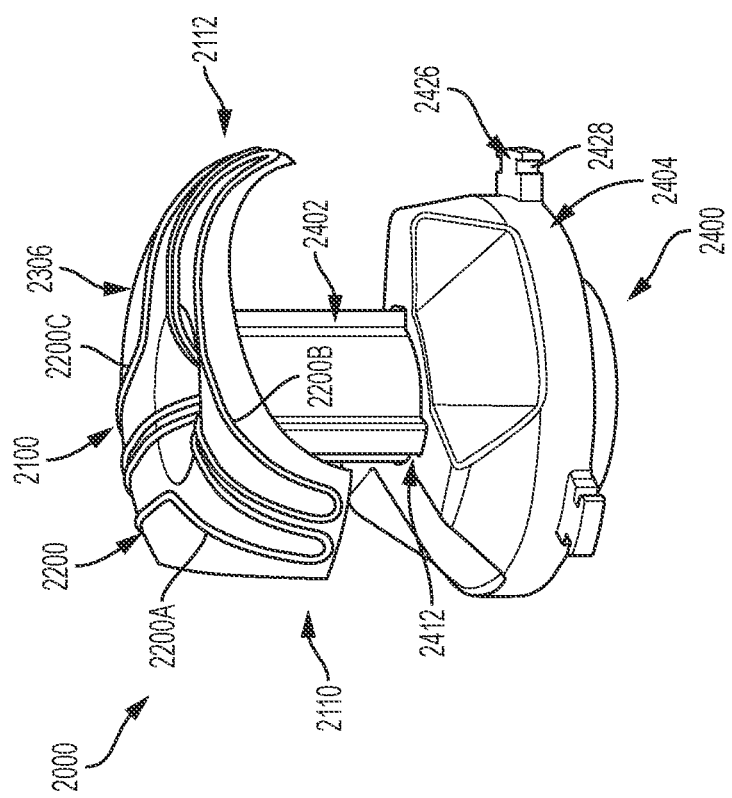
Figure 31B:
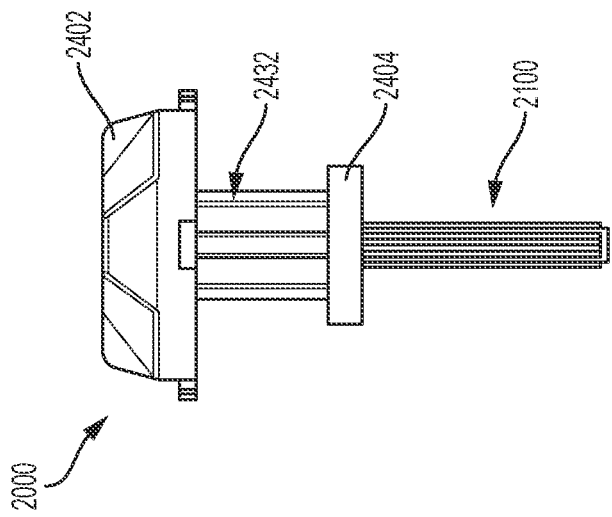
FIGS. 31A-31B are schematic illustrations of the example suture guard shown in FIG. 30A in a non-deployed configuration, in accordance with an embodiment.
Figure 31A:
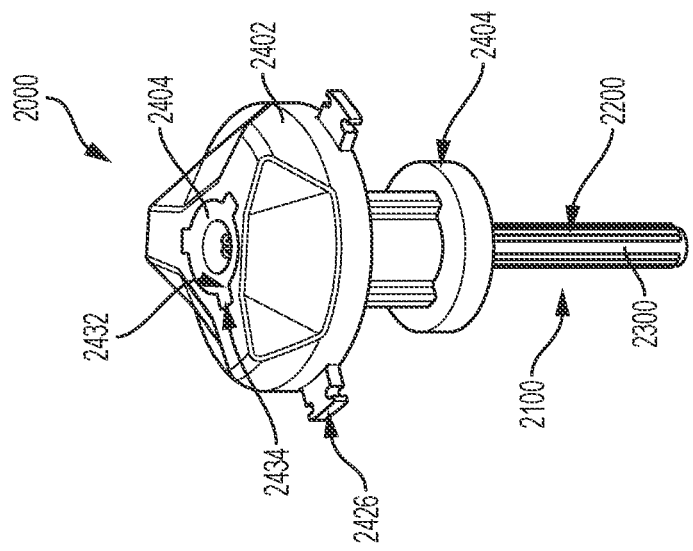
Figure 29E:
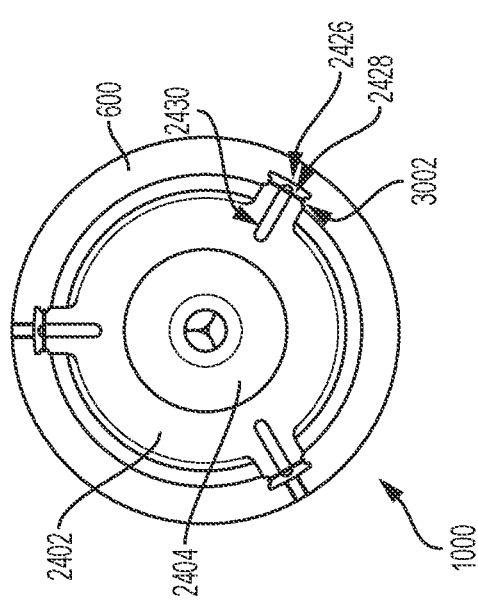

FIGS. 29A-29E provide illustration of a system 1000 including an example suture guard 2000 and a prosthetic heart valve 100, in accordance with an embodiment. The suture guard 2000 is shown in FIGS. 29A-29E in a deployed configuration in combination with a heart valve 100, where the suture guard 2000 covers one or more portions of the commissure posts 210 of the heart valve 100. FIGS. 30A-30C illustrate the suture guard 2000 in the deployed configuration with the heart valve 100 removed, for clarity. Conversely, FIGS. 31A-31B illustrate the suture guard 2000 in the non-deployed configuration with the heart valve 100 removed, for clarity.

In various embodiments, the suture guard 2000 generally includes a cover member and a base. In some examples, the cover member includes a frame element, and may optionally include a film element coupled to the frame element. For example, as shown in FIGS. 29A-31B, the suture guard 2000 includes a cover member 2100. In various examples, the cover member 2100 includes a frame element 2200 and a film element 2306. In some examples, the frame element 2200 and the film element 2306, collectively, define the cover member 2100. However, in some examples, the cover member 2100 may include the frame element 2200 without also requiring the film element 2306. In yet further examples, similar to those discussed above with respect to FIG. 6, a suture guard may include a cover member without a frame element. FIG. 29D is a top view of the system 1000 consistent with FIG. 29C, but with the film element 2306 highly transparent to illustrate the frame element 2200 extending into the base 2400

The frame element 2200 may be formed of one or more elongate members (e.g., a wire). In the exemplary embodiments depicted in FIGS. 29A-33B, the frame element 2200 is formed of a plurality of interrelated elongate members, 2200A, 2200B, and 2200C, that collectively define a cover member 2100 having a triple petal configuration. It should be understood, however, that the depicted frame element 2200 is not the only frame element configuration envisioned within the scope of the disclosure. The frame element 2200 can differ from the embodiments depicted in FIGS. 29A-33B in numerous ways such as, but not limited to, the number of petals, the geometries of the interrelated elongate members, including the various curvatures and angles of the interrelated elongate members, collectively, and individually, the number of elongate members forming the frame element 2200 (e.g., 1, 2, 3, elongate members, such as a single continuous elongate member, or multiple discrete yet interrelated elongate members), and/or the diameter(s) of the elongate members.

The elongate members 2200A, 2200B, and 2200C may be formed of various materials and/or combinations of materials. In exemplary embodiments, nitinol (NiTi) is used as the material of the elongate members. However, other materials such as stainless steel, polymeric materials, polyamide, polyester, polyimide, biosorbable polymers, a cobalt, chromium, nickel alloy, or any other appropriate biocompatible material, and combinations thereof, may be used as the material of the elongate members. In various embodiments, the frame element 2200 is generally conformable, fatigue resistant, elastic, and distensible such that the frame element 2200 can transition between deployed and non-deployed configurations. In various embodiments, the frame element 2200 provides structure and shape for the cover member 2100 of the suture guard 2000. In the embodiment depicted in FIGS. 29A-33B, the frame element 2200 provides a supportive structural framework for the film element 2306, which may otherwise be relatively flaccid and flexible.

In various embodiments, the film element 2306 may attached to or otherwise coupled with at least a portion of the frame element 2200. In some examples, the film element 2306 is attached to the frame element 2200 with an adhesive material, such as, for example, a silicone, a polyurethane, or fluorinated ethylene propylene (FEP). Silicone, for example, may be utilized as a bonding agent to adhere the film element 2306 to the frame element 2200. The adhesive material may be applied to portions of the frame element 2200 or to all of the frame element 2200.

In some examples, some or all of the film element 2306 is disposed on both sides (e.g., a first side 2202 and a second side 2204) of the frame element 2200 such that the elongate members—e.g., elongate members 2200A, 2200B, and 2200C—are encapsulated by the film element 2306. In some examples, the first side 2202 of the frame element 2200 corresponds to a portion of the cover member 2100 that faces the heart valve 100 when the suture guard 2000 is in the deployed configuration. This first side 2202 of the frame element 2200 may alternatively be referred to as the portion of the cover member 2100 exposed to an interior lumen of the base 2400 of the suture guard 2000 in the non-deployed configuration (also referred to herein as the delivery configuration). In some examples, the second side 2204 of the frame element 2200 corresponds to a portion of the cover member 2100 opposite the first side 2202, and that faces away from the heart valve 100 when the suture guard 2000 is in the deployed configuration. In the deployed configuration, the first side 2202 can be understood to face in an outflow direction of the heart valve 100, while the second side 2204 can be understood to face in an inflow direction of the heart valve 100.

In various examples, portions of the film element 2306, such as those on opposing sides of the frame element 2200, may be adhered to each other so as to encapsulate portions of or the entirety of the frame element 2200. Stitching, lashing, banding, and/or clips may be alternatively used to attach the film element 2306 to the frame element 2200. In some embodiments, a combination of techniques is used to attach the film element 2306 to the frame element 2200.

In various embodiments, the film element 2306 may be formed of a membranous material that inhibits or reduces the passage of blood and/or other bodily fluids and materials through the film element 2306. In an exemplary embodiment, the film element 2306 is a polymer material, such as, for example, a fluoropolymer material. In at least one embodiment, the film element 2306 is an expanded polytetrafluoroethylene membrane. It is to be appreciated that the film element 2306 may be formed of other materials, such as, but not limited to a silicone, a urethane, a polyester (e.g., DACRON®), and combinations thereof.

Figure 29B:
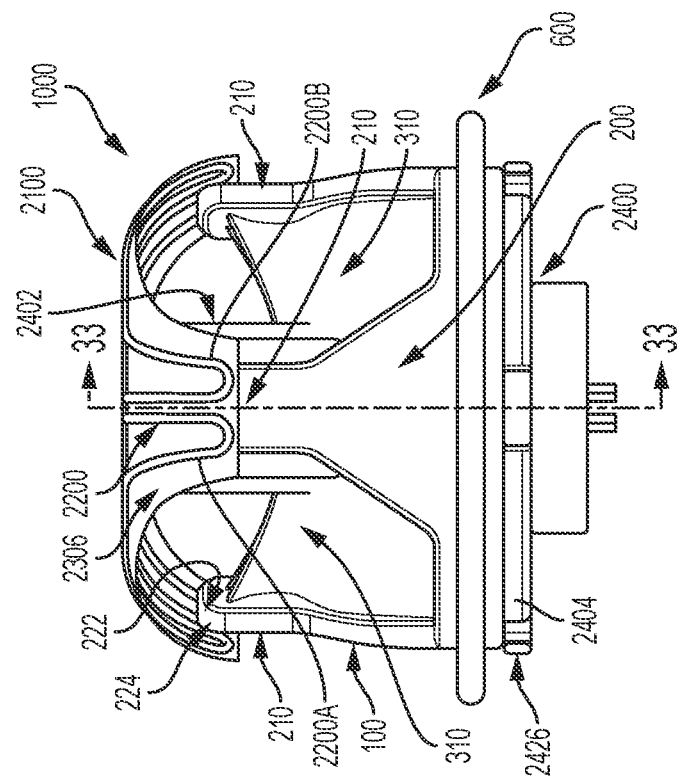
FIGS. 29A-29E are schematic illustrations of an example suture guard shown in a deployed configuration in combination with a heart valve, in accordance with an embodiment.
Figure 29A:
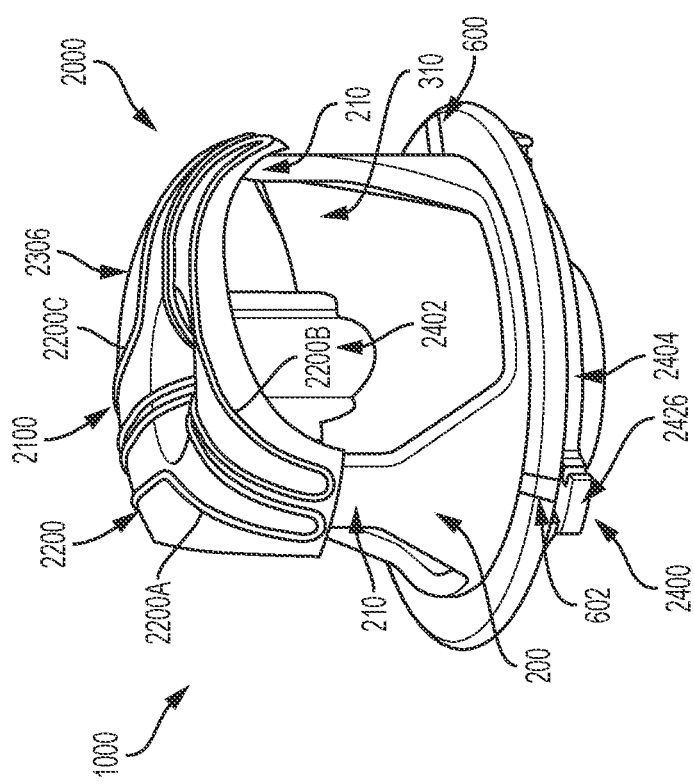
Figure 29D:
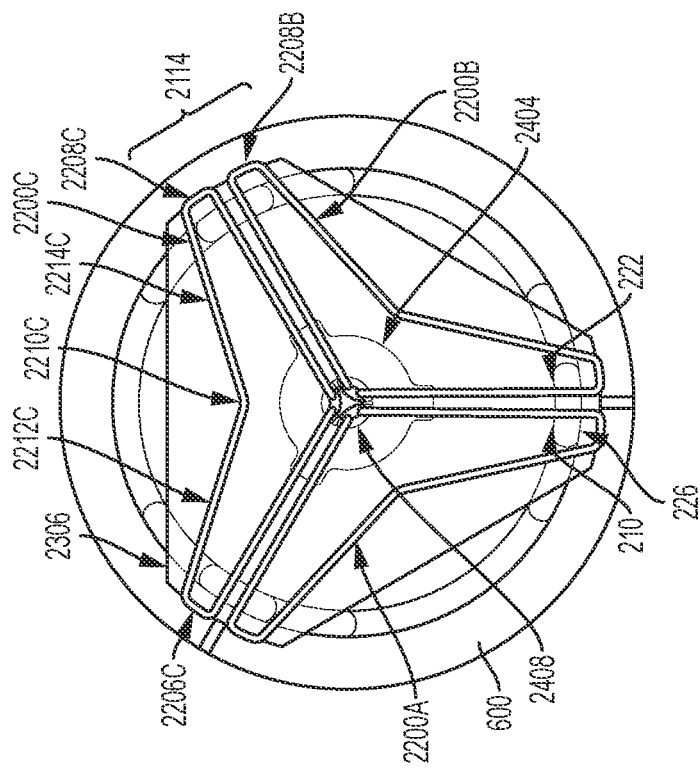

As shown in FIGS. 29A-30C, when in the delivery configuration, the suture guard 2000 is configured such that the cover member 2100 extends radially outwardly from the base 2400. As shown in FIGS. 29A-29C, the cover member 2100 extends radially outwardly of an interior surface(s) 222 of the outflow end(s) 224 of the commissure post(s) 210, distal to the outflow end(s) 224 of the commissure post(s) 210. In some examples, the cover member 2100 extends radially outwardly of an exterior surface(s) 226 of the outflow end(s) 224 of the commissure post(s) 210. FIG. 33A-1 is a cross sectional view of the system 1000 of FIG. 29B taken along line 33-33, with the film element 2306 removed for clarity.

As shown in FIG. 33A-1, the cover member 2100, including the frame element 2200 extends radially outwardly of the commissure post 210 of the heart valve 100. By extending radially outwardly of the commissure post 210 or otherwise covering the commissure post(s) 210, the cover member 2100 operates to deflect suture line (such as suture line 3000) extending along and exterior of the commissure post 210 such that the suture line does not become entangled with the commissure post 210 as the heart valve 100 is advanced along (and relative to) the suture line.

In various embodiments, the cover member 2100 is configured to adopt a predetermined deployment shape once deployed from the base 2400. In some example, the shape adopted by the cover member 2100 is dictated by a predetermined shape of the frame element 2200. In some other examples, the shape adopted by the cover member 2100 is additionally or alternatively dictated by a predetermined shape of the film element 2306. That is, in various embodiments, one or more of the materials of the cover member 2100 are configured with shape memory properties that operate to cause the cover member 2100 to adopt a predetermined deployment shape when the suture guard 2000 is transitioned to the deployed configuration.

In various embodiments, the cover member 2100 is configured to evert as it is deployed from the base 2400. For instance, as shown in FIGS. 29A-30C, in the deployed configuration, a first portion 2102 of the cover member 2100 is everted relative to second portion 2104 of the cover member 2100, with a transition region 2106 therebetween. Conversely, as shown in FIGS. 31A-31C in the non-deployed configuration (e.g., the delivery configuration), the first portion 2102 of the cover member 2100 is non-everted relative to the second portion 2104 of the cover member 2100. Thus, in some examples, in the deployed configuration, the cover member 2100 includes an everted portion (e.g., first portion 2102) and a non-everted portion (e.g., second portion 2104). As shown, in the non-deployed configuration each of the first and second portions 2102 and 2104 extend in an outflow direction with the transition region 2106 therebetween, whereas in the deployed configuration, the first portion 2102 (e.g., the everted portion) is everted such that the first portion 2102 extends from the transition region 2106 in an inflow direction towards an inflow end 2410 of the base 2400. Thus, an axial length of the cover member 2100 measured along the longitudinal axis of the suture guard is greater in the non-deployed configuration than in the deployed configuration. Moreover, a radial profile (e.g., a diameter of the cover member 2100) is greater in the deployed configuration than in the non-deployed configuration. It should thus be appreciated that, when transitioning from the non-deployed configuration to the deployed configuration, a portion of the axial length of the cover member 2100 is converted into the radial dimension of the cover member 2100. In other words, in various examples, in the non-deployed configuration the suture guard 2000 has a first axial length and a first diameter, whereas in the deployed configuration the suture guard has a second, shorter axial length and a second, greater diameter.

Such a deployed configuration provides that the cover member 2100 is configured to adopt a delivered profile conducive for covering one or more portions of the heart valve 100 during implantation of the heart valve 100 to help minimize a potential for suture line entanglement. With reference to FIG. 33A-2, it should be appreciated that, while the cover member 2100 is illustrated with the first portion 2102 of the cover member extending at an angle 0>θ>180 relative to a longitudinal axis of the system 1000 (e.g., angle θ is also representative of the relative angle between the longitudinal axis of the heart valve 100 and the first portion 2102, and the relative angle between the longitudinal axis of the second portion 2104 of the cover member 2100 and the first portion 2102), the angle θ may be equal to zero or one hundred eighty degrees (0≥θ≥180). Put differently, the first portion 2102 and the second portion 2104 may be parallel or non-parallel provided that that the cover member 2100 extends to a position radially outwardly of the interior surface(s) 222 of the outflow end(s) 224 of the commissure post(s) 210.

As mentioned above, the shape adopted by the cover member 2100 may be dictated by the properties of one or more of the frame element 2200 and the film element 2306. For instance, in some examples, the frame element 2200 includes a plurality of elongate members (e.g., 2200A, 2200B, and 2200C), where the elongate members include shape memory properties that operate to bias the cover member 2100 such that the cover member 2100 adopts a predetermined profile when not otherwise constrained, such as by the base 2400.

Figure 29C:
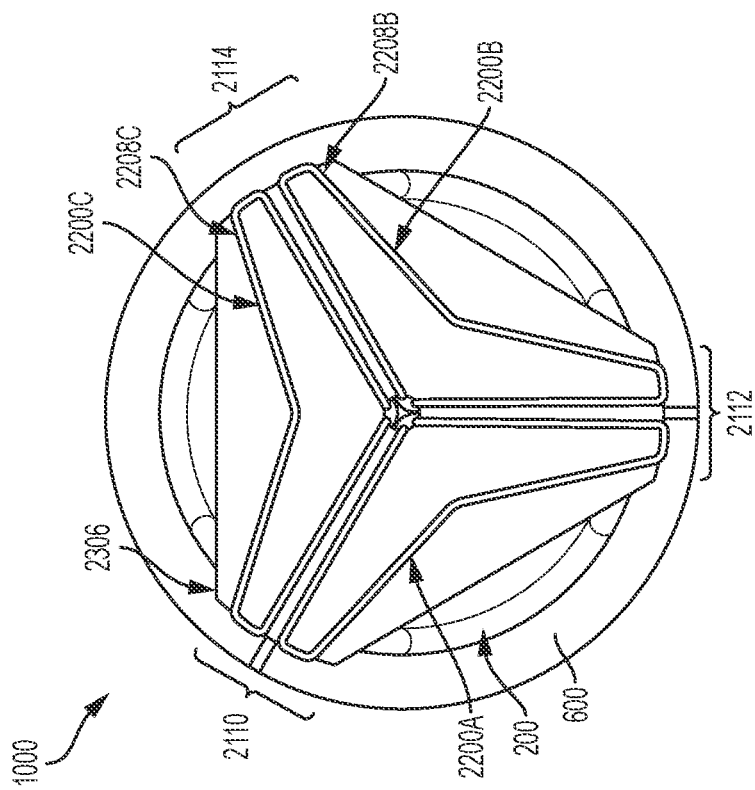

As shown in FIGS. 29C and 29D, the various elongate members 2200A, 2200B, and 2200C are shaped such that they collectively form a multi-petal geometry, where each petal is configured to cover or overlay a respective commissure post of a heart valve. The cover member 2100 shown in FIGS. 29C and 29D includes three petals, 2110, 2112, and 2114. The first petal 2110 includes elongate members 2200A and 2200C. The second petal 2112 includes elongate members 2200A and 2200B. The third petal 2114 includes elongate members 2200B and 2200C.

The elongate members 2200A, 2200B, and 2200C may be bent or formed with one or more bend regions, and optionally one or more loop regions. For example, elongate member 2200C includes a plurality of loop regions, including first loop region 2206C and second loop region 2208C, as well as a bend region 2210C. As shown, the bend region 2210C is situated between the first and second loop regions 2206C and 2208C. Situated between the bend region 2210C and the first loop region 2206C is a first length or strut 2212C of elongate member 2200C. Similarly, situated between the bend region 2210C and the second loop region 2208C is a second length or strut 2214C of elongate member 2200C. The elongate member 2200C is configured such that, when the suture guard 2000 is in the non-deployed configuration, the first and second lengths 2212C and 2214C of the elongate member 2200C are angled away from one another at a first angle. Conversely, when the suture guard 2000 is in the deployed configuration, the elongate member 2200C is configured such that the first and second lengths 2212C and 2214C are angled away from one another at a second angle greater than the first angle. That is, an angle of the bend region 2210C is configured to change as the suture guard is transitioned between the deployed and non-deployed configurations.

In particular, as the suture guard 2000 is transitioned from the non-deployed configuration to the deployed configuration, the bend region 2210C is configured such that the angle of bend region 2210C increases, such that the elongate member 2200C adopts the deployed profile illustrated in FIGS. 29C and 29D. In some examples, the angle of bend region 2210C increases from an acute angle to an obtuse angle as the suture guard 2000 is transitioned from the non-deployed configuration to the deployed configuration. Conversely, as the suture guard 2000 is transitioned from the deployed configuration to the non-deployed configuration, the bend region 2210C is configured such that the angle of bend region 2210C decreases, causing the first and second lengths 2212C and 2214C of the elongate member 2200C to be drawn closer to one another. In various examples, the elongate member 2200C is shape set to adopt the deployed profile illustrated in FIGS. 29C and 29D. The elongate members 2200A, 2200B, and 2200C may be shape set according to known methods. Accordingly, in such examples, when the suture guard 2000 is situated in the non-deployed configuration, the angle of the bend region 2210C is reduced such that the material of the bend region 2210C stores energy. As the suture guard 2000 is transitioned from the non-deployed configuration to the deployed configuration, this energy that is stored in the bend region 2210C is converted to kinetic energy and helps transition the suture guard 2000 to the deployed configuration (e.g., helps the cover member adopt the deployed profile).

In various examples, the first and second loop regions 2206C and 2208C of elongate member 2200C help define, at least in part, the first and third petals 2110 and 2114, respectively of the cover member 2100. As shown, petal 2114 is defined, at least in part, by loop region 2208C of elongate member 2200C and by loop region 2208B of elongate member 2200C. Petals 2110 and 2112 are similarly defined, at least in part, by a plurality of loop regions of a plurality of elongate elements. While the cover member of FIGS. 29C and 29D is configured such that each petal includes a plurality of loop portions, such as from a plurality of elongate elements, it should be appreciated that elongate elements may alternatively be configured such that each petal of the cover member 2100 includes only one of the elongate elements.

In various examples, opposing loop regions of a plurality of elongate elements that collectively define a petal of the cover member 2100 may be coupled together via the film element 2306 of the cover member 2100. For example, as shown, the film element 2306 couples together the loop regions of the elongate members 2200A and 2200C at petal 2110. Likewise, the film element 2306 couples together the loop regions of the elongate members 2200A and 2200B at petal 2112. Likewise, the film element 2306 couples together the loop regions of the elongate members 2200B and 2200C at petal 2114.

It should also be appreciated that while the suture guard 2000 is illustrated in FIG. 33A-1 in the deployed configuration with a portion of the cover member 2100 (e.g., the first portion 2102, or a portion thereof) extending proximal to the outflow end 224 of the commissure post(s) 210, the suture guard 2000 may alternatively be configured such that cover member 2100 does not extend proximal to the outflow end(s) 224 of the commissure post(s) 210, but instead extends radially outwardly of the interior surface(s) 222 of the commissure post(s) distal to the outflow end(s) 224 of the commissure post(s) 210.

The suture guard 2000 may configured such that the cover member 2100 is selectively deployable from the base 2400, or may alternatively be configured such that the cover member 2100 automatically deploys from the base 2400 upon an activation of the base 2400. That is, the cover member 2100 may deploy from the base 2400 to cover the commissure post(s) of the heart valve 100 without requiring manipulation of the cover member 2100 aside from activation of the base 2400. For instance, in some examples, the base 2400 is comprised of a support element 2402 and a shaft element 2404, where the shaft element 2404 is operable to translate (e.g., be advanced and/or retracted) relative to the support element 2402. In some such examples, the support element 2402 includes a lumen 2412 through which the shaft element 2404 extends. In some examples, a cross-sectional profile of the shaft element 2404 taken transverse to a longitudinal axis of the base 2400 (referred to hereinafter as a transverse cross-sectional profile of the shaft element) is complimentary of a luminal profile of the lumen 2412. In some examples, the shaft element 2404 includes one or more protrusions, such as protrusions 2432 extending along its longitudinal length that are complimentary to one or more features 2434 of the luminal profile of the support element 2402, and that operate to constrain the shaft element 2404 against substantial rotational movement relative to the support element 2402. As discussed in greater detail below, such protrusions may additionally or alternatively operate to bias or maintain the shaft element 2404 in one or more discrete positions (e.g., axial or angular) relative to the support element 2402.

In various examples, as the shaft element is advanced relative to the support element 2402, the cover member 2100 is automatically deployed from an outflow end 2406 of the shaft element 2404. In some examples, the shaft element 2404 includes a lumen 2408 extending through the shaft element 2404 and through which the cover member 2100 extends. Thus, in various examples, one or more of the frame element 2200 (including one or more of elongate members 2200A, 2200B, and 2200C) and the film element 2306 extends through and is translatable (e.g., advanceable or retractable) relative to the shaft element 2404 of the base 2400.

In various examples, one or more of the frame element 2200 and the film element 2306 are operably coupled to one or more of the support element 2402 and the shaft element 2404 such that advancement of the shaft element 2404 relative to the support element 2402 causes advancement (e.g., translation in the outflow/distal direction) of the cover member 2100 relative to the shaft element 2404, which causes the suture guard 2000 to transition to the deployed configuration, where the cover member 2100 extends radially outwardly of the lumen 2408 of the shaft element 2404.

Similarly, in various examples, one or more of the frame element 2200 and the film element 2306 are operably coupled to one or more of the support element 2402 and the shaft element 2404 such that retraction of the shaft element 2404 relative to the support element 2402 causes retraction (e.g., translation in the inflow/proximal direction) of the cover member 2100 relative to the shaft element 2404, which causes the suture guard 2000 to transition to the non-deployed (e.g., delivery) configuration. Associating the deployment and retraction of the cover member 2100 of the suture guard 2000 with the activation of the base 2400 provides for minimizing a potential for mishandling of the suture guard 2000, including premature deployment or retraction of the cover member 2100.

In addition to the discussion above, it should be appreciated that, in some examples, the suture guard 2000 is configured such that in the non-deployed (e.g., delivery) configuration the cover member 2100 is situated within the lumen 2408 of the base 2400 in a collapsed configuration. That is, in some examples, the suture guard 2000 is configured such that in the non-deployed configuration the cover member 2100, including the frame element 2200 and/or the film element 2306, is situated radially inwardly of the interior surface 222 of the outflow end 224 of the commissure post(s) 210.

It should also be appreciated that while the examples illustrated and described above involve a base 2400 that is configured such that a shaft element 2404 is translatable relative to a support element 2402, in various other examples, the base 2400 may be alternatively configured such that the shaft element 2404 is additionally or alternative rotatably coupled to the support element 2402. In such examples, in addition to or as an alternative to translation of the shaft element 2404 relative to the support element 2402, the shaft element 2404 is rotatable relative to the support element 2402, where such rotation and/or translation operates to cause the cover member 2100 to extend radially outwardly of the interior surface 222 of the outflow end(s) 224 of the commissure post(s) 210.

In some examples, one or more regions of the base 2400, such as a wall of the lumen 2408, operate as one or more bearing surfaces along which the cover member 2100 interacts as the cover member 2100 transitions between everted and non-everted configurations. Accordingly, in various examples, the base 2400 is configured to constrain the cover member 2100 in a collapsed configuration when the suture guard is in the non-deployed configuration.

In some examples where the base 2400 includes components (e.g., support element 2402 and shaft element 2404) that are configured to translate and/or rotate relative to one another to facilitate the extension of the cover member 2100 radially outwardly of the interior surface(s) 222 of the outflow end(s) 224 of the commissure post(s) 210, the base 2400 may additionally include one or more features that operate to bias the shaft element 2404 into one or more discrete positions (e.g., axial or angular) relative to the support element 2402. For example, as shown in FIG. 33A-1, the shaft element 2404 includes biasing members 2414A and 2414B, which are each configured to interface with a flange 2416 of the support element 2402. As shown, the suture guard 2000 is in the deployed configuration with the shaft element 2404 in a distally advanced position relative to the support element 2402, where flange 2416 is situated between biasing member 2414A and a flange 2418 of the shaft element 2404. With the flange 2416 so positioned, the biasing member 2414A and the flange 2418 operate to help maintain the suture guard 2000 in the deployed position by biasing the flange 2416 between biasing member 2414A and a flange 2418.

Figure 33B:
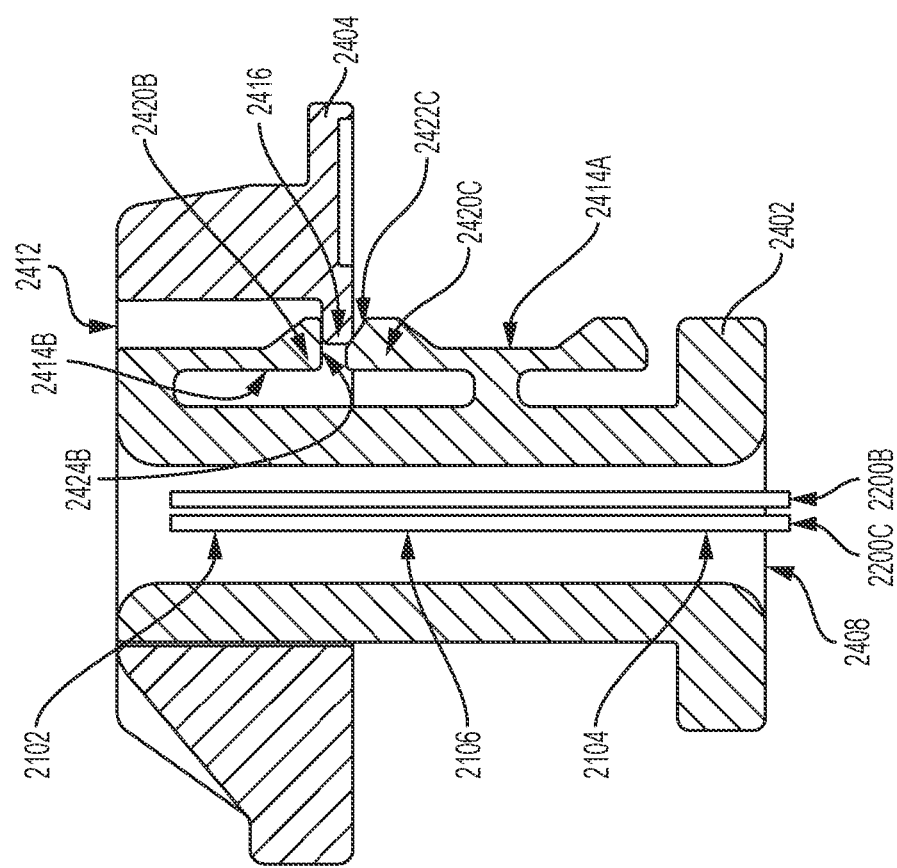
FIG. 33B is a cross-sectional view of the example suture guard shown in FIG. 33A-1 in a non-deployed configuration and with the heart valve removed for clarity, in accordance with an embodiment.

In various examples, the biasing force of the biasing member 2414A may be overcome by applying a proximally directed longitudinal force to the shaft element 2404 to deflect tab 2420A radially inwardly of flange 2416 such that biasing member 2414A can clear flange 2416 and shaft element 2404 can be proximally withdrawn relative to support element 2402. In various examples the biasing member(s) (e.g., 2414A and/or 2414B) may include one or more ramp features, such as ramp feature 2422A, that help facilitate a deflection of the biasing member as longitudinal force is applied (e.g., proximally and/or distally) to the shaft element 2404. Such ramp features may be configured as bearing surfaces that engage and slide along flange 2416 as the shaft element 2404 is translated relative to the support element 2402. In some examples, one or more of the biasing members (e.g., 2414A and/or 2414B) may include one or more stop features, that operates to obstruct translation of the shaft element 2404 beyond a designated axial position relative to the support element 2402. For example, as shown in FIG. 33B, biasing member 2414B includes stop feature 2424B, which is a portion of tab 2420B, that is configured to engage flange 2416 to obstruct proximal translation of the shaft element 2404 beyond the position illustrated in FIG. 33B, which is the position of the shaft element 2404 in the non-deployed configuration. It should be appreciated that heart valve 100 has been removed from FIG. 33B for clarity. Referring back to FIG. 33A-1, in some examples, the flange 2418 of the shaft element 2404 may operate as a stop feature that functions to obstruct distal translation of the shaft element 2404 beyond the position illustrated in FIG. 33A-1, which is the position of the shaft element 2404 in the deployed configuration. As shown in FIG. 33B, the suture guard 2000 is in the non-deployed configuration with the shaft element 2404 in a proximally advanced position relative to the support element 2402, where flange 2416 is situated between biasing member 2414A and tab 2420B. With the flange 2416 so positioned, the biasing member 2414A and the tab 2420B operate to help maintain the suture guard 2000 in the deployed position (e.g., a discrete position) by biasing the flange 2416 between biasing member 2414A and the tab 2420B.

In some examples, the base 2400 may be configured to interface with any of the delivery handles herein illustrated and described. Accordingly, one or more of the delivery handles illustrated and/or described herein may be utilized to advance the suture guard 2000, including the heart valve 100 to a target region within a patient's heart, and/or to cause the suture guard 2000 to transition between delivery and deployed configurations. Accordingly, it is to be appreciated that one or more of the delivery handles illustrated and/or described herein may include one or more mechanisms configured to cause the shaft element 2404 to be advanced relative to the support element 2402.

In some examples, the base 2400 may be configured to be coupleable to one or more regions of the heart valve 100. For example, as shown in FIG. 30A, the base 2400 includes a retention feature 2426. Retention feature 2426 is a protrusion extending radially from a portion of the base 2400, such as from a portion of the support element 2402. In various examples, suture can be passed through the sewing cuff 600 of the heart valve 100 and looped around the retention feature 2426 to secure or otherwise couple the heart valve 100 to the suture guard 2000. In some examples, the retention feature 2424 may include a guide 2428 that operates to retain engagement between the suture and the retention feature 2424. For instance, as shown in FIG. 30A, the guide 2428 includes a channel or groove, and in FIG. 29E, a suture or fiber 3002 is shown extending within the channel or groove of guide 2428.

In some examples, the base 2400 may be further configured to include a cut slot 2430, similar to the cut slot described above with respect FIG. 2C. To decouple the suture guard 2000 from the heart valve 100, the surgeon cuts the suture or fiber 3002 in the designated area of cut slot 2430, which releases the suture or fiber extending through the sewing cuff 600 and looping around the retention feature 2426, thereby allowing the heart valve 100 to be decoupled from the suture guard 2000.

While the cover member 2100 illustrated and described herein is shown with a tri-lobal or three petal configuration, it is to be appreciated that the cover member 2100 may be configured to include less than three petals, such as two petals, or alternatively more than three petals, such as four, five, six, or more than six petals. Indeed, in various examples, the cover member may comprise any number of petals provided that the cover member 2100 is operable to be deployed and retracted in accordance with the disclosure above. In some examples, in lieu of a petal or lobed design, the cover member 2100 may not include any petals, but may instead be configured as an evertable hood consistent with the profile illustrated and described above with respect to FIG. 6.

Moreover, while the cover member illustrated and described in association with FIGS. 29A-33B includes a frame element 2200 having discrete elongate elements 2200A, 2200B, and 2200C, it should be appreciated that the frame element 2200 may include a single continuous elongate element. The single continuous elongate element may be bent into the configuration illustrated and described above with respect to FIGS. 29A-33B, or may alternatively be formed into alternative configurations. For instance, in some examples, the frame element 2200 may be helically shaped. Additionally, while the elongate elements 2200A, 2200B, and 2200C, are illustrated and described as including a bend region, such as bend region 2210C, it should be appreciated that the elongate element(s) may include a plurality of bend regions.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A system comprising:
   a prosthetic valve;
   a suture guard coupled to the prosthetic valve;
   a sleeve including a coupling portion adjustably coupled to the suture guard, such that a position of the suture guard relative to the sleeve is adjustable;
   a fiber extending from the sleeve to the suture guard; and
   a delivery handle operable to apply tension to the fiber by adjusting the position of the suture guard relative to the sleeve;
   wherein the fiber is coupled to a commissure post of the prosthetic valve, the fiber operable to deflect the commissure post toward a longitudinal axis of the heart valve when tension is applied to the fiber.

2. The system of claim 1, wherein the coupling portion of the sleeve includes an externally threaded portion and corresponds to an internally threaded portion of the suture guard.

3. The system of claim 2, wherein the position of the suture guard relative to the sleeve is adjusted by the externally threaded portion of the delivery device being moved relative to the internally threaded portion of the suture guard.

4. The system of claim 1, wherein the sleeve includes a tab operable to interface with the suture guard.

5. The system of claim 1, wherein the sleeve is operable to be separated from the suture guard.

6. The system of claim 1, wherein the delivery handle is operable to be uncoupled from the sleeve.

7. The system of claim 6, wherein the delivery handle includes a dovetailed portion that is positioned at an interface between the sleeve and the delivery handle, the delivery handle being operable to uncouple from the sleeve when the delivery handle is translated perpendicularly to a longitudinal axis defined by the sleeve, such that the dovetailed portion of the delivery handle uncouples from the sleeve.

8. The system of claim 6, wherein the delivery handle is operable to release the sleeve when pressure is applied to the delivery handle at a predefined position, wherein application of pressure at the predefined position opens the delivery handle.

9. The system of claim 1, wherein the delivery handle is operable to move relative to the sleeve such that movement of the delivery handle adjusts tension applied to the fiber.

10. The suture guard of claim 1, wherein the delivery handle is operable to move the sleeve in a distal to proximal direction relative to the suture guard.

11. The suture guard of claim 1, wherein the fiber is configured to be tensioned in a distal to proximal direction to deflect the commissure post toward the longitudinal axis of the heart valve.

12. A suture guard for a prosthetic valve having commissure posts and defining a valve orifice having an inflow portion and an outflow portion, the suture guard comprising:
    a holding member including tubular member, the tubular member including a first portion configured to be positioned in the inflow portion of the prosthetic valve and a second, everted portion configured to be positioned radially outward of the commissure posts of the prosthetic valve and cover an entirety of the outflow portion.

13. The suture guard of claim 12, wherein the holding member is configured to be secured to the prosthetic valve by a fiber.

14. The suture guard of claim 13, wherein the fiber is configured to be arranged through a portion of the prosthetic valve.

15. The suture guard of claim 13, wherein the holding member includes a surface along which the fiber is operable to slide as the fiber is tensioned.

16. The suture guard of claim 13, wherein the holding member is configured to be released from the prosthetic valve when the fiber tension is reduced.

17. The suture guard of claim 16, wherein the holding member is configured to be removed from the prosthetic valve by advancing the holding member through the valve orifice.

18. The suture guard of claim 12, wherein the everted portion includes a first diameter, wherein the first diameter is such that when the everted portion is engaged with the commissure posts of the prosthetic valve, the commissure posts are deflected radially inward by the everted portion.

19. The suture guard of claim 12, wherein the holding member is formed from a compressible material.

20. A system comprising:
    a prosthetic valve;
    a suture guard coupled to the prosthetic valve;
    a sleeve including a coupling portion adjustably coupled to the suture guard, such that a position of the suture guard relative to the sleeve is adjustable;
    a fiber extending from the sleeve to the suture guard; and a delivery handle operable to apply tension to the fiber by adjusting the position of the suture guard relative to the sleeve;

wherein the coupling portion of the sleeve includes an externally threaded portion and corresponds to an internally threaded portion of the suture guard.

21. The system of claim 20, wherein the position of the suture guard relative to the sleeve is adjusted by the externally threaded portion of the delivery device being moved relative to the internally threaded portion of the suture guard.

22. The system of claim 20, wherein the delivery handle is operable to move the sleeve in a distal to proximal direction relative to the suture guard to apply tension to the fiber.

23. A system comprising:
a prosthetic valve;
a suture guard coupled to the prosthetic valve;
a sleeve including a coupling portion adjustably coupled to the suture guard, such that a position of the suture guard relative to the sleeve is adjustable;
a fiber extending from the sleeve to the suture guard; and
a delivery handle operable to apply tension to the fiber by adjusting the position of the suture guard relative to the sleeve;
wherein the delivery handle is operable to be uncoupled from the sleeve; and
wherein the delivery handle includes a dovetailed portion that is positioned at an interface between the sleeve and the delivery handle, the delivery handle being operable to uncouple from the sleeve when the delivery handle is translated perpendicularly to a longitudinal axis defined by the sleeve, such that the dovetailed portion of the delivery handle uncouples from the sleeve.

24. A system comprising:
a prosthetic valve;
a suture guard coupled to the prosthetic valve;
a sleeve including a coupling portion adjustably coupled to the suture guard, such that a position of the suture guard relative to the sleeve is adjustable;
a fiber extending from the sleeve to the suture guard; and
a delivery handle operable to apply tension to the fiber by adjusting the position of the suture guard relative to the sleeve;
wherein the delivery handle is operable to be uncoupled from the sleeve; and
wherein the delivery handle is operable to release the sleeve when pressure is applied to the delivery handle at a predefined position, wherein application of pressure at the predefined position opens the delivery handle.

* * * * *